United States Patent
Kropf et al.

(10) Patent No.: US 9,593,295 B2
(45) Date of Patent: Mar. 14, 2017

(54) SURFACTANTS WITH LOWER CMC, AND SURFACTANT SYSTEMS AND DETERGENTS CONTAINING SAID SURFACTANTS

(71) Applicants: Henkel AG & Co. KGaA, Duesseldorf (DE); Studiengesellschaft Kohle mbH, Muelheim an der Ruhr (DE)

(72) Inventors: Christian Kropf, Hilden (DE); Nicole Bode, Duesseldorf (DE); Danuta Bedrunka, Dormagen (DE); Roberto Rinaldi, Muehlheim an der Ruhr (DE); Hebert Jesus Estevez Rivera, Bochum (DE)

(73) Assignees: Henkel AG & Co. KGaA & Studiengesellschaft, Duesseldorf (DE); Kohle mbH, Muelheim an der Ruhr (DE)

( * ) Notice: Subject to any disclaimer, the term of this patent is extended or adjusted under 35 U.S.C. 154(b) by 0 days.

(21) Appl. No.: 14/813,565

(22) Filed: Jul. 30, 2015

(65) Prior Publication Data
US 2015/0337237 A1  Nov. 26, 2015

Related U.S. Application Data

(63) Continuation of application No. PCT/EP2014/050264, filed on Jan. 9, 2014.

(30) Foreign Application Priority Data

Feb. 1, 2013  (DE) .................. 10 2013 001 859

(51) Int. Cl.
| | |
|---|---|
| *C11D 1/24* | (2006.01) |
| *C11D 1/29* | (2006.01) |
| *C11D 1/37* | (2006.01) |
| *C11D 1/72* | (2006.01) |
| *C11D 1/831* | (2006.01) |
| *C07C 309/42* | (2006.01) |
| *C11D 1/22* | (2006.01) |
| *C11D 1/83* | (2006.01) |
| *C11D 1/14* | (2006.01) |

(52) U.S. Cl.
CPC .............. *C11D 1/22* (2013.01); *C07C 309/42* (2013.01); *C11D 1/24* (2013.01); *C11D 1/29* (2013.01); *C11D 1/37* (2013.01); *C11D 1/83* (2013.01); *C11D 1/831* (2013.01); *C11D 1/143* (2013.01); *C11D 1/72* (2013.01)

(58) Field of Classification Search
CPC .... C11D 1/24; C11D 1/29; C11D 1/37; C11D 1/72; C11D 1/831; C11D 7/261; C11D 7/262; C07C 309/42
See application file for complete search history.

(56) References Cited

U.S. PATENT DOCUMENTS

| | | |
|---|---|---|
| 2,037,371 A | 4/1936 | Fanto et al. |
| 4,533,622 A | 8/1985 | Takahashi et al. |
| 6,552,107 B1 | 4/2003 | Paul et al. |
| 2006/0194709 A1* | 8/2006 | Boone ................ C11D 17/0013 510/383 |

FOREIGN PATENT DOCUMENTS

| | | | |
|---|---|---|---|
| CN | 101898098 | * 12/2010 | .............. B01F 17/12 |
| DE | 2533102 A1 | 1/1977 | |
| EP | 538875 | * 4/1993 | .............. G03C 7/30 |
| EP | 0538875 A1 | 4/1993 | |
| JP | 63-262647 A | 10/1988 | |
| JP | 5-313276 A | 11/1993 | |

OTHER PUBLICATIONS

English abstract of CN 101898098, dated Dec. 2010.*

(Continued)

*Primary Examiner* — Brian P Mruk
(74) *Attorney, Agent, or Firm* — Thomas G. Krivulka

(57) ABSTRACT

The invention relates to surfactants of the formula (I), in which $R^1$ stands for —H or —$CH_3$; $R^2$, $R^3$, $R^4$, $R^5$, $R^6$ independently stand for —H, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —OH, —$OCH_3$, —$OCH_2CH_3$, —$OCH_2CH_2CH_3$, —$OCH(CH_3)_2$, a linear or branched alkyl group containing 8 to 20 C atoms, or —$SO_3^-X^+$; $X^+$ stands for a monovalent cation or the nth part of an n-valent cation; exactly one radical $R^2$, $R^3$, $R^4$, $R^5$, $R^6$ stands for —$SO_3^-X^+$; and exactly one radical $R^2$, $R^3$, $R^4$, $R^5$, $R^6$ stands for a linear or branched alkyl radical containing 8 to 20 C atoms.

16 Claims, No Drawings

(56) References Cited

OTHER PUBLICATIONS

PCT International Search Report (PCT/EP2014/050264) dated Mar. 13, 2014.
Sethi et al., "Relation of Structure to Surface-active Properties of Alkoxy-Alkylbenzen Sulphonates", Indian Journal of Chemistry, vol. 2, pp. 277-282, 1964, XP008160397.
Paul, "Melt/solution Processable Conducting Polyaniline with Novel Sulfonic Acid Dopants and its Thermoplastic Blends", Synthetic Metals, vol. 114, pp. 27-35, 2000, XP055107466.
Database WPI, Week 201124, Thomson Scientific, London, GB, AN 2011-A25466, 2013, XP002721721.
Database WPI, Week 201114, Thomson Scientific, London, GB, AN 2011-A25467, 2013, XP002721722.
Database WPI, Week 201124, Thomson Scientific, London, GB, AN 2011-A25465, 2013, XP002721723.

\* cited by examiner

SURFACTANTS WITH LOWER CMC, AND SURFACTANT SYSTEMS AND DETERGENTS CONTAINING SAID SURFACTANTS

FIELD OF THE INVENTION

The present invention generally relates to surfactants which may be produced on the basis of renewable raw materials, and which have excellent critical micelle concentrations (CMC) and produce low interfacial tensions. The invention further relates to surfactant mixtures containing the surfactants according to the invention, and detergents or cleaning agents which contain surfactants or surfactant mixtures according to the invention.

BACKGROUND OF THE INVENTION

The use of surfactants for reducing the surface tension of water, for forming dispersions, and for solubilization is generally known in the field of detergents and cleaning agents. Although many surfactants based completely or partially on renewable raw materials have been produced in recent years, some powerful, widely used representatives are still based on petrochemicals. In addition, there is a constant desire to provide surfactants having excellent application-related properties (low CMC, low surface tension) to be able to achieve high detergent and cleaning power, even when small quantities of surfactant are used.

The object of the present invention is to provide surfactants which have excellent application-related properties (low CMC, low surface tension) and which may be produced on the basis of renewable raw materials. A further aim is that the surfactants are well tolerated by the skin and compatible with other surfactants to allow production and storage of surfactant systems and surfactant mixtures which are suited in particular for detergents and cleaning agents.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

Surfactants of formula (I)

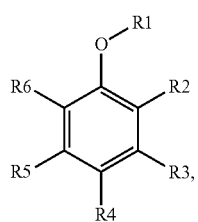

(I)

in which $R^1$ stands for —H or —$CH_3$; $R^2$, $R^3$, $R^4$, $R^5$, $R^6$ independently stand for —H, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —OH, —$OCH_3$, —$OCH_2CH_3$, —$OCH_2CH_2CH_3$, —$OCH(CH_3)_2$, a linear or branched alkyl radical containing 8 to 20 C atoms, or —$SO_3^-X^+$; $X^+$ stands for a monovalent cation or the nth part of an n-valent cation, with the condition that exactly one radical $R^2$, $R^3$, $R^4$, $R^5$, $R^6$ stands for —$SO_3^-X^+$ and exactly one radical $R^2$, $R^3$, $R^4$, $R^5$, $R^6$ stands for a linear or branched alkyl radical containing 8 to 20 C atoms.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

In a first embodiment, the subject matter of the present invention relates to surfactants of formula (I)

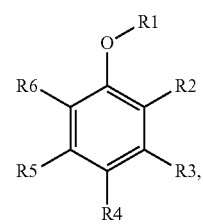

(I)

in which
$R^1$ stands for —H or —$CH_3$,
$R^2$, $R^3$, $R^4$, $R^5$, $R^6$ independently stand for —H, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —OH, —$OCH_3$, —$OCH_2CH_3$, —$OCH_2CH_2CH_3$, —$OCH(CH_3)_2$, a linear or branched alkyl radical containing 8 to 20 C atoms, or —$SO_3^-X^+$,
$X^+$ stands for a monovalent cation or the nth part of an n-valent cation,
with the condition that
exactly one radical $R^2$, $R^3$, $R^4$, $R^5$, $R^6$ stands for —$SO_3^-X^+$ and
exactly one radical $R^2$, $R^3$, $R^4$, $R^5$, $R^6$ stands for a linear or branched alkyl radical containing 8 to 20 C atoms.

These surfactants may be produced by alkylation and sulfonation of phenol or phenol derivatives, which are available from native sources, for example by hydrogenation of lignin. During their production, the surfactants typically occur as isomeric mixtures. They may be used either as an isomeric mixture or, after isomer separation, as a pure isomer. However, isomer separation is generally not necessary, and therefore is also not preferred.

These surfactants surprisingly have a very low critical micellar concentration (CMC), and in aqueous solution result in very low surface tensions. The CMC is determined by measuring the surface tension of an aqueous solution of the surfactants as a function of the concentration, at 25° C. and a pH of 8.5. Surfactants are particularly preferred which have a CMC of less than 0.1 g/L and in particular less than 0.09 g/L. Phenol derivatives (isomers or isomeric mixtures) are very particularly preferred which have a CMC of 0.06 g/L maximum, in particular 0.04 g/L or less, 0.03 g/L or less, 0.02 g/L or less, or even 0.002 g/L or less (in comparison, a branched C12 alkylbenzenesulfonate has a CMC of 0.11 g/L under the described conditions).

In another preferred embodiment of the invention, the surfactants not only have very low critical micelle concentrations, but also produce low interfacial tensions. The interfacial tension of an aqueous surfactant solution (1 g/L)

is measured against triolein at 25° C. and a pH of 8.5 by means of the spinning drop method. (The measured value is taken after a 20-minute equilibration period.) Surfactants (isomers or isomeric mixtures) which produce interfacial tensions of less than 2 mN/m, more advantageously 1.8 mN/m maximum, particularly preferably 1.6 mN/m maximum, according to the described method are very particularly preferred. Some surfactants even produce interfacial tensions of 1.4 mN/m, 1.3 mN/m, 0.8 mN/m, 0.3 mN/m, or even lower.

Surfactants (isomers or isomeric mixtures) which have a CMC of 0.01 to 0.06 g/L and at the same time produce an interfacial tension of 1.6 mN/m maximum are very particularly preferred. The following are listed here as such preferred surfactants, strictly by way of example (R stands for $C_{14}H_{29}$ in each case):

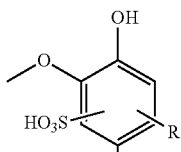

(CMC: 0.2 g/L; interfacial tension: 1.3 mN/m)

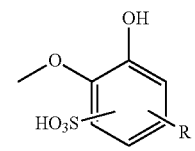

(CMC: 0.06 g/L; interfacial tension: 0.8 mN/m)

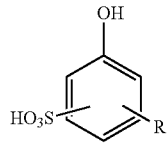

(CMC: 0.03 g/L; interfacial tension: 0.3 mN/m)

In addition, the surfactants have very good compatibility with other surfactants, and may be provided in the form of surfactant mixtures that are stable in storage. A further subject matter of the present invention therefore relates to a surfactant mixture containing a) at least one surfactant of formula (I)

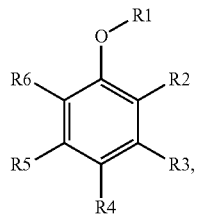

in which
R$^1$ stands for —H or —CH$_3$,
R$^2$, R$^3$, R$^4$, R$^5$, R$^6$ independently stand for —H, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —OH, —OCH$_3$, —OCH$_2$CH$_3$, —OCH$_2$CH$_2$CH$_3$, —OCH(CH$_3$)$_2$, a linear or branched alkyl radical containing 8 to 20 C atoms, or —SO$_3^-$X$^+$,
X$^+$ stands for a monovalent cation or the nth part of an n-valent cation,
with the condition that
exactly one radical R$^2$, R$^3$, R$^4$, R$^5$, R$^6$ stands for —SO$_3^-$X$^+$ and
exactly one radical R$^2$, R$^3$, R$^4$, R$^5$, R$^6$ stands for a linear or branched alkyl radical containing 8 to 20 C atoms;
b) at least one further surfactant.

The surfactants and surfactant mixtures according to the invention are very well suited as surfactants for detergents and cleaning agents, cosmetics such as shampoos, toothpastes, etc., and for the other areas of use in which alkylbenzenesulfonates, for example, are used (food industries, geosciences, tertiary oil production, plastics technology, metalworking, photography, paper recycling, tool cleaning, firefighting, and the like).

Particularly good results are achieved in detergents and cleaning agents, so that a further subject matter of the present invention relates to detergents or cleaning agents which contain at least one surfactant of formula (I)

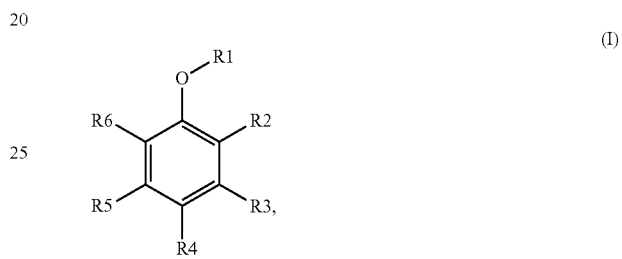

in which
R$^1$ stands for —H or —CH$_3$,
R$^2$, R$^3$, R$^4$, R$^5$, R$^6$ independently stand for —H, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —OH, —OCH$_3$, —OCH$_2$CH$_3$, —OCH$_2$CH$_2$CH$_3$, —OCH(CH$_3$)$_2$, a linear or branched alkyl radical containing 8 to 20 C atoms, or —SO$_3^-$X$^+$,
X$^+$ stands for a monovalent cation or the nth part of an n-valent cation,
with the condition that
exactly one radical R$^2$, R$^3$, R$^4$, R$^5$, R$^6$ stands for —SO$_3^-$X$^+$ and
exactly one radical R$^2$, R$^3$, R$^4$, R$^5$, R$^6$ stands for a linear or branched alkyl radical containing 8 to 20 C atoms.

Particularly preferred representatives of the surfactants according to the invention are described in greater detail below. Surfactants which are preferred according to the invention are preferably also used in surfactant mixtures which are preferred according to the invention and detergents or cleaning agents which are preferred according to the invention. In this regard, the statements made regarding the surfactants according to the invention apply mutatis mutandis to the two latter-referenced subjects of the present invention. Surfactant mixtures according to the invention and detergents or cleaning agents which are preferred according to the invention are encompassed as preferred embodiments, even when they are not explicitly discussed.

In formula (I), R$^1$ stands for —H or a methyl group; the base body of the surfactants according to the invention is therefore derived from phenol or anisole. R$^1$ stands for —H in preferred surfactants according to the invention.

It is even further preferred when the surfactants according to the invention contain a hydroxy group and a methoxy group. In particularly preferred surfactants according to the invention, R$^1$ stands for —H, and at least one of the radicals R$^2$, R$^3$, R$^4$, R$^5$, R$^6$ stands for —O—CH$_3$.

Surfactants which are particularly preferred according to the invention therefore correspond to one of formulas (I-1), (I-2), or (I-3):

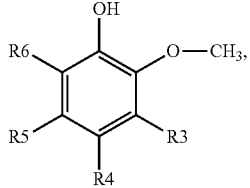
(I-1)

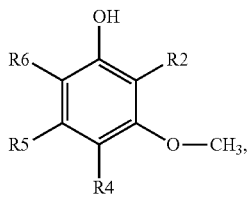
(I-2)

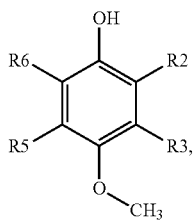
(I-3)

in which $R^2$, $R^3$, $R^4$, $R^5$, $R^6$ independently stand for —H, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —OH, —OCH$_3$, —OCH$_2$CH$_3$, —OCH$_2$CH$_2$CH$_3$, —OCH(CH$_3$)$_2$, a linear or branched alkyl radical containing 8 to 20 C atoms, or —SO$_3^-$X$^+$, X$^+$ stands for a monovalent cation or the nth part of an n-valent cation, with the condition that exactly one radical $R^2$, $R^3$, $R^4$, $R^5$, $R^6$ stands for —SO$_3^-$X$^+$ and exactly one radical $R^2$, $R^3$, $R^4$, $R^5$, $R^6$ stands for a linear or branched alkyl radical containing 8 to 20 C atoms.

Regardless of the selection of $R^1$ and regardless of whether at least one of the radicals $R^2$, $R^3$, $R^4$, $R^5$, $R^6$ stands for —O—CH$_3$, exactly one radical $R^2$, $R^3$, $R^4$, $R^5$, $R^6$ stands for —SO$_3^-$X$^+$, and exactly one radical $R^2$, $R^3$, $R^4$, $R^5$, $R^6$ stands for a linear or branched alkyl radical containing 8 to 20 C atoms.

Surfactants or surfactant mixtures or detergents or cleaning agents which are particularly preferred according to the invention are therefore characterized in that the surfactant(s) is/are selected from surfactants of formulas (Ia) and/or (Ib) and/or (Ic) and/or (Id)

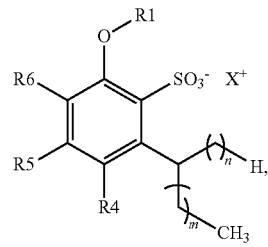
(Ia)

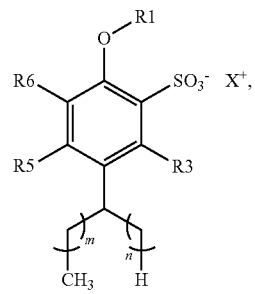
(Ib)

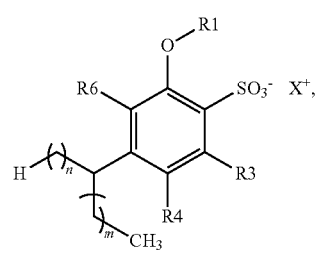
(Ic)

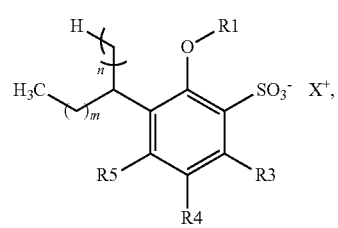
(Id)

in which $R^1$ stands for —H or —CH$_3$, $R^3$, $R^4$, $R^5$, $R^6$ independently stand for —H, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —OH, —OCH$_3$, —OCH$_2$CH$_3$, —OCH$_2$CH$_2$CH$_3$, —OCH(CH$_3$)$_2$, n, m independently stand for integers from 0 to 18, with the condition that the sum (m+n) stands for one of the numbers 6, 7, 8, 9, 10, 11, 12, 13, 14, 15, 16, 17, or 18.

In very particularly preferred representatives of formulas (Ia) or (Ib) or (Ic) or (Id), $R^1$ stands for —H, and at least one of the radicals $R^2$, $R^3$, $R^4$, $R^5$, $R^6$ stands for —O—CH$_3$. Particularly preferred surfactants may therefore be described by formulas (Ia-1) or (Ib-1) or (Ic-1) or (Id-1) or (Ia-2) or (Ib-2) or (Ic-2) or (Id-2) or (Ia-3) or (Ib-3) or (Ic-3) or (Id-3):

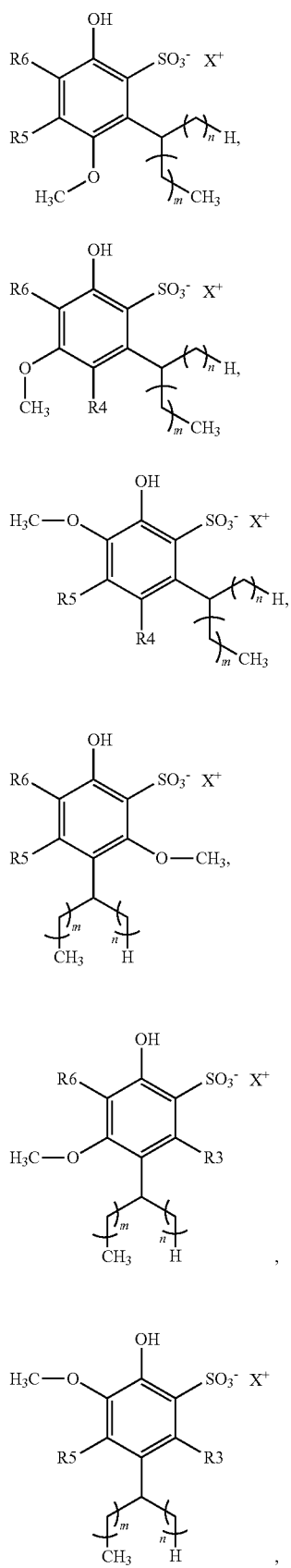
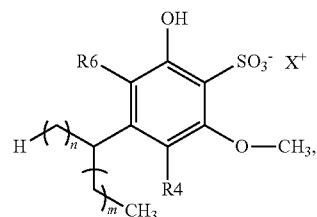
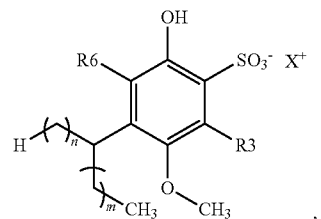
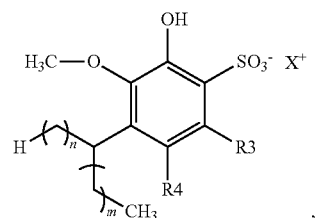
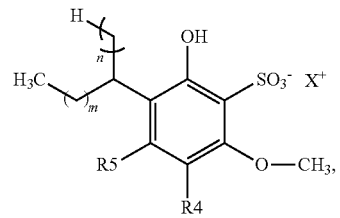
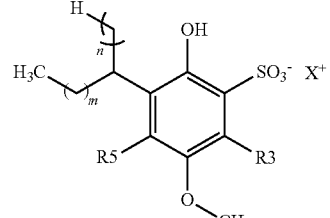
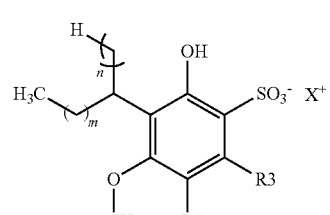
Regardless of whether at least one of the radicals $R^2$, $R^3$, $R^4$, $R^5$, $R^6$ stands for —O—CH$_3$, it is preferred when $R^2$, $R^3$, $R^4$, $R^5$, $R^6$ independently stand for —H, —CH$_3$, —CH$_2$CH$_3$, —CH$_2$CH$_2$CH$_3$, —CH(CH$_3$)$_2$. Molecules in which at least one of the radicals $R^2$, $R^3$, $R^4$, $R^5$, $R^6$ stands for —CH$_3$, —CH$_2$CH$_3$, —CH$_2$CH$_2$CH$_3$ are preferred according to the invention.

Particularly preferred surfactants may therefore be described by formulas (Ia-4) to (Ia-12) or (Ib-4) to (Ib-12) or (Ic-4) to (Ic-12) or (Id-4) to (Id-12):
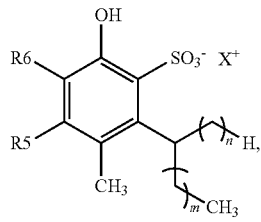
(Ia-4)
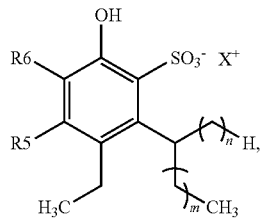
(Ia-5)
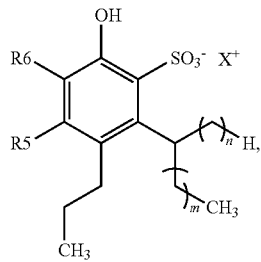
(Ia-6)
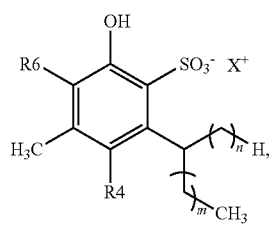
(Ia-7)
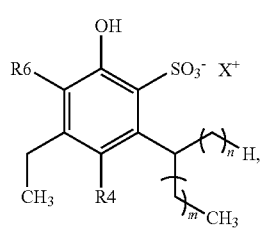
(Ia-8)
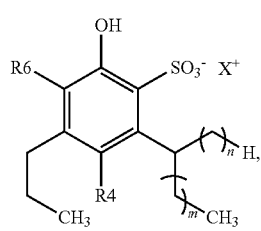
(Ia-9)
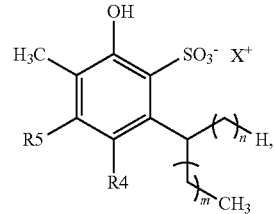
(Ia-10)
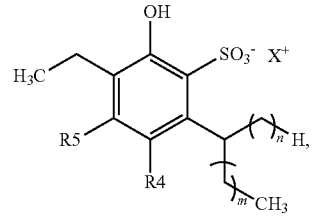
(Ia-11)
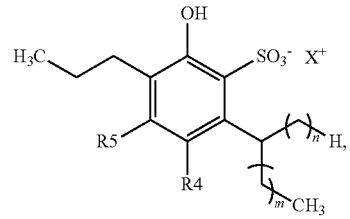
(Ia-12)
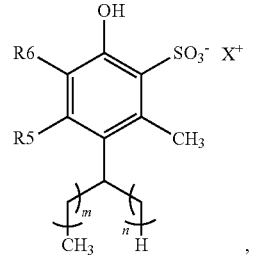
(Ib-4)
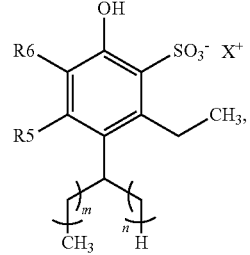
(Ib-5)
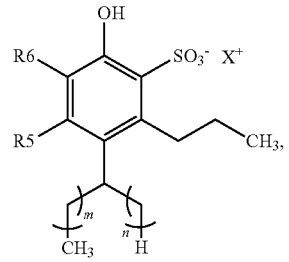
(Ib-6)

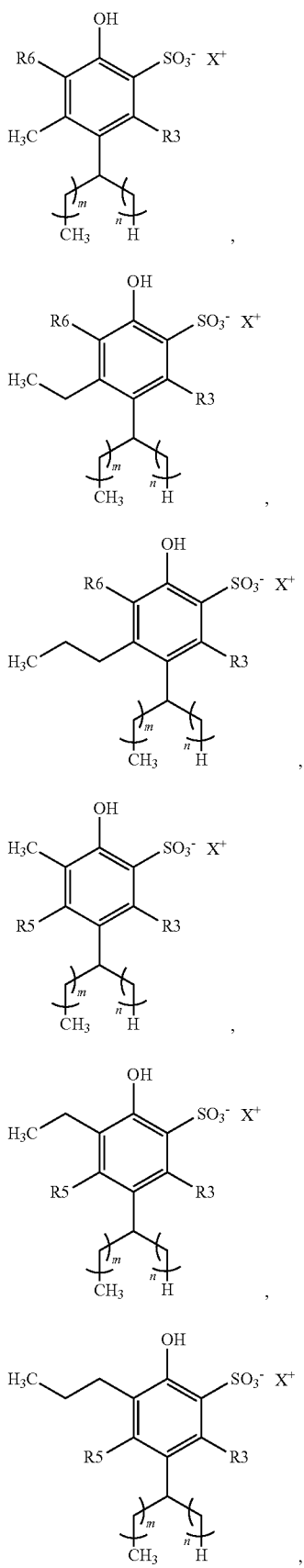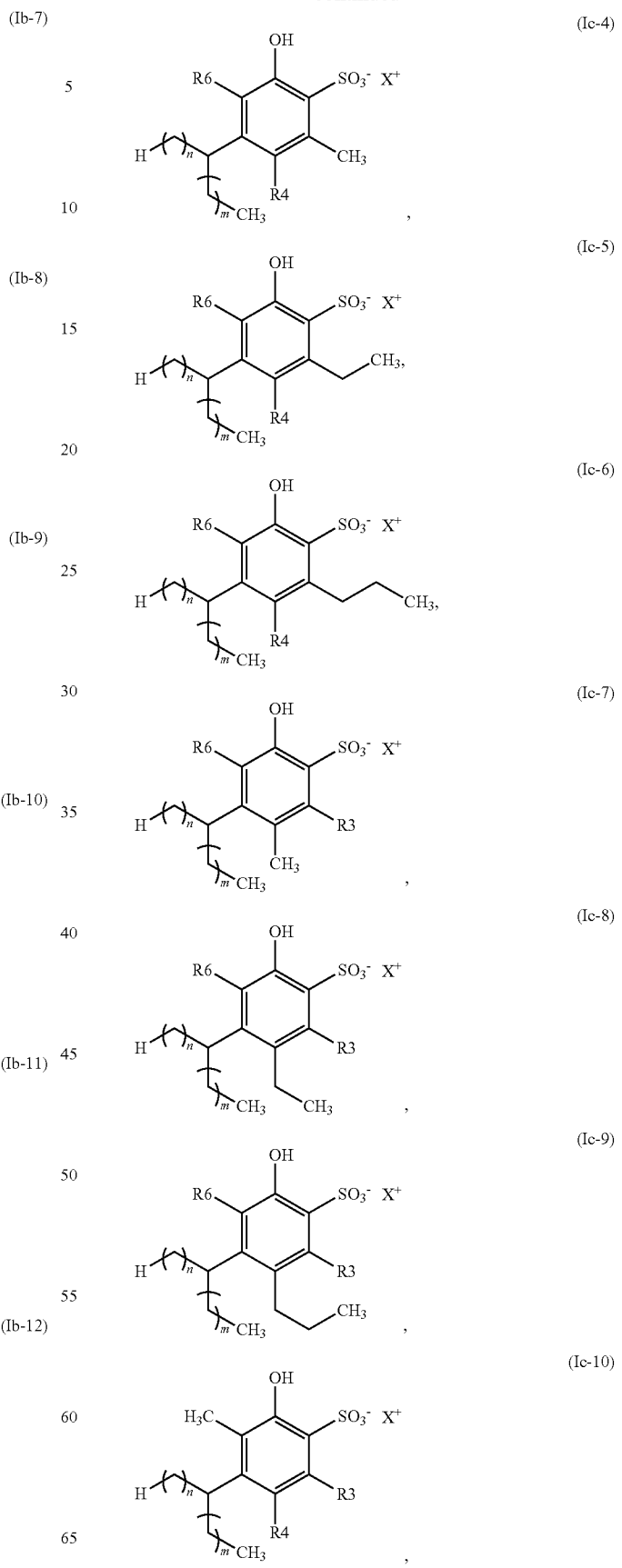

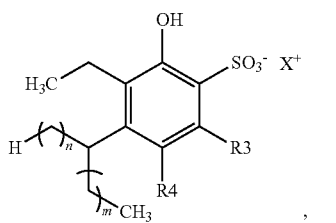 (Ic-11)

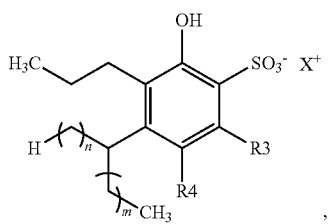 (Ic-12)

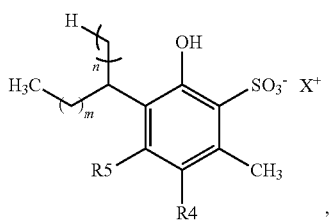 (Id-4)

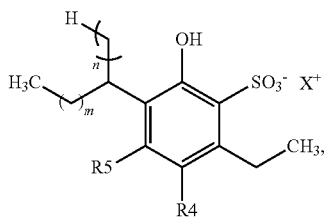 (Id-5)

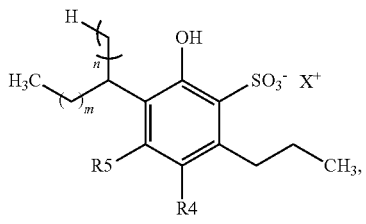 (Id-6)

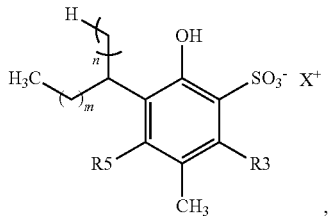 (Id-7)

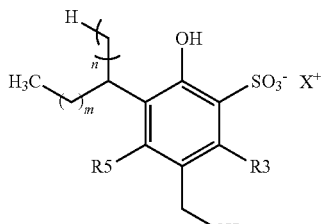 (Id-8)

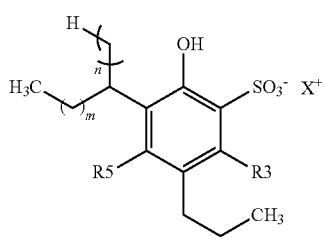 (Id-9)

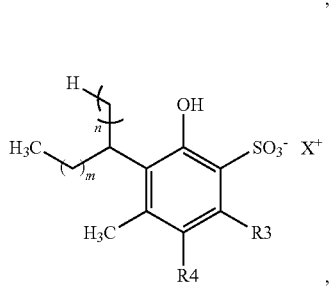 (Id-10)

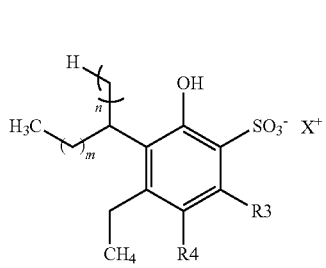 (Id-11)

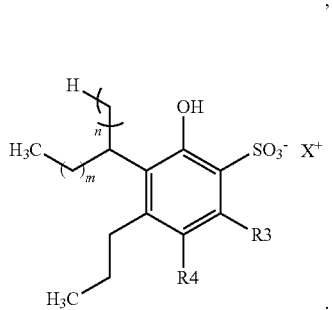 (Id-12)

In very particularly preferred representatives of formulas (Ia) or (Ib) or (Ic) or (Id), $R^1$ stands for —H, and at least one of the radicals $R^2$, $R^3$, $R^4$, $R^5$, $R^6$ stands for —O—CH$_3$, and at least one other of the radicals $R^2$, $R^3$, $R^4$, $R^5$, $R^6$ stands for —CH$_3$, —CH$_2$CH$_3$, —CH$_2$CH$_2$CH$_3$.

Particularly preferred surfactants may therefore be described by formulas (Ia-13) to (Ia-30) or (Ib-13) to (Ib-30) or (Ic-13) to (Ic-30) or (Id-13) to (Id-30):

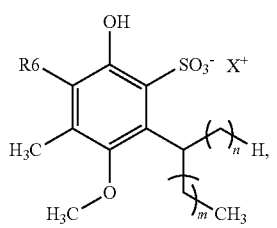 (Ia-13)

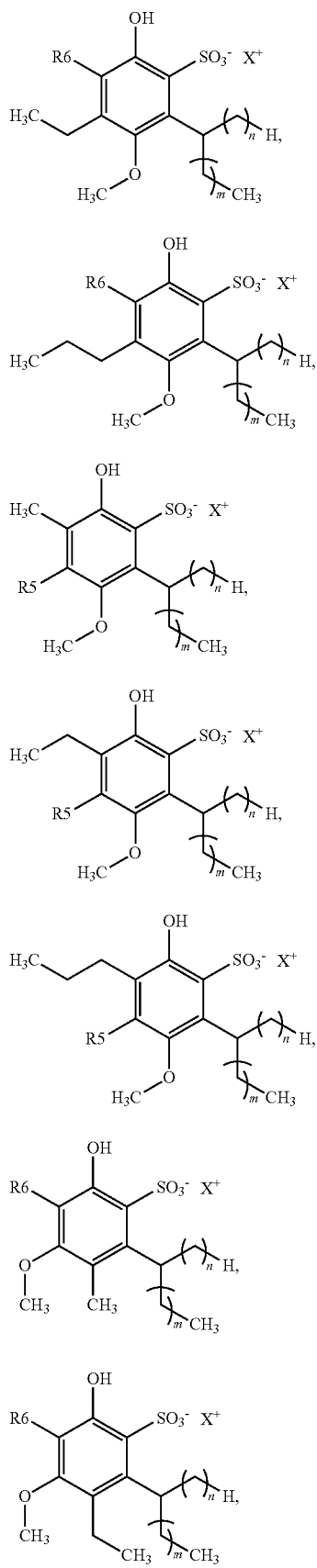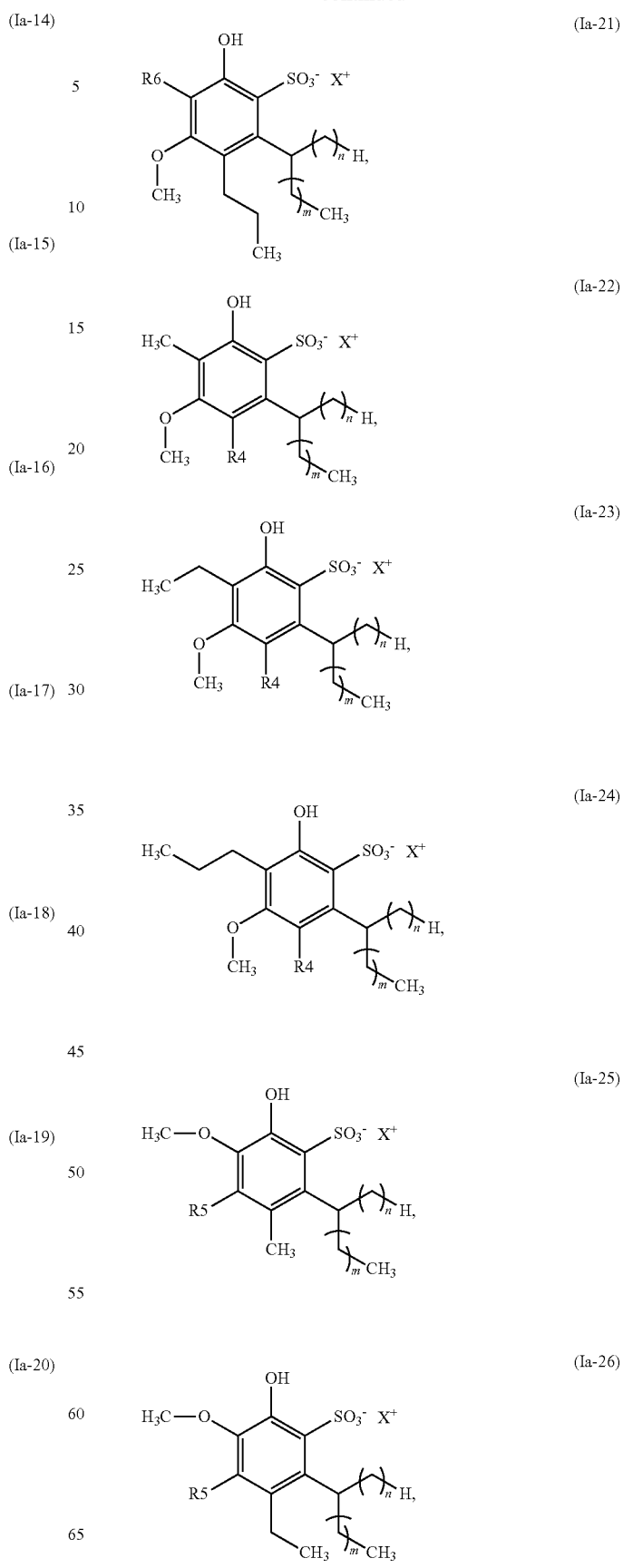

(Ia-27) 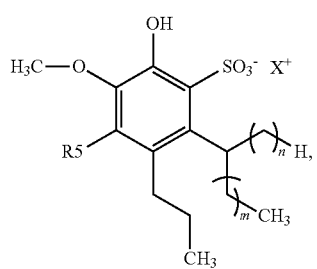
(Ia-28) 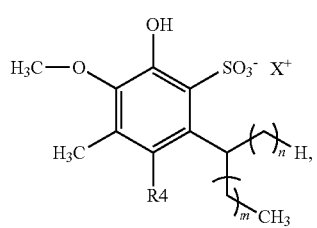
(Ia-29) 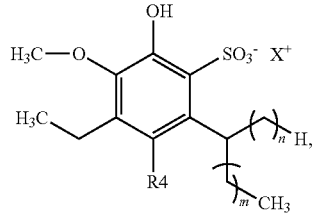
(Ia-30) 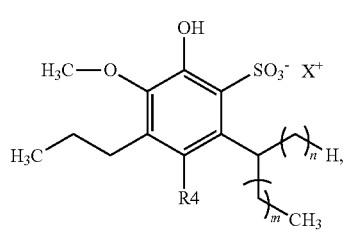
(Ib-13) 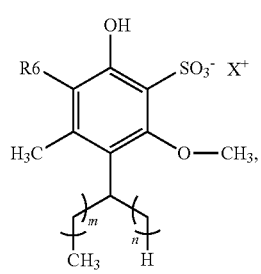
(Ib-14) 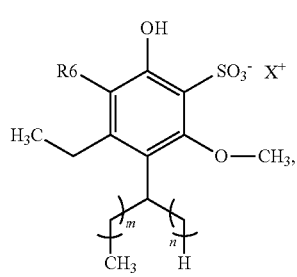
(Ib-15) 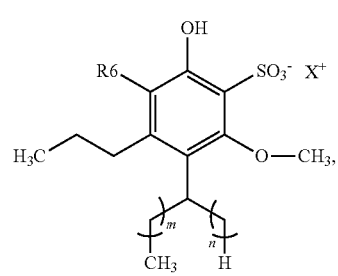
(Ib-16) 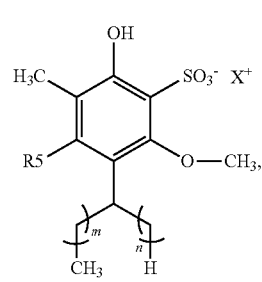
(Ib-17) 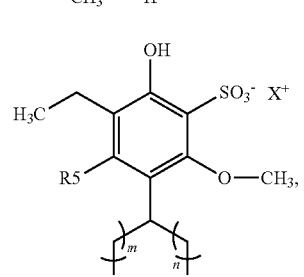
(Ib-18) 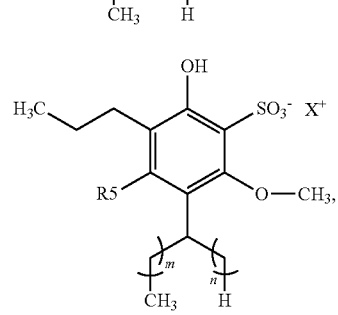
(Ib-19) 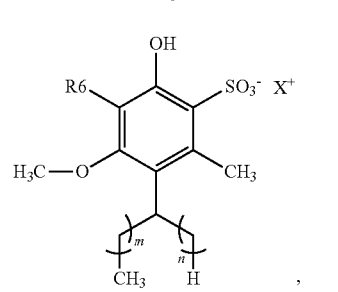
(Ib-20) 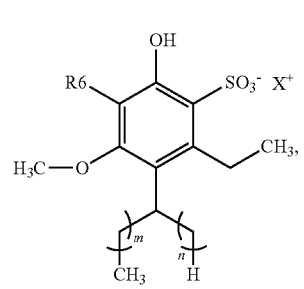

-continued
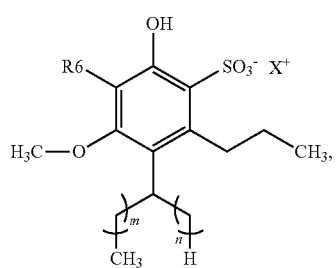
(Ib-21)
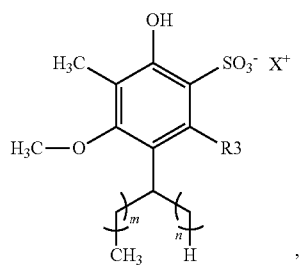
(Ib-22)
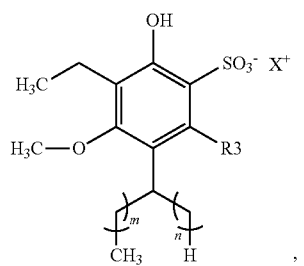
(Ib-23)
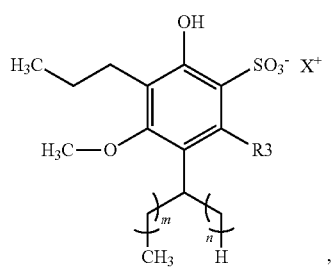
(Ib-24)
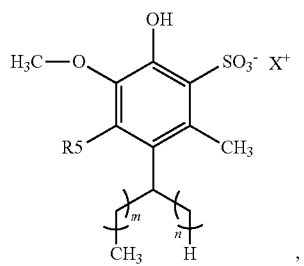
(Ib-25)
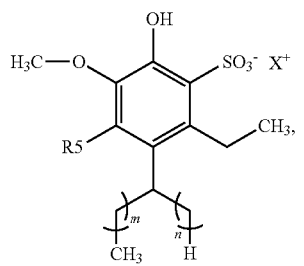
(Ib-26)
-continued
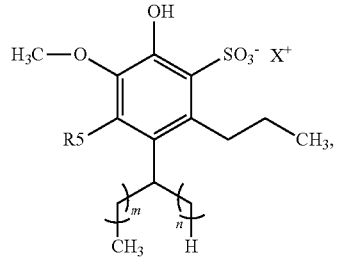
(Ib-27)
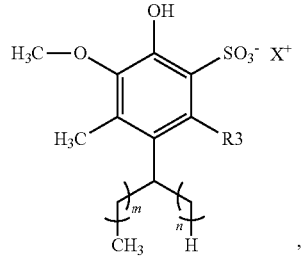
(Ib-28)
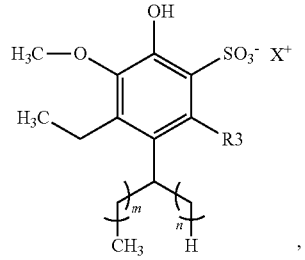
(Ib-29)
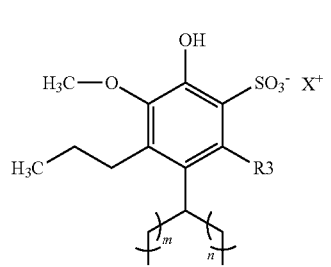
(Ib-30)
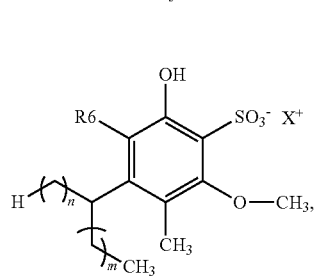
(Ic-13)
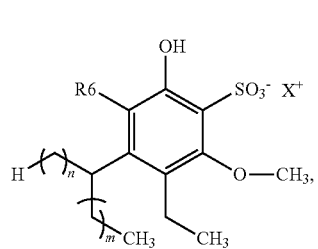
(Ic-14)

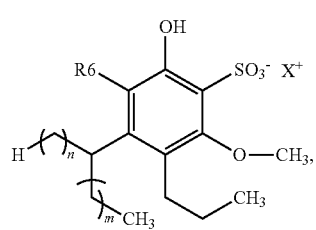 (Ic-15)
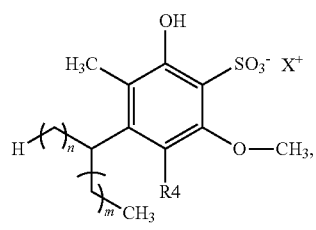 (Ic-16)
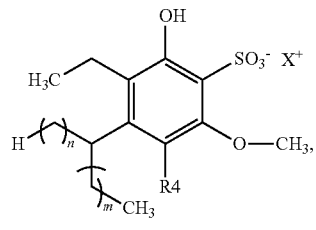 (Ic-17)
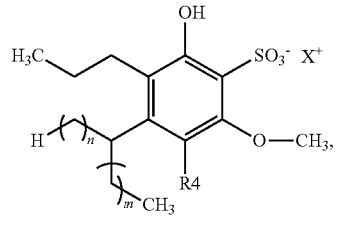 (Ic-18)
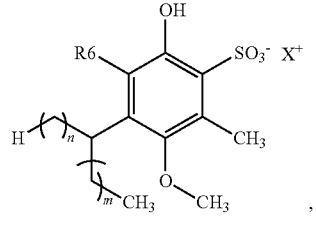 (Ic-19)
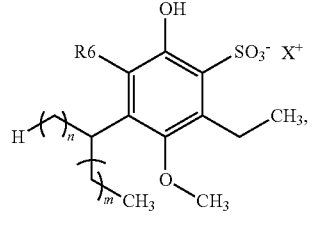 (Ic-20)
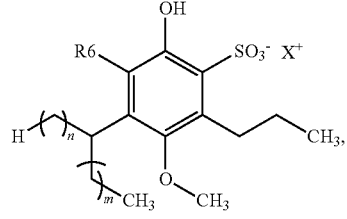 (Ic-21)
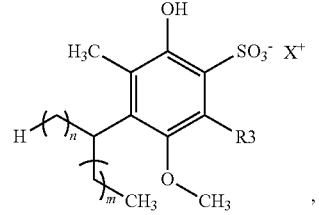 (Ic-22)
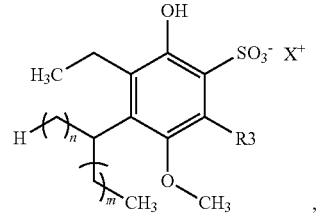 (Ic-23)
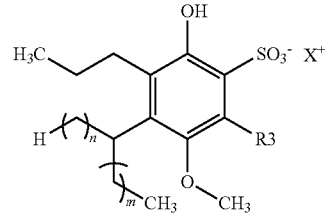 (Ic-24)
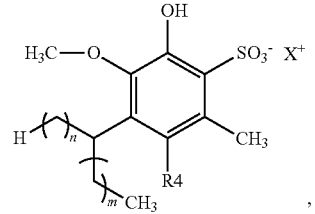 (Ic-25)
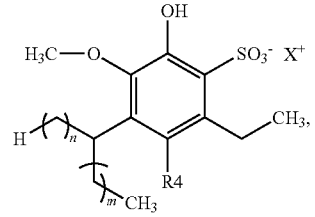 (Ic-26)
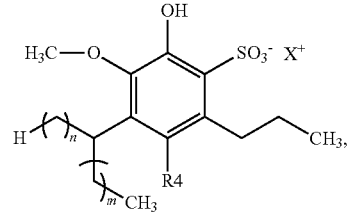 (Ic-27)
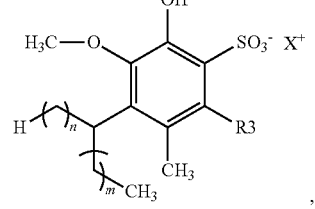 (Ic-28)

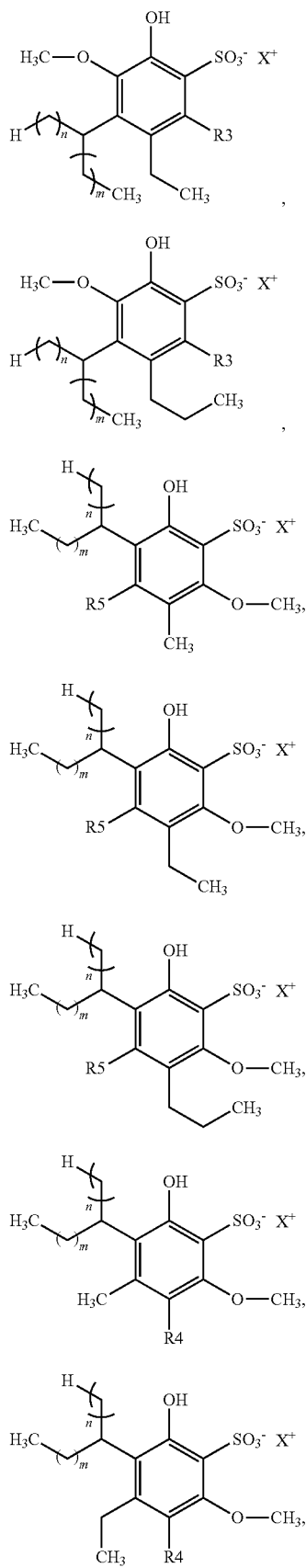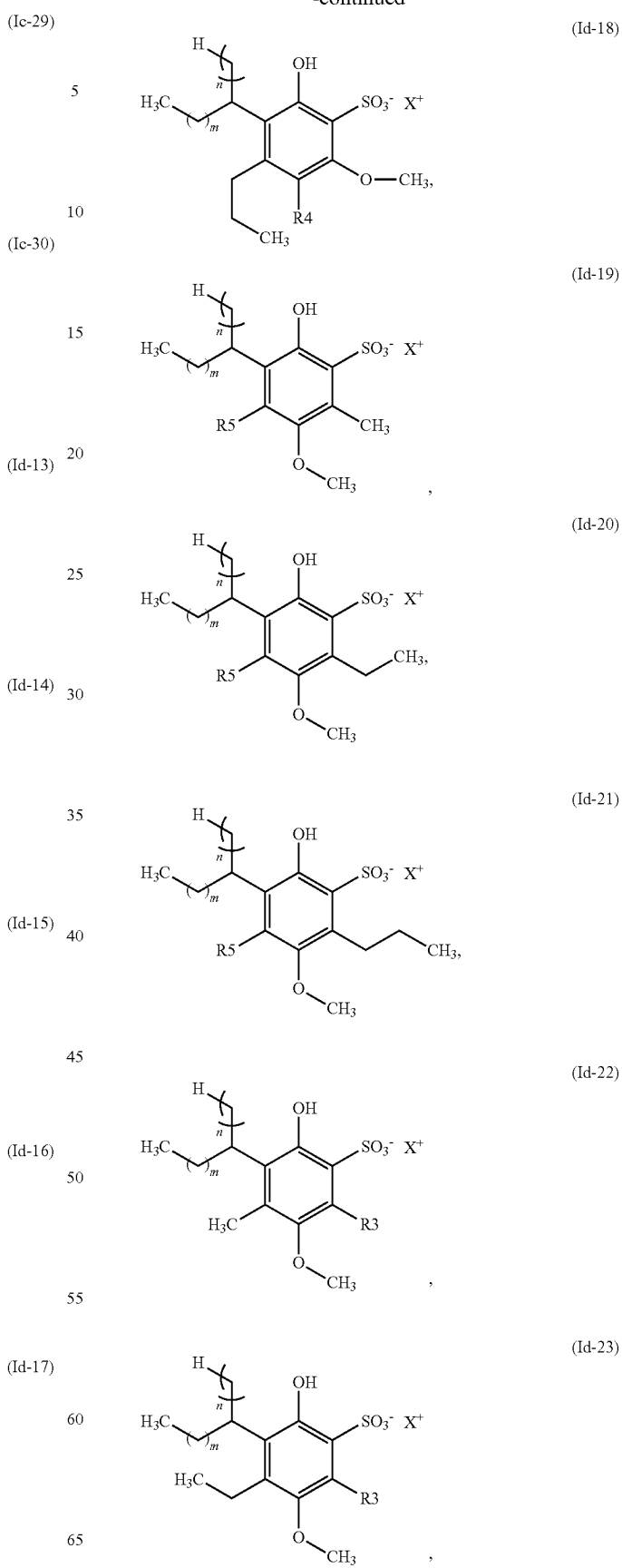

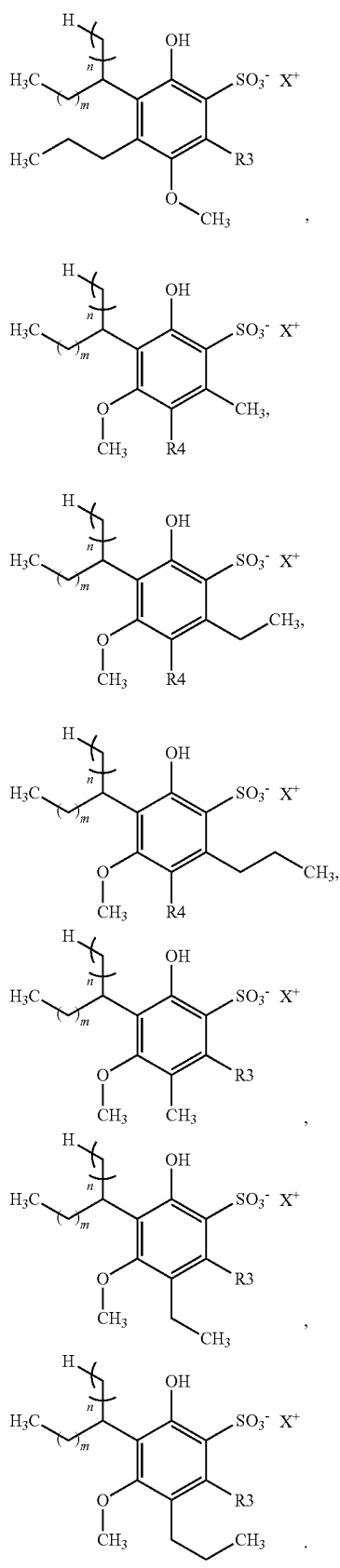
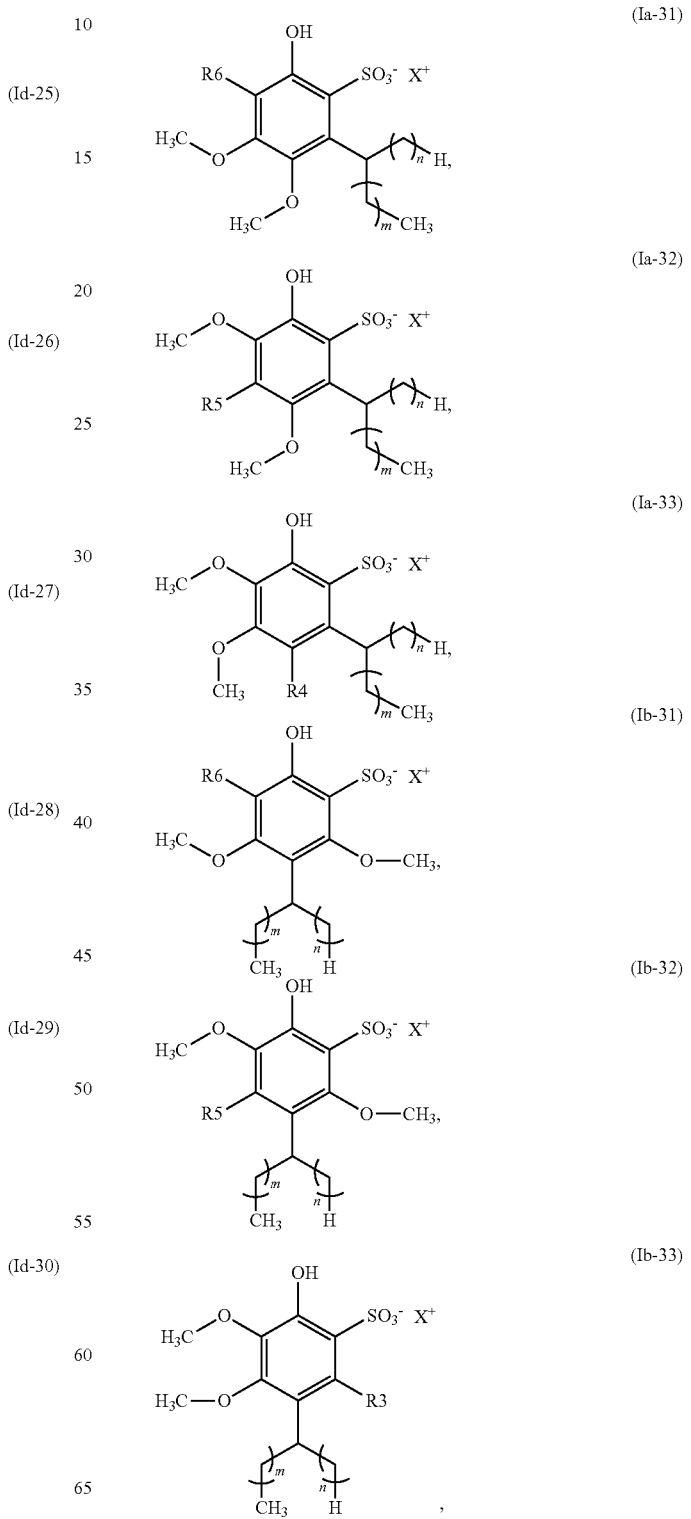
In likewise very particularly preferred representatives of formulas (Ia) or (Ib) or (Ic) or (Id), $R^1$ stands for —H, and at least two of the radicals $R^2$, $R^3$, $R^4$, $R^5$, $R^6$ stand for —O—$CH_3$.
Particularly preferred surfactants may therefore be described by formulas (Ia-31) to (Ia-33) or (Ib-31) to (Ib-33) or (Ic-31) to (Ic-33) or (Id-31) to (Id-33):

-continued

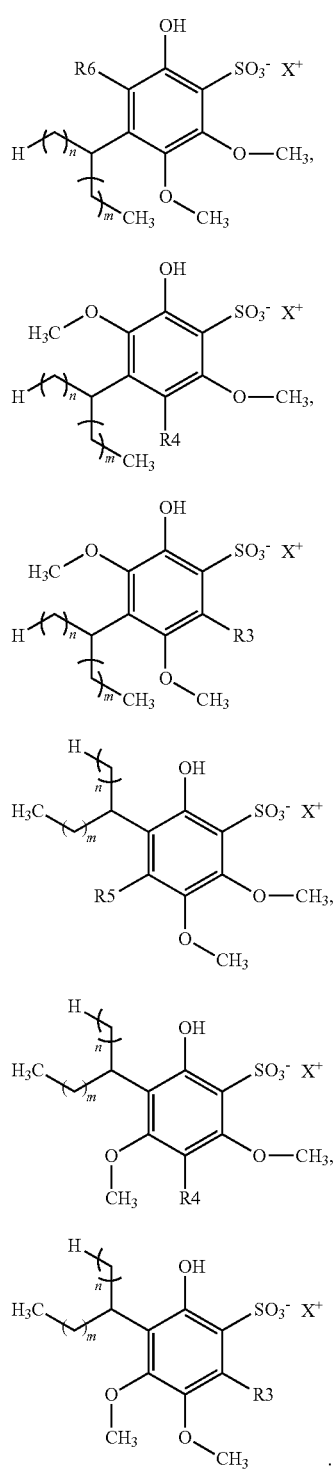

(Ic-31)
(Ic-32)
(Ic-33)
(Id-31)
(Id-32)
(Id-33)

In likewise very particularly preferred representatives of formulas (Ia) or (Ib) or (Ic) or (Id), $R^1$ stands for —H, and at least two of the radicals $R^2$, $R^3$, $R^4$, $R^5$, $R^6$ stand for —O—CH$_3$, and at least one other of the radicals $R^2$, $R^3$, $R^4$, $R^5$, $R^6$ stands for —CH$_3$, —CH$_2$CH$_3$, —CH$_2$CH$_2$CH$_3$.

Particularly preferred surfactants may therefore be described by formulas (Ia-37) to (Ia-54) or (Ib-37) to (Ib-54) or (Ic-37) to (Ic-54) or (Id-37) to (Id-54):

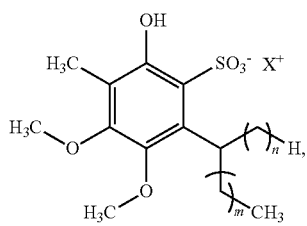
(Ia-37)

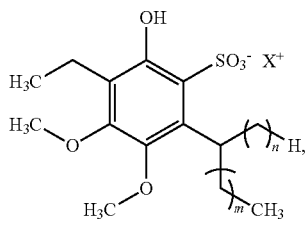
(Ia-38)

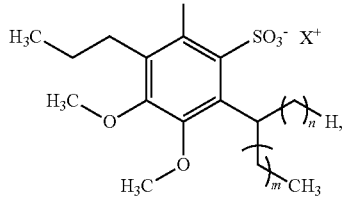
(Ia-39)

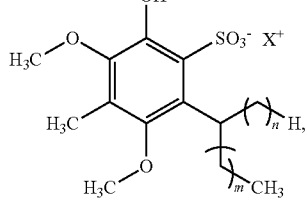
(Ia-40)

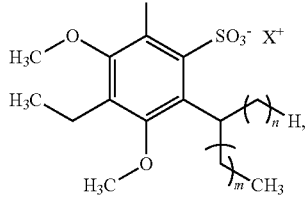
(Ia-41)

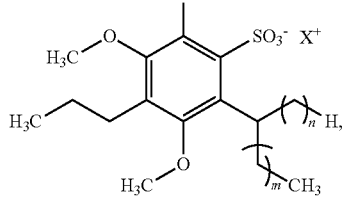
(Ia-42)

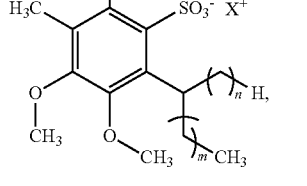
(Ia-43)

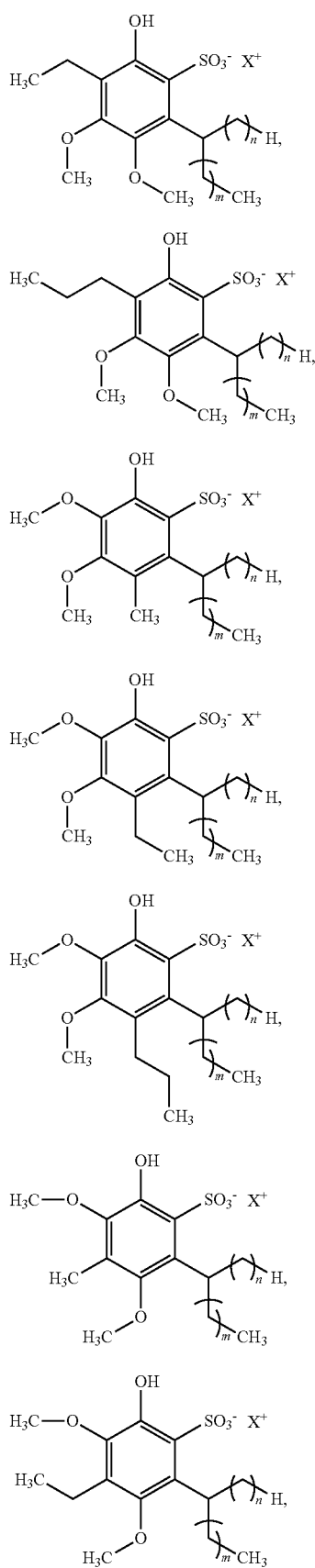
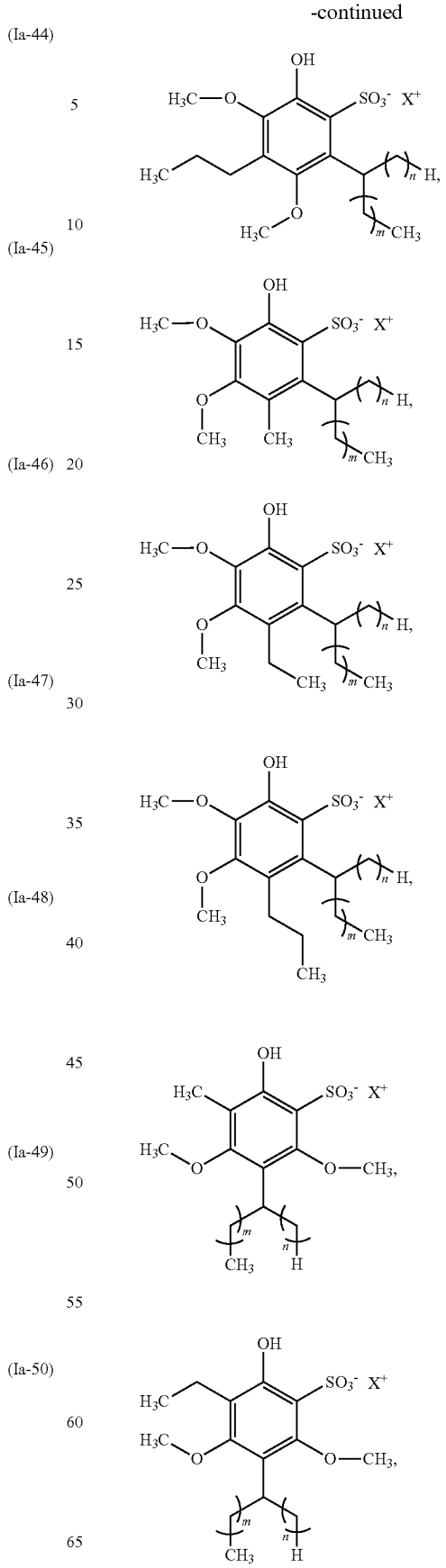

(Ib-39)
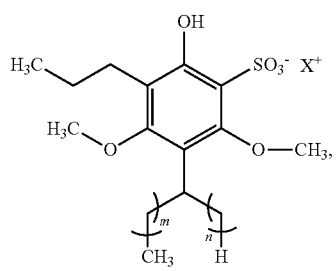
(Ib-40)
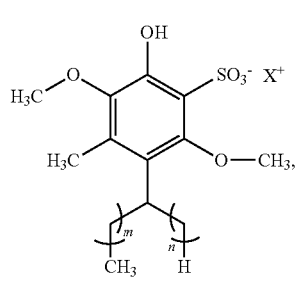
(Ib-41)
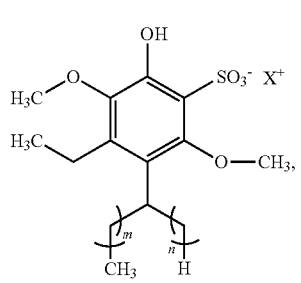
(Ib-42)
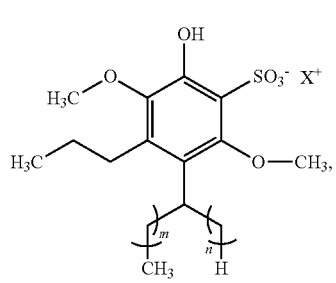
(Ib-43)
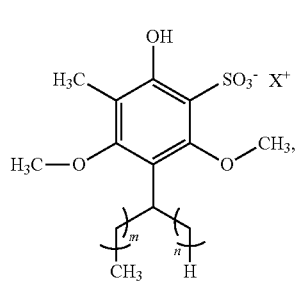
(Ib-44)
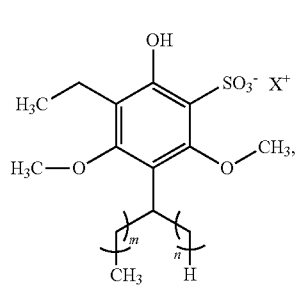
(Ib-45)
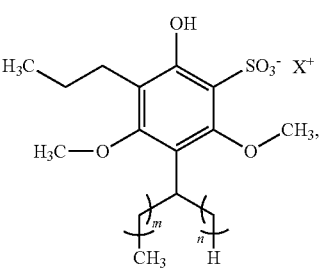
(Ib-46)
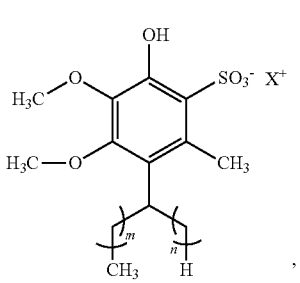
,
(Ib-47)
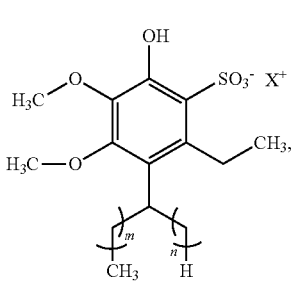
(Ib-48)
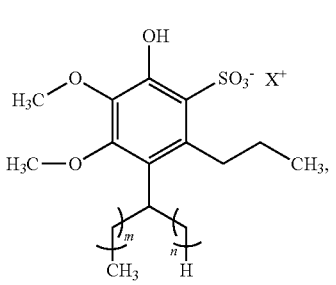
(Ib-49)
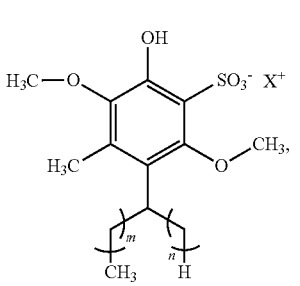
(Ib-50)
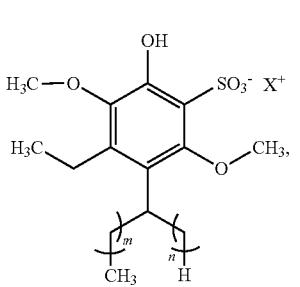

(Ib-51)
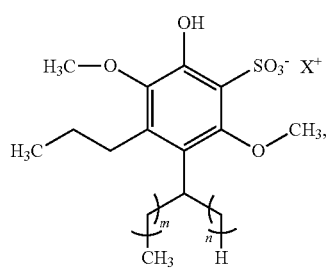
(Ib-52)
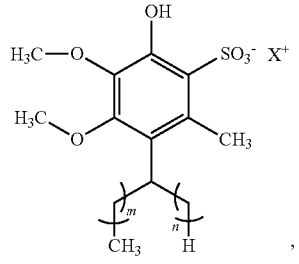
(Ib-53)
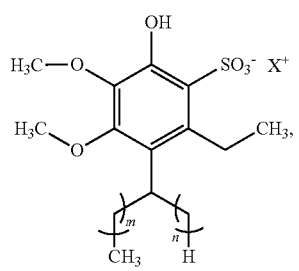
(Ib-54)
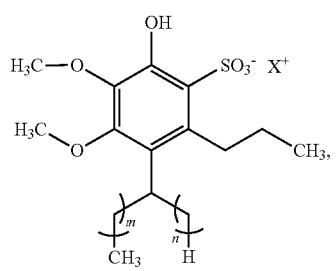
(Ic-37)
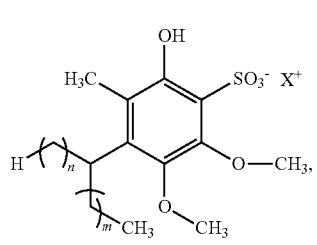
(Ic-38)
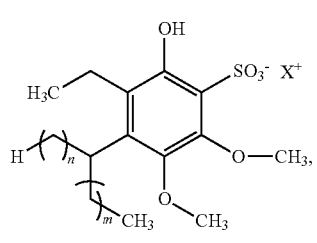
(Ic-39)
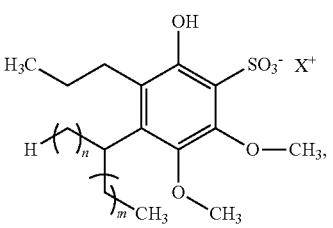
(Ic-40)
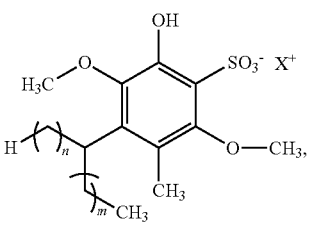
(Ic-41)
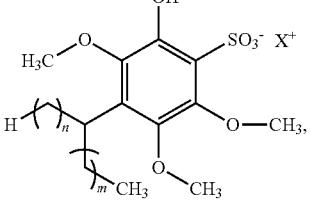
(Ic-42)
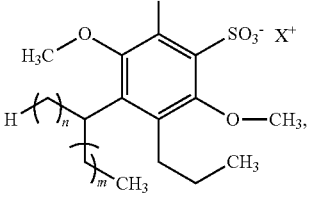
(Ic-43)
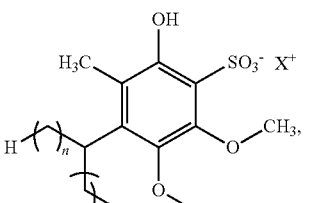
(Ic-44)
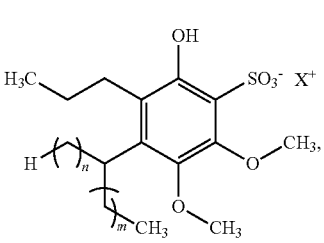
(Ic-45)

(Ic-46)
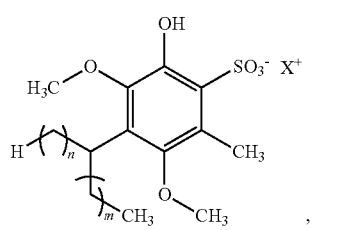
(Ic-47)
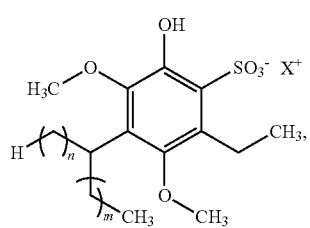
(Ic-48)
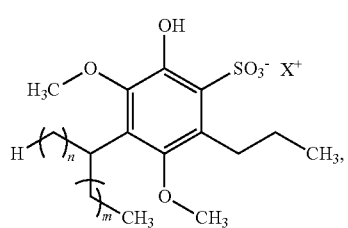
(Ic-49)
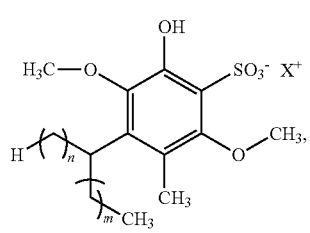
(Ic-50)
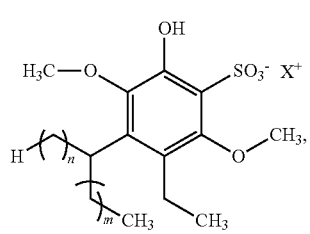
(Ic-51)
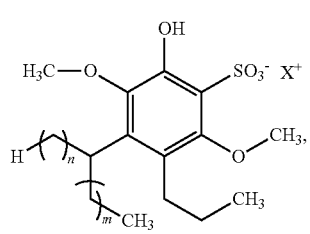
(Ic-52)
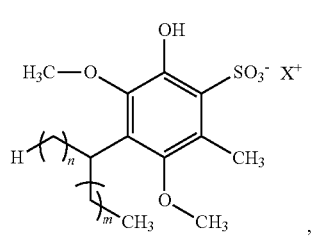
(Ic-53)
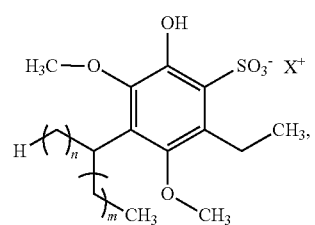
(Ic-54)
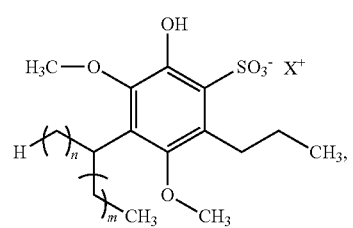
(Id-37)
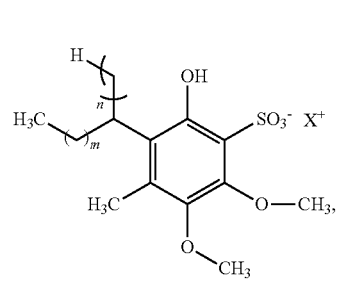
(Id-38)
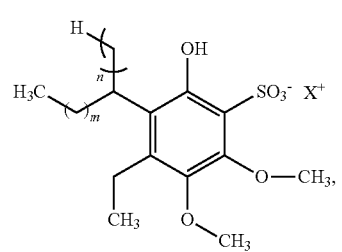
(Id-39)
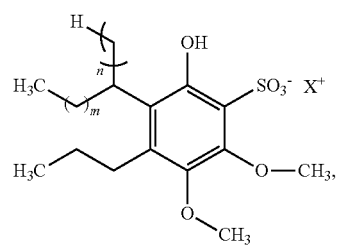
(Id-40)
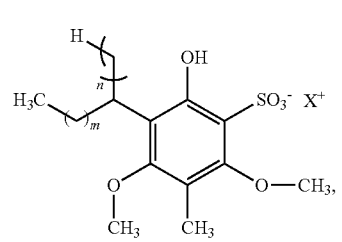

(Id-41) 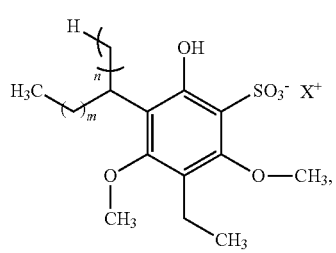
(Id-42) 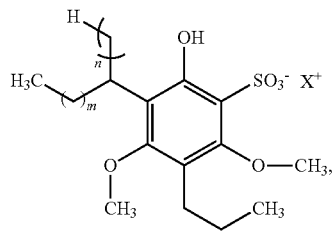
(Id-43) 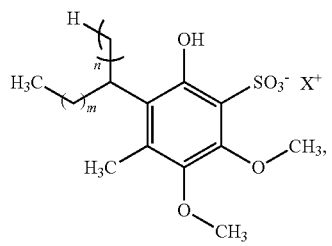
(Id-44) 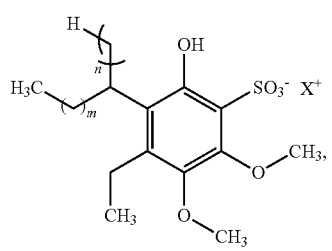
(Id-45) 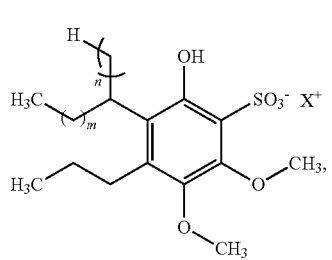
(Id-46) 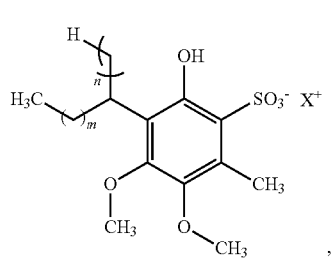
(Id-47) 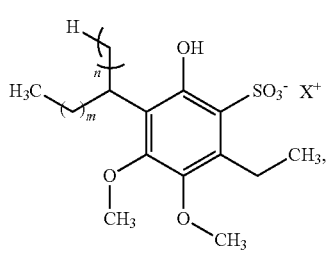
(Id-48) 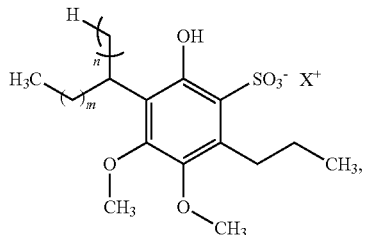
(Id-49) 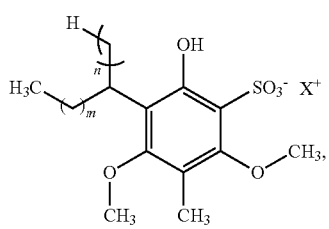
(Id-50) 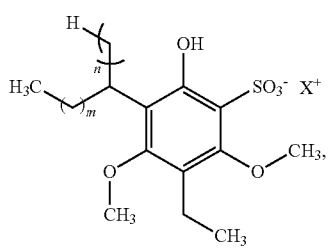
(Id-51) 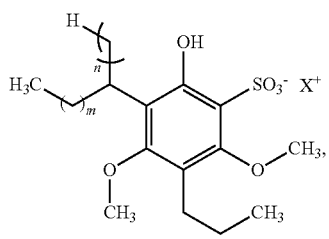
(Id-52) 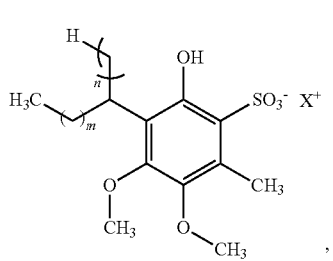

(Id-53)
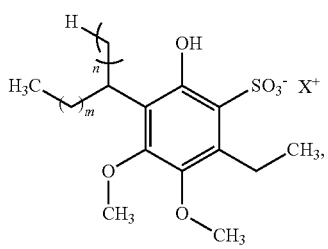

(Id-54)
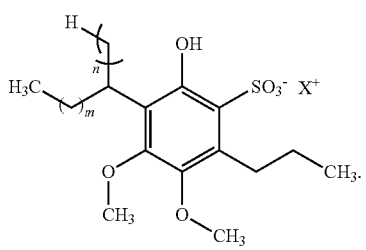

The —SO$_3^-$X$^+$ group may also be present in the meta-position relative to the —O—R$^1$ radical. Surfactants or surfactant mixtures or detergents or cleaning agents which are likewise particularly preferred according to the invention are therefore characterized in that the surfactant(s) is/are selected from surfactants of formulas (Ie) and/or (If) and/or (Ig) and/or (Ih):

(Ie)
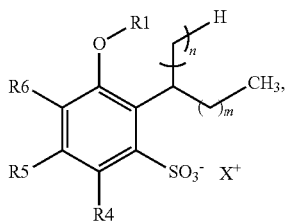

(If)
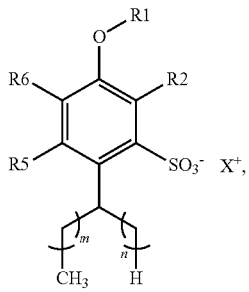

(Ig)
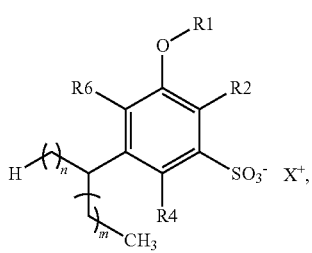

(Ih)
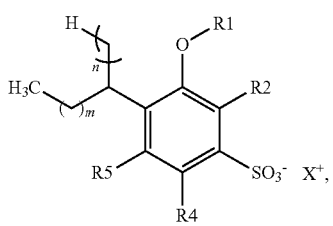

in which

R$^1$ stands for —H or —CH$_3$,

R$^2$, R$^4$, R$^5$, R$^6$ independently stand for —H, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —OH, —OCH$_3$, —OCH$_2$CH$_3$, —OCH$_2$CH$_2$CH$_3$, —OCH(CH$_3$)$_2$, n, m independently stand for integers from 0 to 18, with the condition that the sum (m+n) stands for one of the numbers 6, 7, 8, 9, 10, 11, 12, 13, 14, 15, 16, 17, or 18.

In very particularly preferred representatives of formulas (Ie) or (If) or (Ig) or (Ih), R$^1$ stands for —H, and at least one of the radicals R$^2$, R$^3$, R$^4$, R$^5$, R$^6$ stands for —O—CH$_3$. Particularly preferred surfactants may therefore be described by formulas (Ie-1) or (If-1) or (Ig-1) or (Ih-1) or (Ie-2) or (If-2) or (Ih-2) or (Ig-2) or (Ie-3) or (If-3) or (Ig-3) or (Ih-3):

(Ie-1)
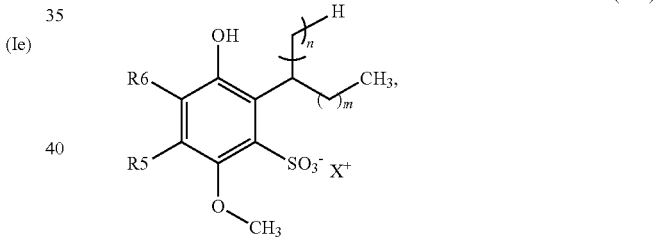

(Ie-2)
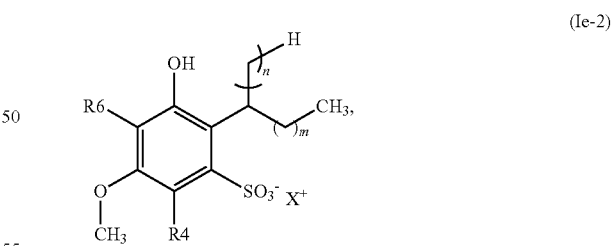

(Ie-3)
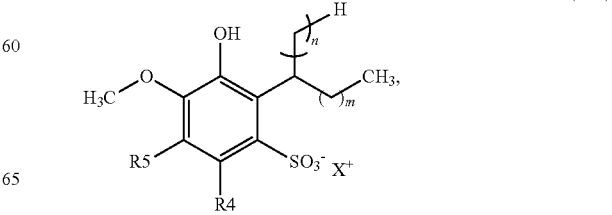

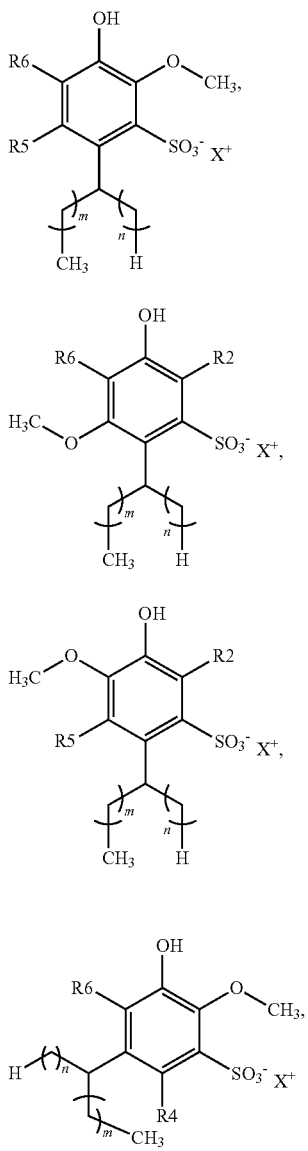

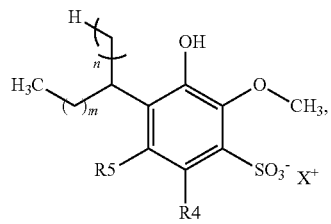

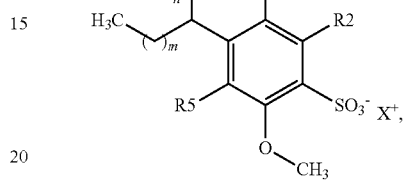

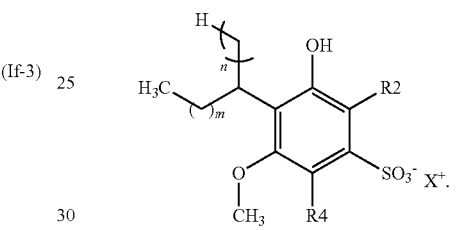

Regardless of whether at least one of the radicals $R^2$, $R^3$, $R^4$, $R^5$, $R^6$ stands for —O—$CH_3$, it is preferred when $R^2$, $R^3$, $R^4$, $R^5$, $R^6$ independently stand for —H, —$CH_3$, —$CH_2CH_3$, —$CH_2CH_2CH_3$, —$CH(CH_3)_2$. Molecules in which at least one of the radicals $R^2$, $R^3$, $R^4$, $R^5$, $R^6$ stands for —$CH_3$, —$CH_2CH_3$, —$CH_2CH_2CH_3$ are preferred according to the invention.

Particularly preferred surfactants may therefore be described by formulas (Ie-4) to (Ie-12) or (If-4) to (If-12) or (Ig-4) to (Ig-12) or (Ih-4) to (Ih-12):

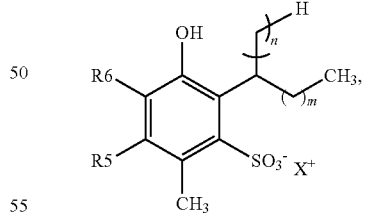

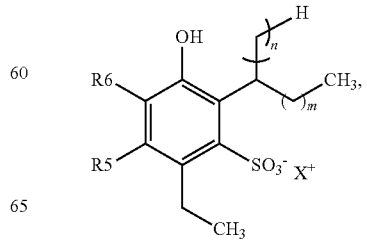

(Ie-6)
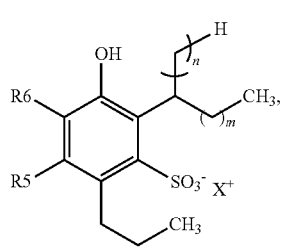
(Ie-7)
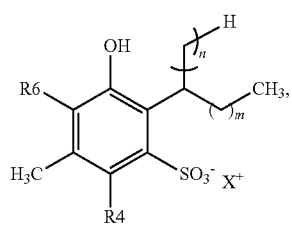
(Ie-8)
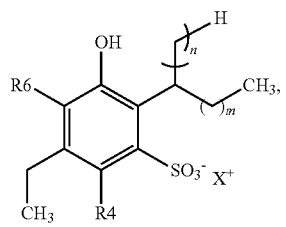
(Ie-9)
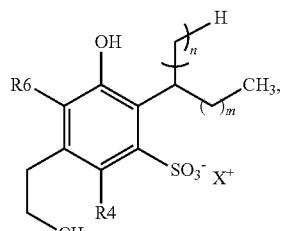
(Ie-10)
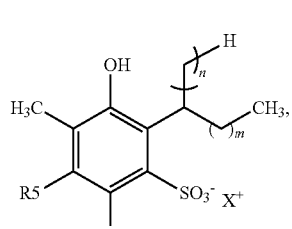
(Ie-11)
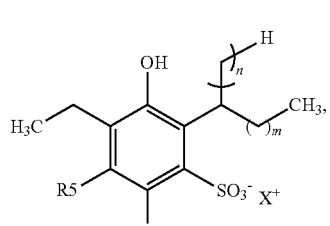
(Ie-12)
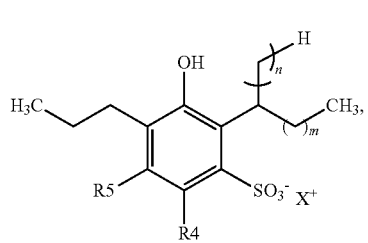
(If-4)
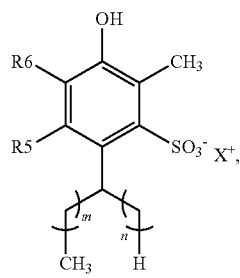
(If-5)
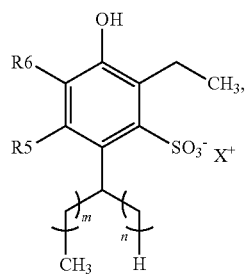
(If-6)
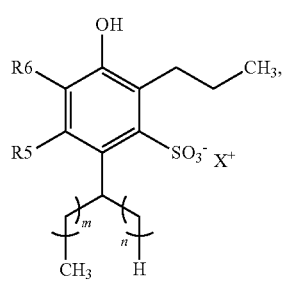
(If-7)
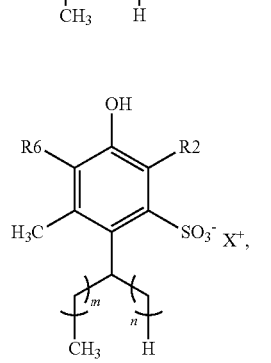
(If-8)
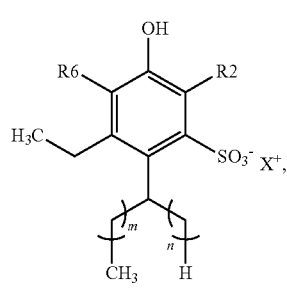

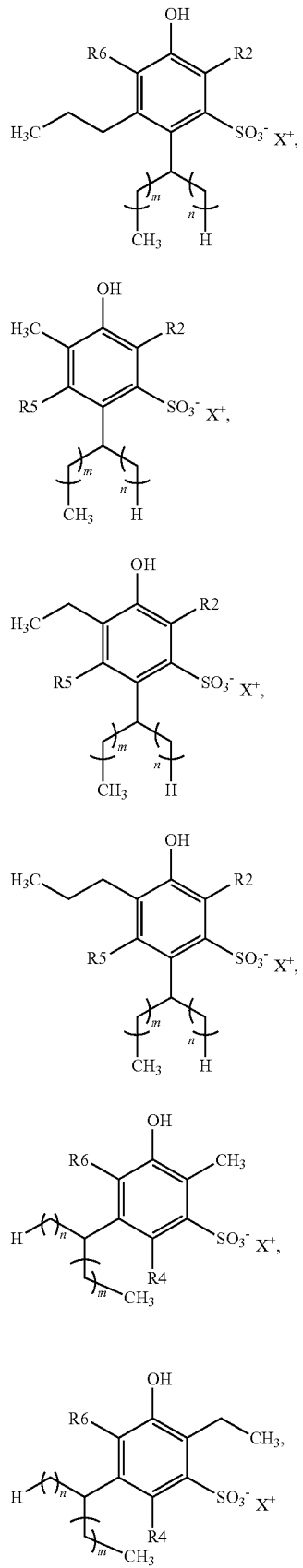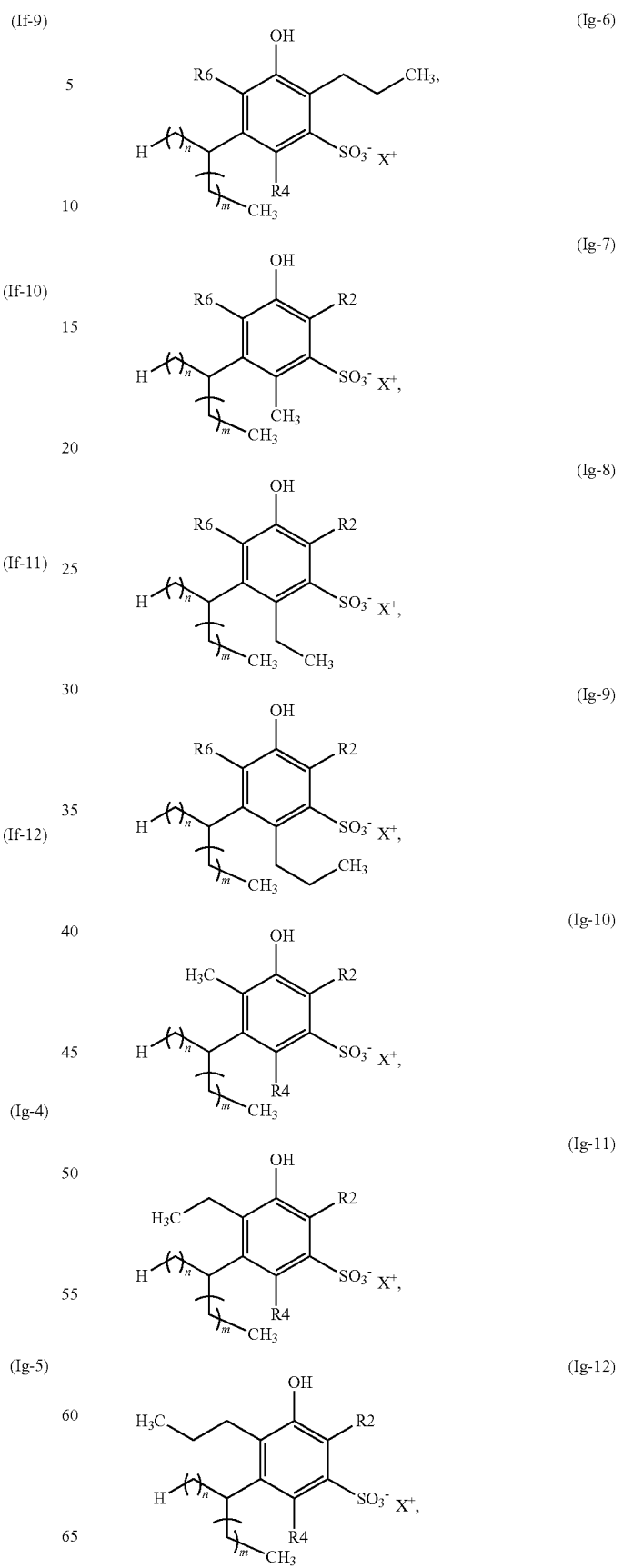

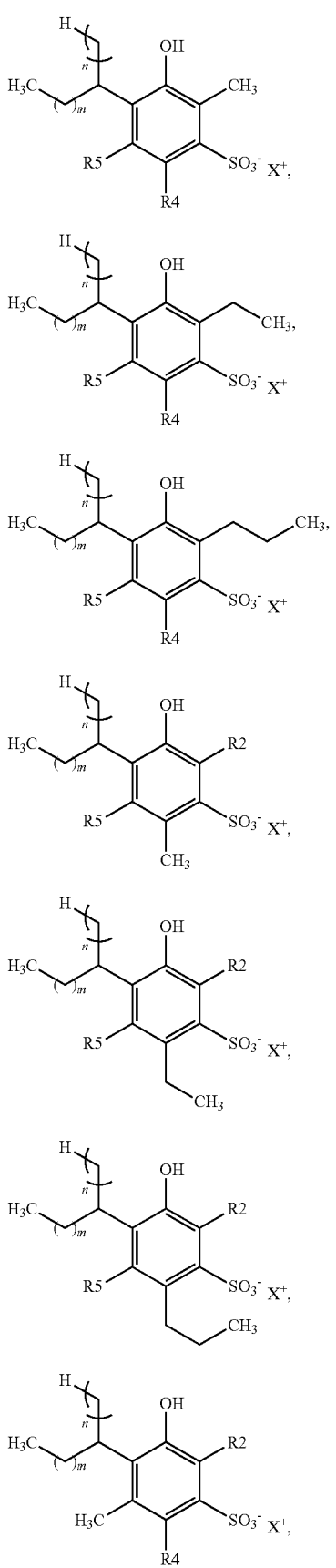

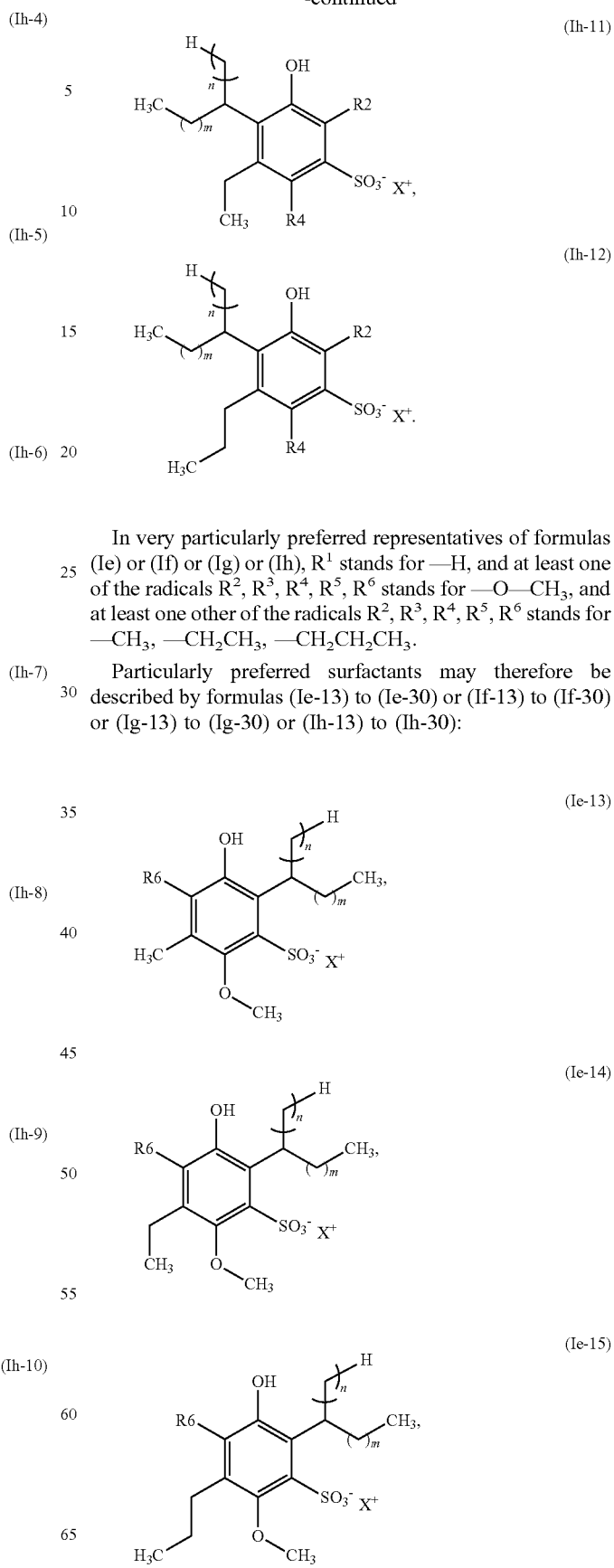

In very particularly preferred representatives of formulas (Ie) or (If) or (Ig) or (Ih), $R^1$ stands for —H, and at least one of the radicals $R^2$, $R^3$, $R^4$, $R^5$, $R^6$ stands for —O—$CH_3$, and at least one other of the radicals $R^2$, $R^3$, $R^4$, $R^5$, $R^6$ stands for —$CH_3$, —$CH_2CH_3$, —$CH_2CH_2CH_3$.

Particularly preferred surfactants may therefore be described by formulas (Ie-13) to (Ie-30) or (If-13) to (If-30) or (Ig-13) to (Ig-30) or (Ih-13) to (Ih-30):

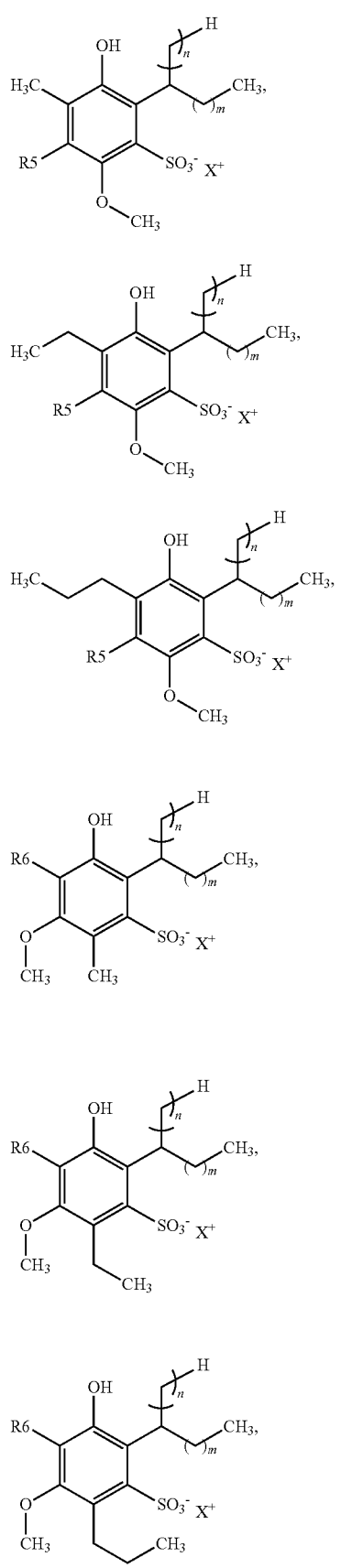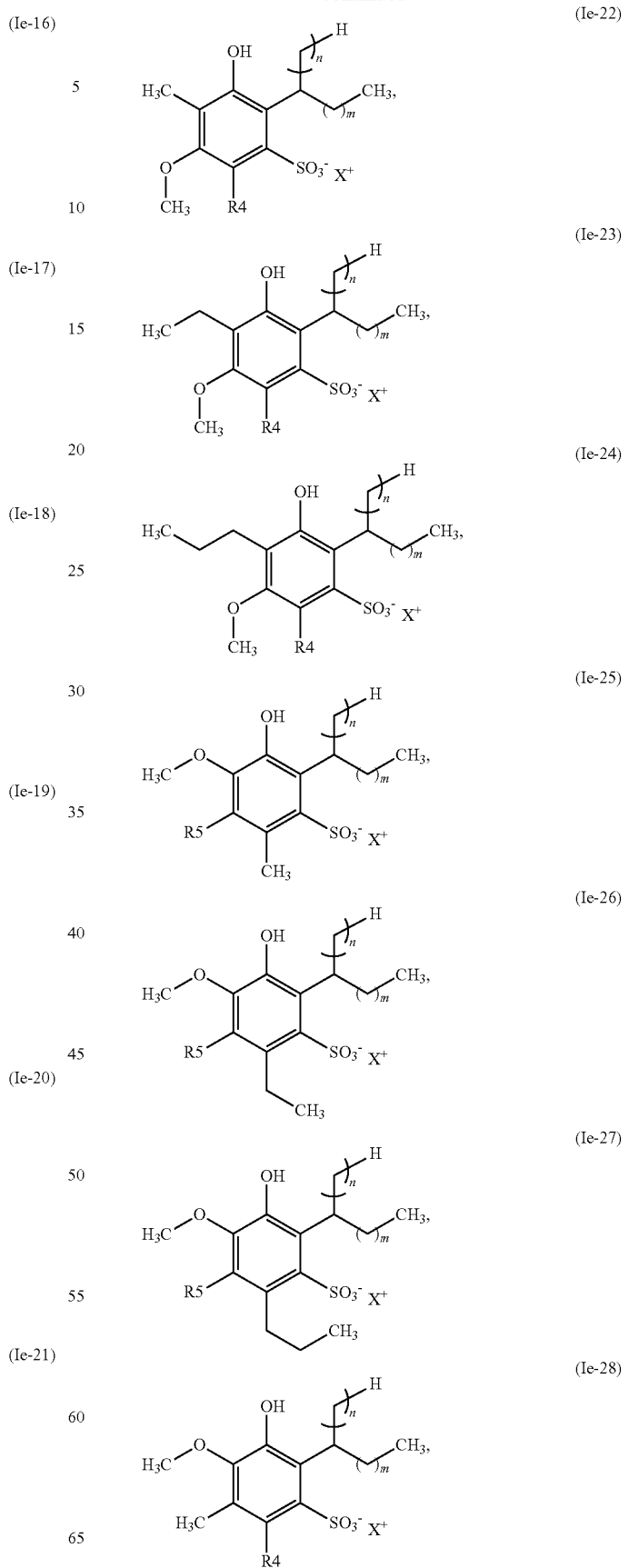

(Ie-29) 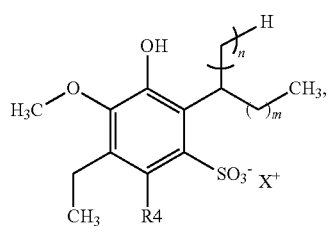
(Ie-30) 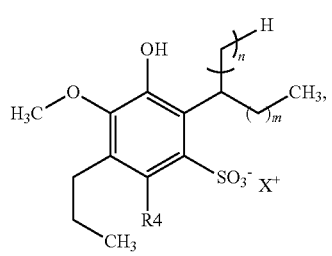
(If-13) 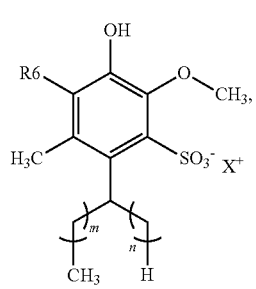
(If-14) 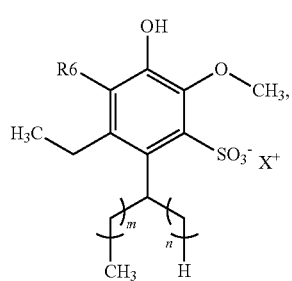
(If-15) 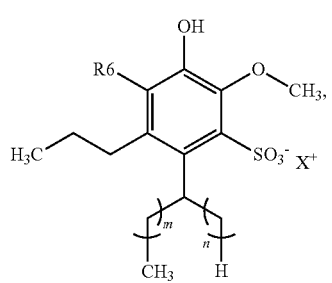
(If-16) 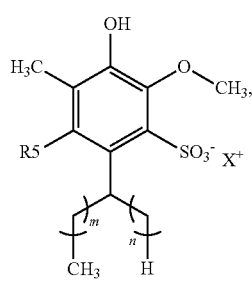
(If-17) 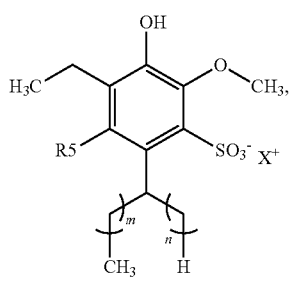
(If-18) 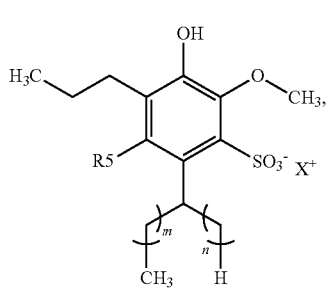
(If-19) 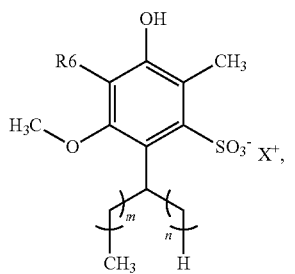
(If-20) 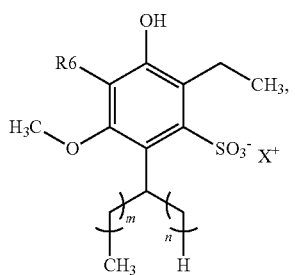
(If-21) 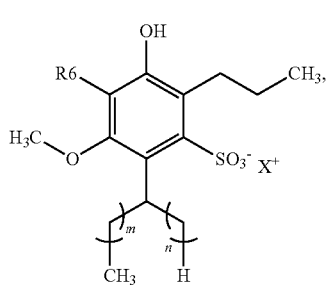

(If-22) 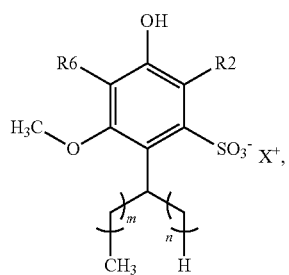
(If-23) 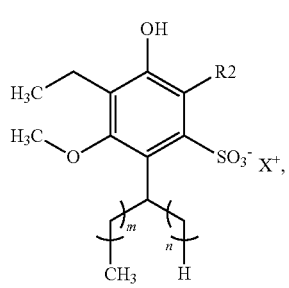
(If-24) 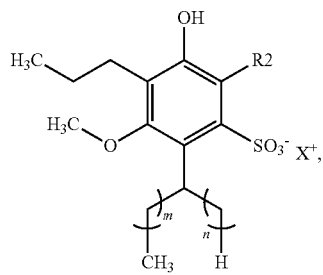
(If-25) 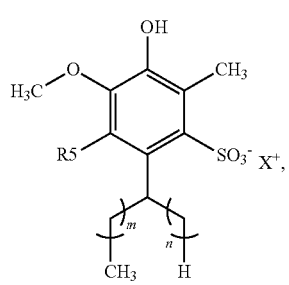
(If-26) 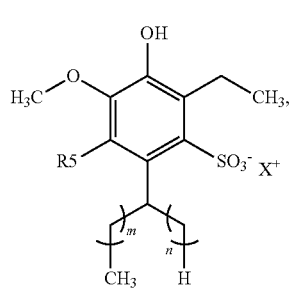
(If-27) 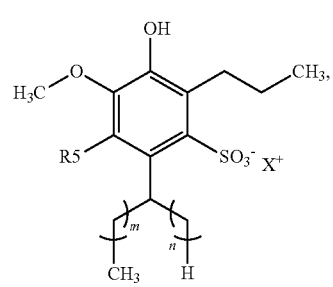
(If-28) 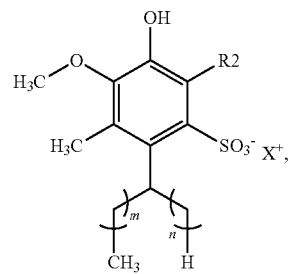
(If-29) 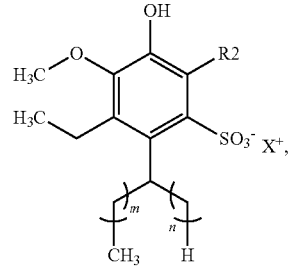
(If-30) 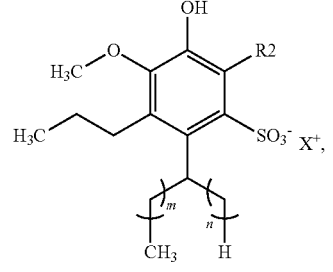
(Ig-13) 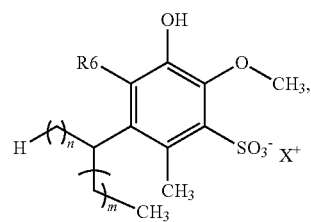
(Ig-14) 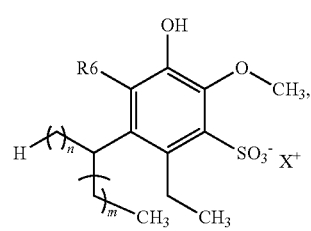

(Ig-15)
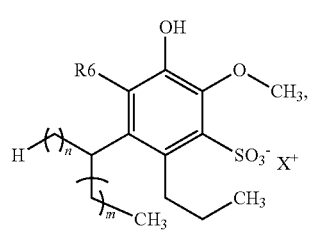
(Ig-16)
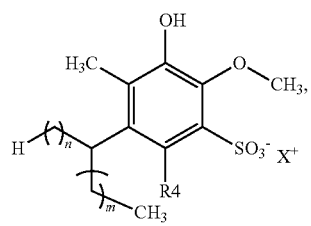
(Ig-17)
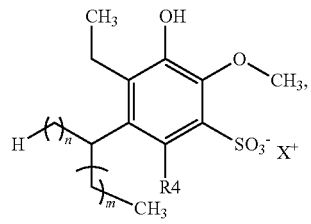
(Ig-18)
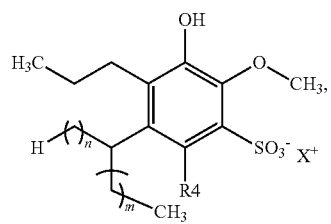
(Ig-19)
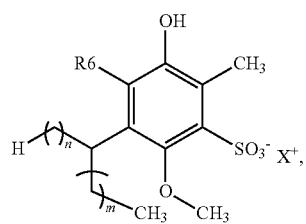
(Ig-20)
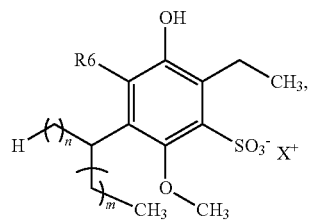
(Ig-21)
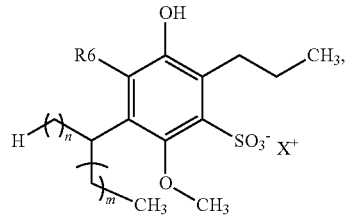
(Ig-22)
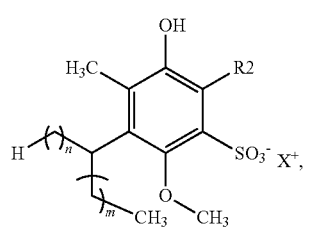
(Ig-23)
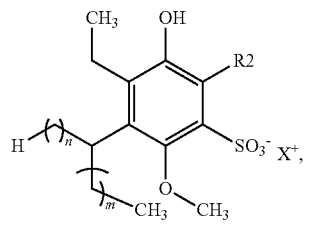
(Ig-24)
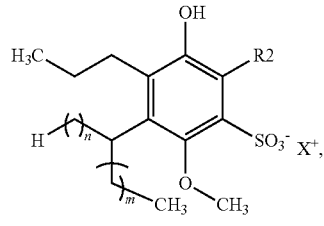
(Ig-25)
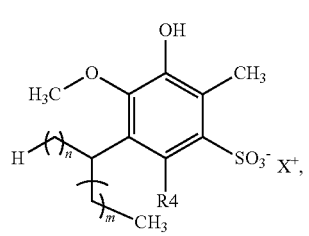
(Ig-26)
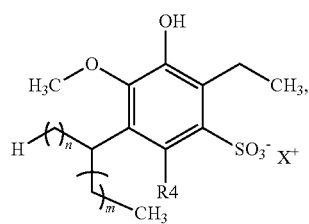
(Ig-27)
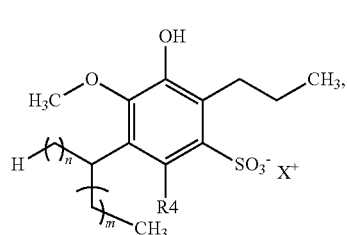
(Ig-28)
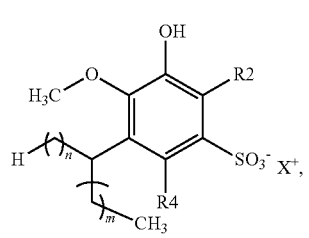

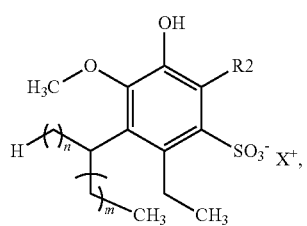
(Ig-29)
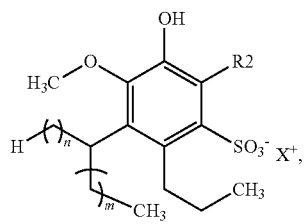
(Ig-30)
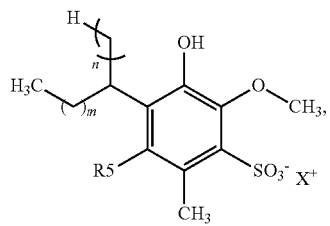
(Ih-13)
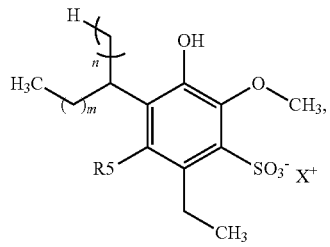
(Ih-14)
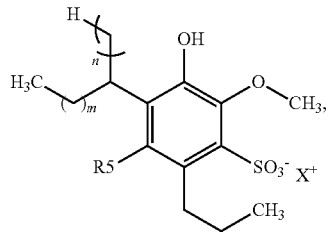
(Ih-15)
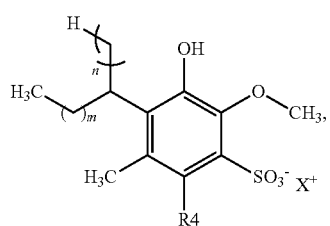
(Ih-16)
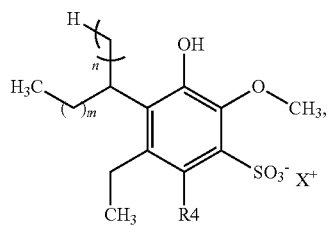
(Ih-17)
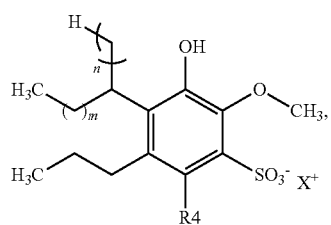
(Ih-18)
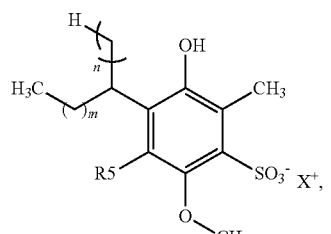
(Ih-19)
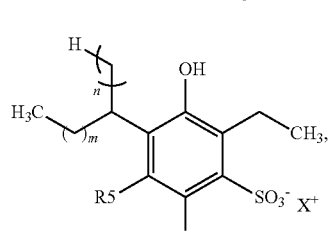
(Ih-20)
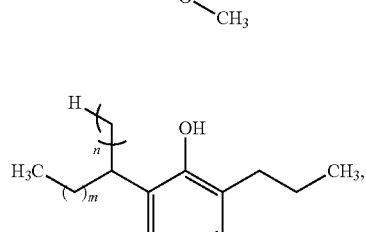
(Ih-21)
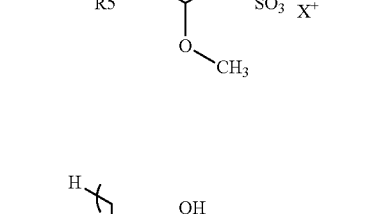
(Ih-22)
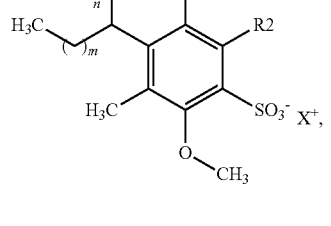
(Ih-22)
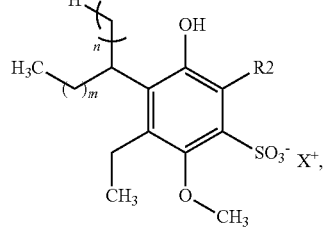
(Ih-23)

In likewise very particularly preferred representatives of formulas (Ie) or (If) or (Ig) or (Ih), $R^1$ stands for —H, and at least two of the radicals $R^2$, $R^3$, $R^4$, $R^5$, $R^6$ stand for —O—CH$_3$.

Particularly preferred surfactants may therefore be described by formulas (Ie-31) to (Ie-33) or (If-31) to (If-33) or (Ig-31) to (Ig-33) or (Ih-31) to (Ih-33):

(If-32) 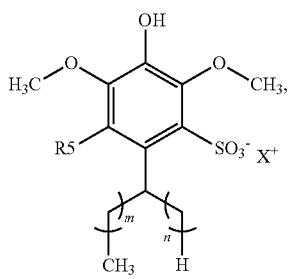

(If-33) 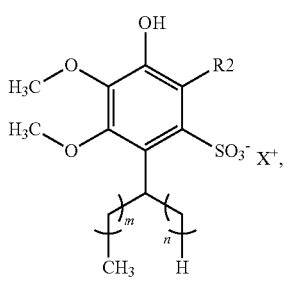

(Ig-31) 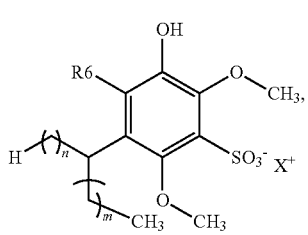

(Ig-32) 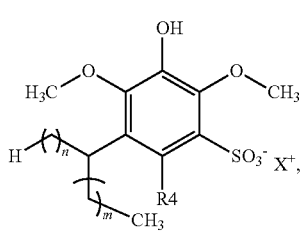

(Ig-33) 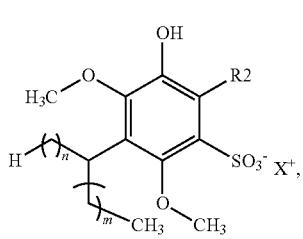

(Ih-31) 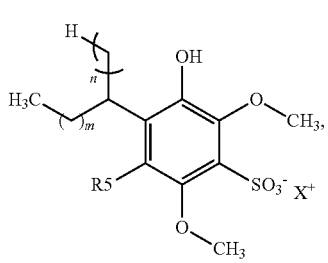

(Ih-32) 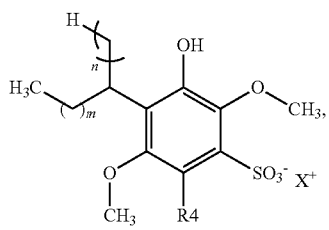

(Ih-33) 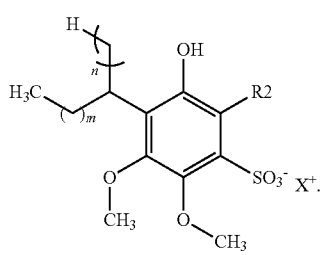

In likewise very particularly preferred representatives of formulas (Ie) or (If) or (Ig) or (Ih), $R^1$ stands for —H, and at least two of the radicals $R^2$, $R^3$, $R^4$, $R^5$, $R^6$ stand for —O—CH$_3$, and at least one other of the radicals $R^2$, $R^3$, $R^4$, $R^5$, $R^6$ stands for —CH$_3$, —CH$_2$CH$_3$, —CH$_2$CH$_2$CH$_3$.

Particularly preferred surfactants may therefore be described by formulas (Ie-37) to (Ie-54) or (If-37) to (If-54) or (Ig-37) to (Ig-54) or (Ih-37) to (Ih-54):

(Ie-37) 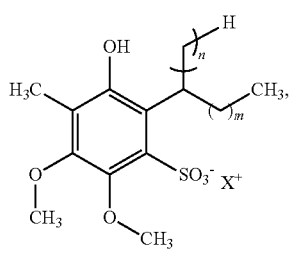

(Ie-38) 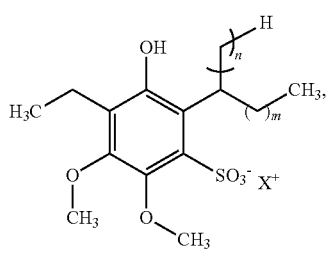

(Ie-39) 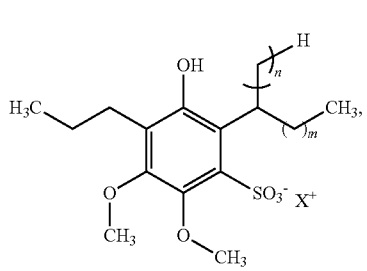

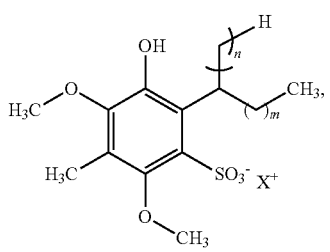
(Ie-40)
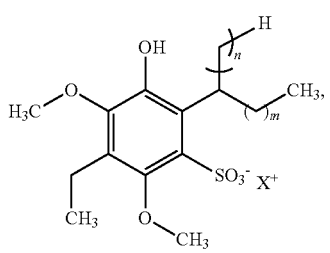
(Ie-41)
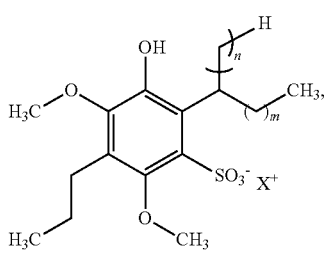
(Ie-42)
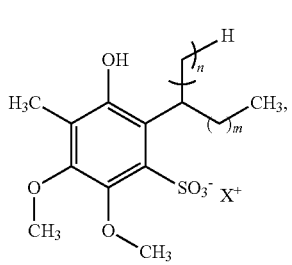
(Ie-43)
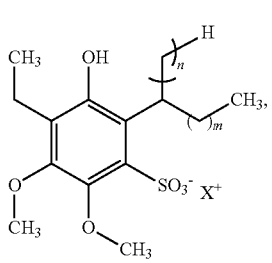
(Ie-44)
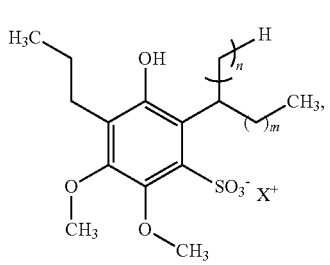
(Ie-45)
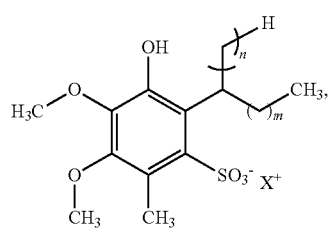
(Ie-46)
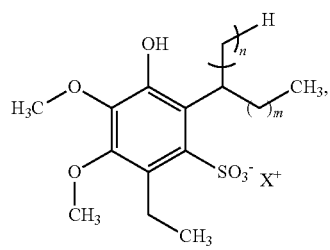
(Ie-47)
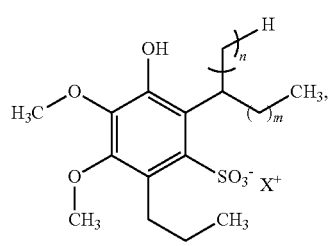
(Ie-48)
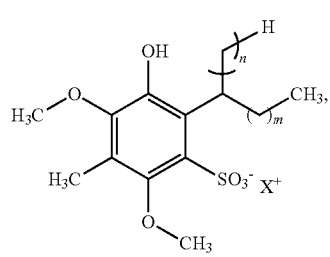
(Ie-49)
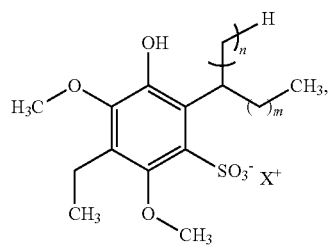
(Ie-50)
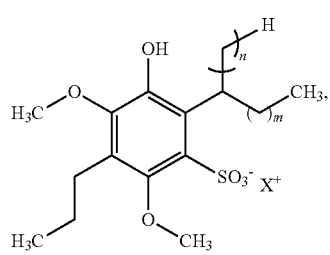
(Ie-51)

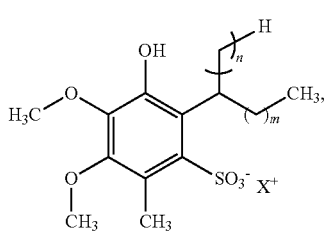
(Ie-52)
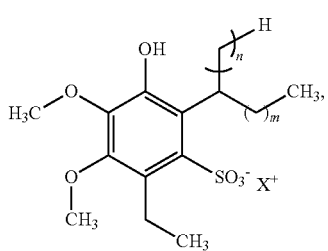
(Ie-53)
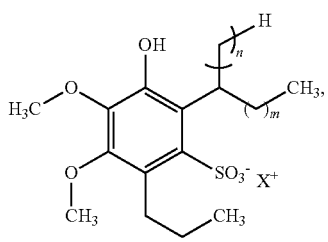
(Ie-54)
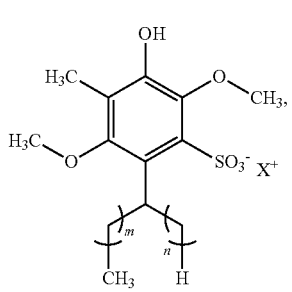
(If-37)
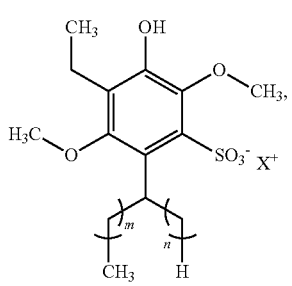
(If-38)
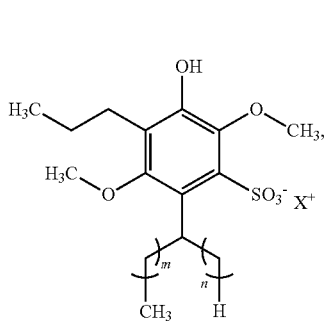
(If-39)
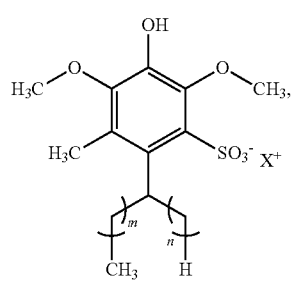
(If-40)
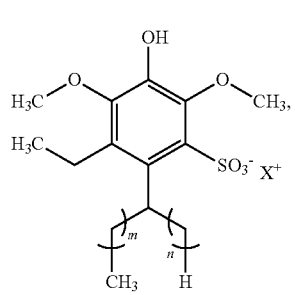
(If-41)
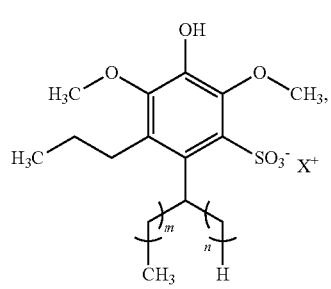
(If-42)
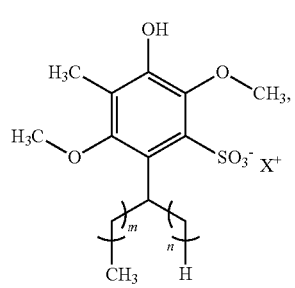
(If-43)
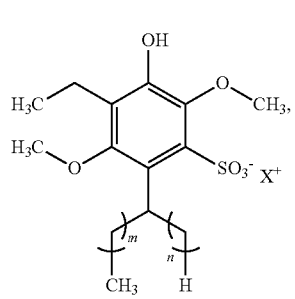
(If-44)

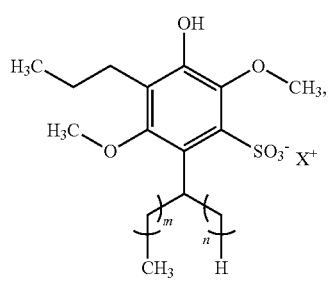
(If-45)
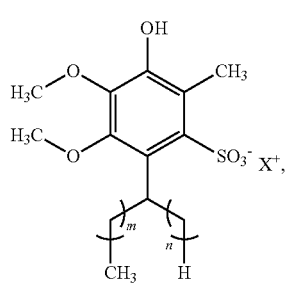
(If-46)
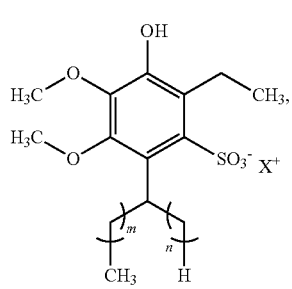
(If-47)
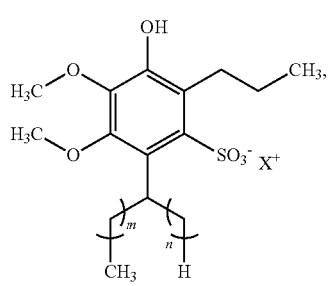
(If-48)
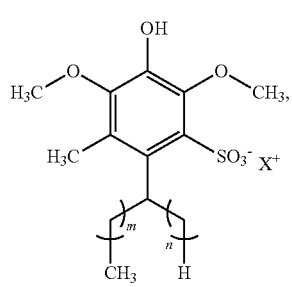
(If-49)
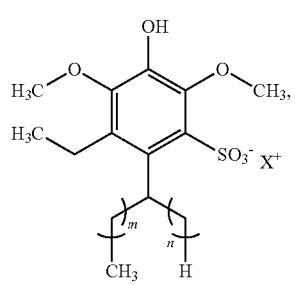
(If-50)
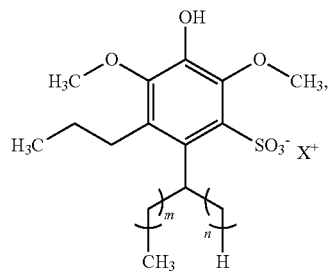
(If-51)
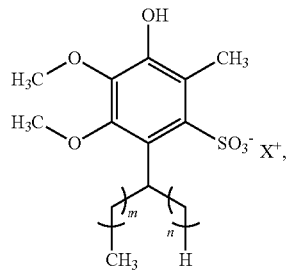
(If-52)
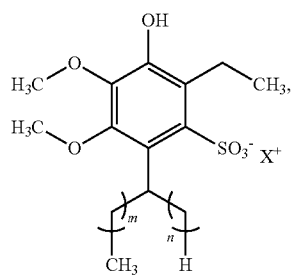
(If-53)
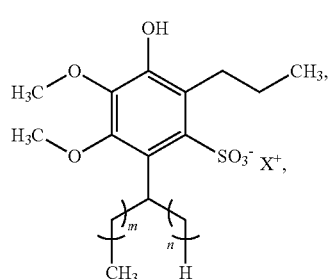
(If-54)
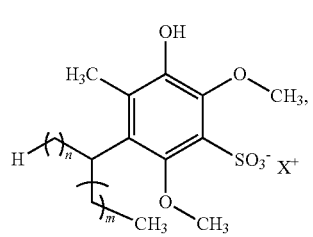
(Ig-37)

-continued
(Ig-38)
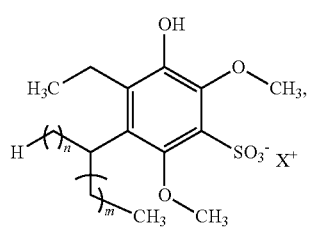
(Ig-39)
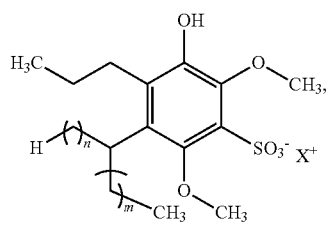
(Ig-40)
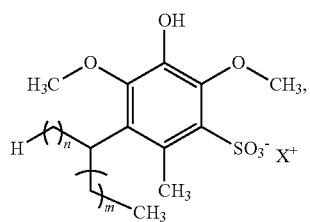
(Ig-41)
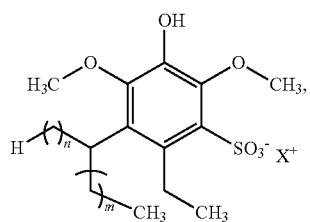
(Ig-42)
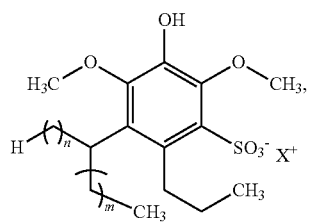
(Ig-43)
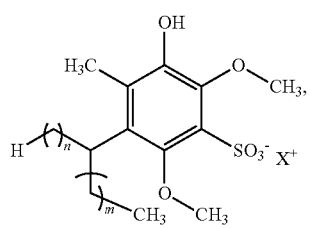
(Ig-44)
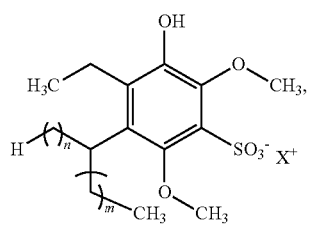
-continued
(Ig-45)
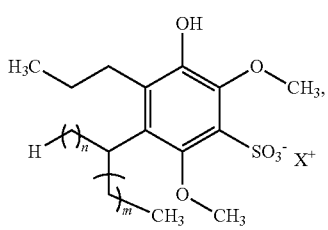
(Ig-46)
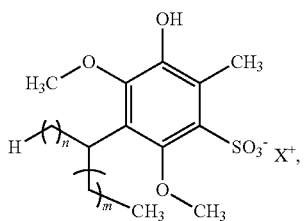
(Ig-47)
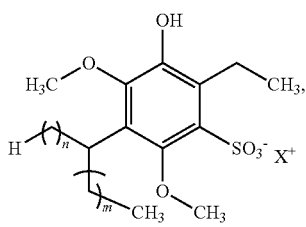
(Ig-48)
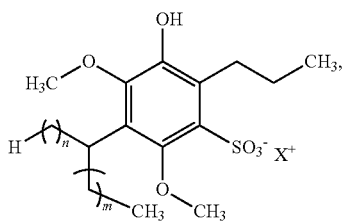
(Ig-49)
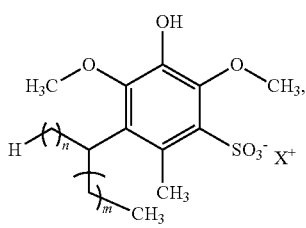
(Ig-50)
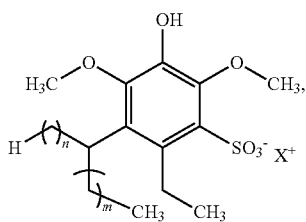
(Ig-51)
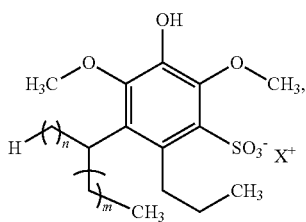

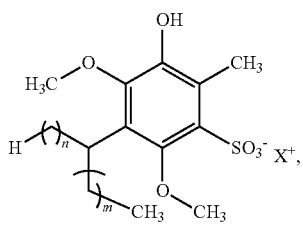
(Ig-52)
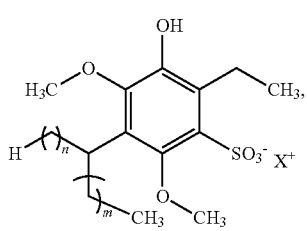
(Ig-53)
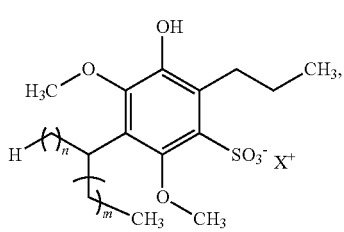
(Ig-54)
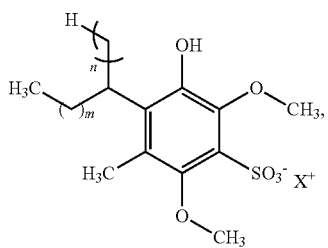
(Ih-37)
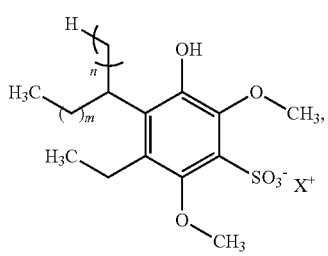
(Ih-38)
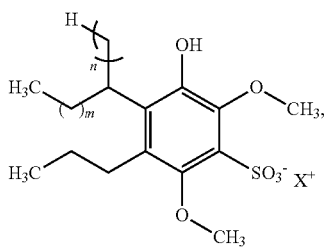
(Ih-39)
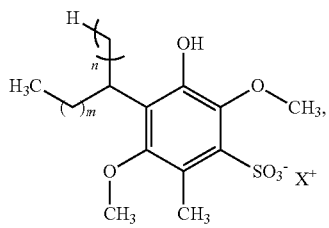
(Ih-40)
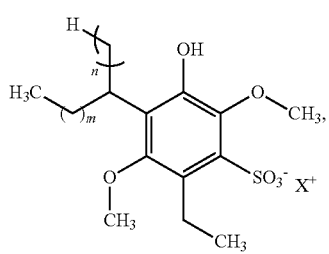
(Ih-41)
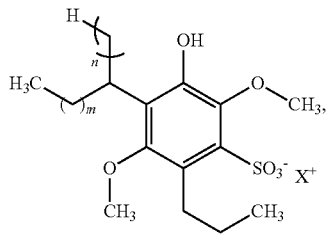
(Ih-42)
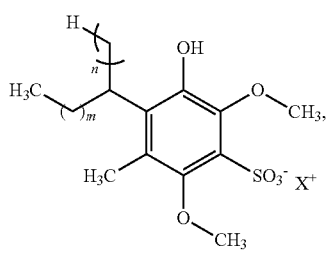
(Ih-43)
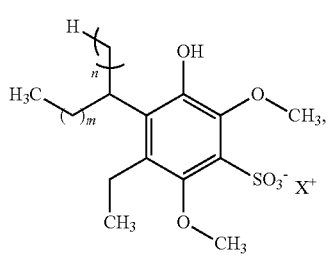
(Ih-44)
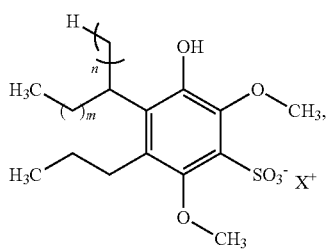
(Ih-45)

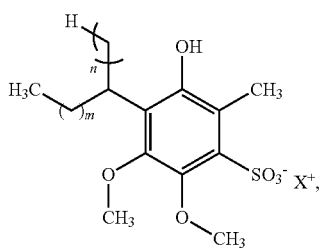 (Ih-46)

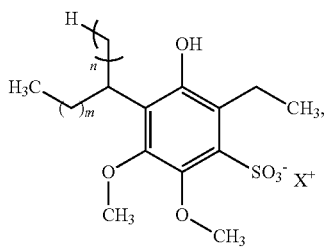 (Ih-47)

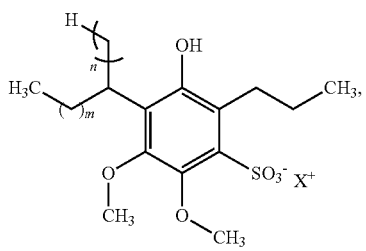 (Ih-48)

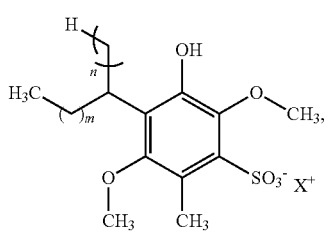 (Ih-49)

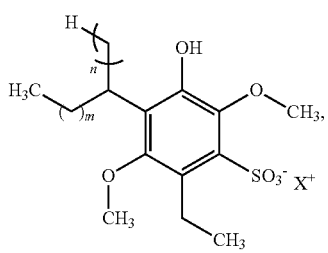 (Ih-50)

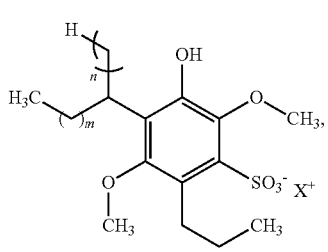 (Ih-51)

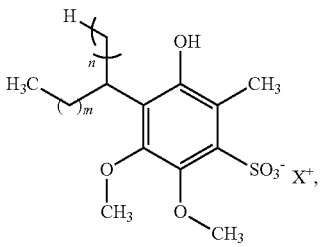 (Ih-52)

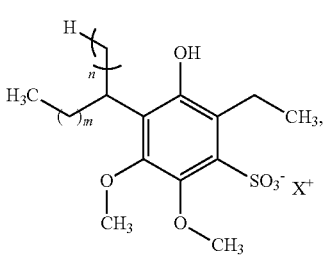 (Ih-53)

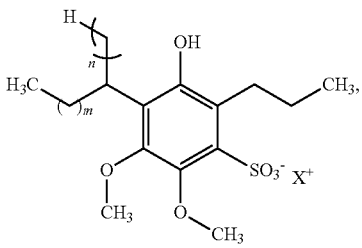 (Ih-54)

The —SO$_3^-$X$^+$ group may also be present in the para-position relative to the —O—R$^1$ radical. Surfactants or surfactant mixtures or detergents or cleaning agents which are likewise particularly preferred according to the invention are therefore characterized in that the surfactant(s) is/are selected from surfactants of formulas (Ii) and/or (Ij) and/or (Ik) and/or (Im):

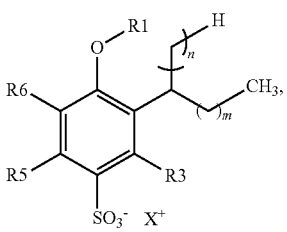 (Ii)

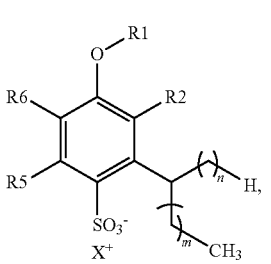 (Ij)

-continued

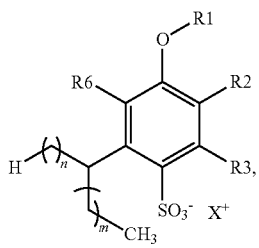
(Ik)

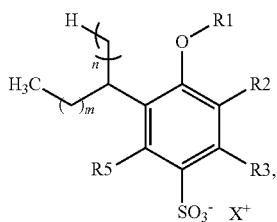
(Im)

in which

R¹ stands for —H or —CH₃,

R², R³, R⁵, R⁶ independently stand for —H, —CH₃, —CH₂CH₃, —CH₂CH₂CH₃, —CH(CH₃)₂, —CH₂CH₂CH₂CH₃, —CH₂CH(CH₃)₂, —CH(CH₃)CH₂CH₃, —C(CH₃)₃, —OH, —OCH₃, —OCH₂CH₃, —OCH₂CH₂CH₃, —OCH(CH₃)₂, n, m independently stand for integers from 0 to 18, with the condition that the sum (m+n) stands for one of the numbers 6, 7, 8, 9, 10, 11, 12, 13, 14, 15, 16, 17, or 18.

In very particularly preferred representatives of formulas (Ii) or (Ij) or (Ik) or (Im), R¹ stands for —H, and at least one of the radicals R², R³, R⁴, R⁵, R⁶ stands for —O—CH₃. Particularly preferred surfactants may therefore be described by formulas (Ii-1) or (Ij-1) or (Ik-1) or (Im-1) or (Ii-2) or (Ij-2) or (Ik-2) or (Im-2) or (Ii-3) or (Ij-3) or (Ik-3) or (Im-3):

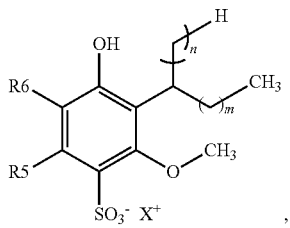
(Ii-1)

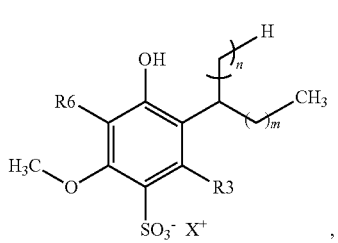
(Ii-2)

-continued

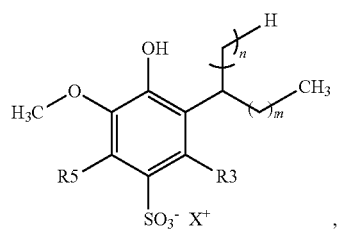
(Ii-3)

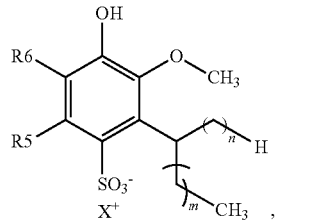
(Ij-1)

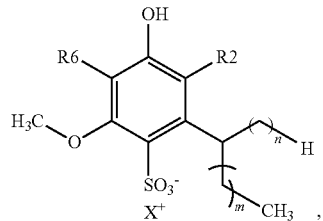
(Ij-2)

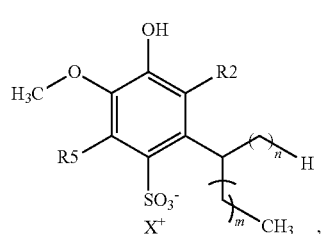
(Ij-3)

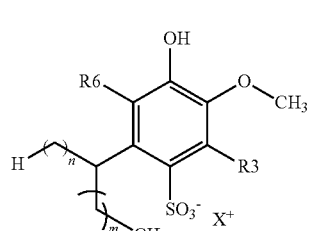
(Ik-1)

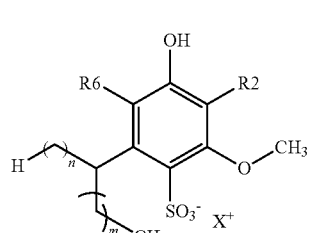
(Ik-2)

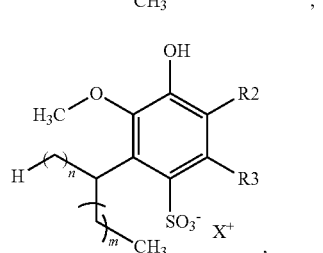
(Ik-3)

(Im-1)

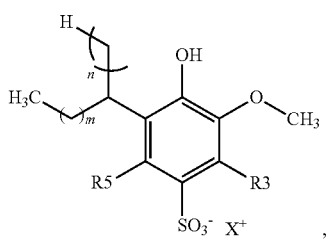

(Im-2)

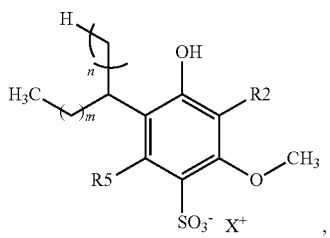

(Im-3)

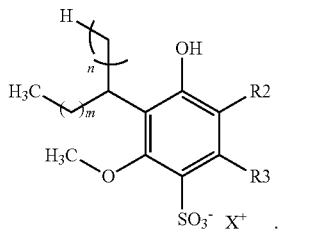

Regardless of whether at least one of the radicals $R^2$, $R^3$, $R^4$, $R^5$, $R^6$ stands for —O—CH$_3$, it is preferred when $R^2$, $R^3$, $R^4$, $R^5$, $R^6$ independently stand for —H, —CH$_3$, —CH$_2$CH$_3$, —CH$_2$CH$_2$CH$_3$, —CH(CH$_3$)$_2$. Molecules in which at least one of the radicals $R^2$, $R^3$, $R^4$, $R^5$, $R^6$ stands for —CH$_3$, —CH$_2$CH$_3$, —CH$_2$CH$_2$CH$_3$ are preferred according to the invention.

Particularly preferred surfactants may therefore be described by formulas (Ii-4) to (Ii-12) or (Ij-4) to (Ij-12) or (Ik-4) to (Ik-12) or (Im-4) to (Im-12):

(Ii-4)

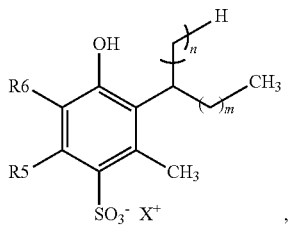

(Ii-5)

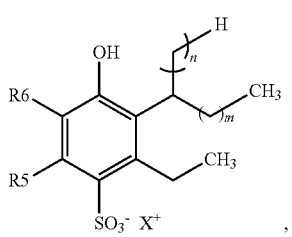

(Ii-6)

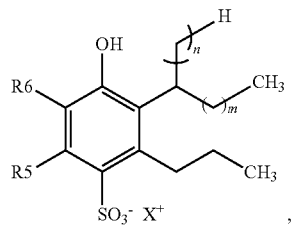

(Ii-7)

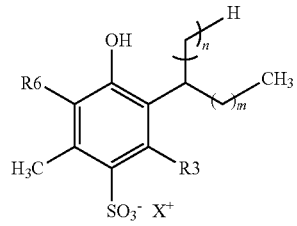

(Ii-8)

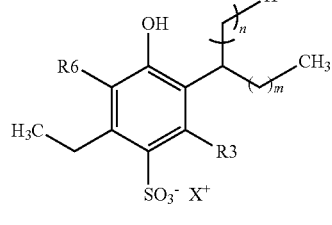

(Ii-9)

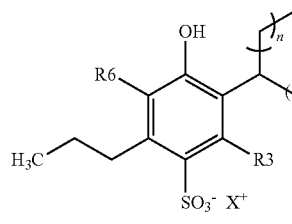

(Ii-10)

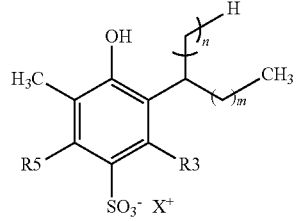

(Ii-11)

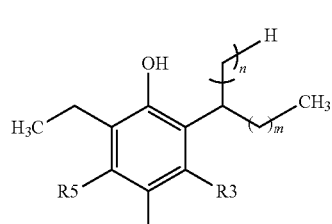

(Ii-12)

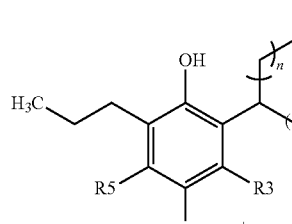

-continued
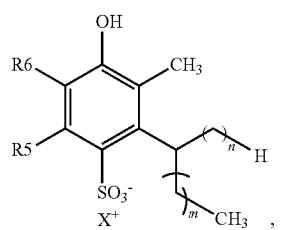
(Ij-4)
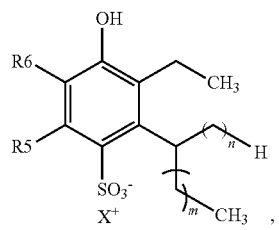
(Ij-5)
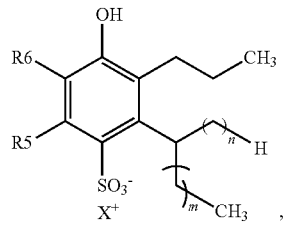
(Ij-6)
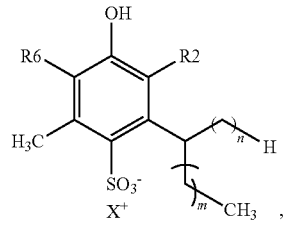
(Ij-7)
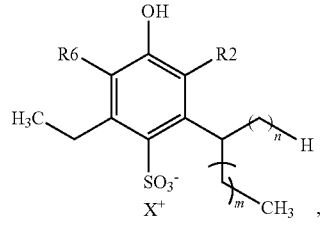
(Ij-8)
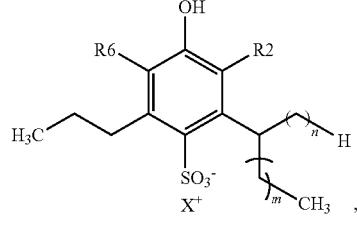
(Ij-9)
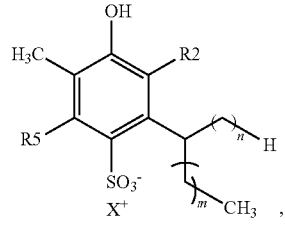
(Ij-10)
-continued
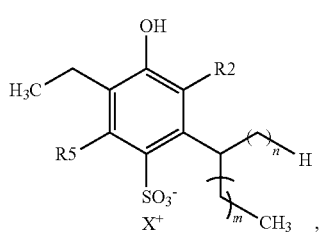
(Ij-11)
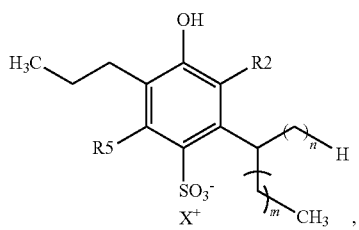
(Ij-12)
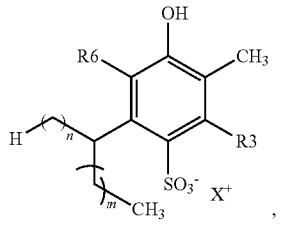
(Ik-4)
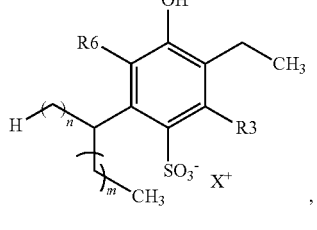
(Ik-5)
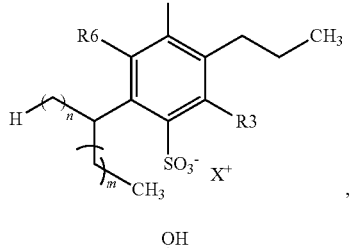
(Ik-6)
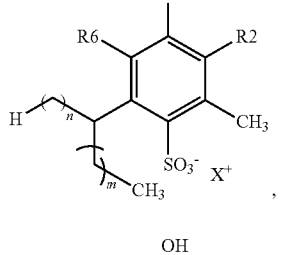
(Ik-7)
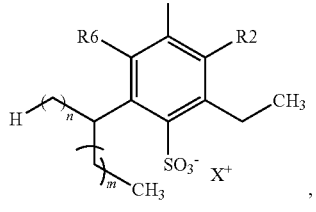
(Ik-8)

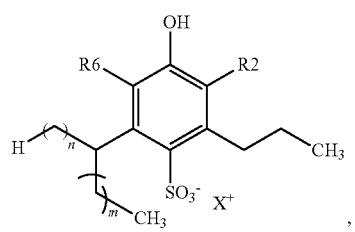
(Ik-9)
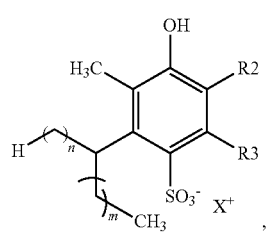
(Ik-10)
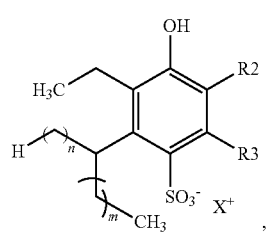
(Ik-11)
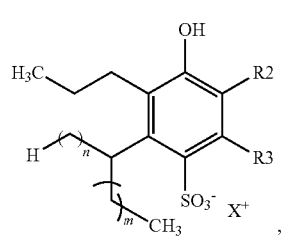
(Ik-12)
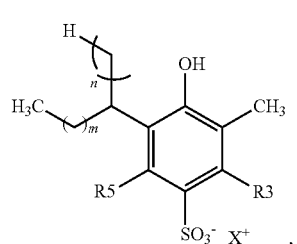
(Im-4)
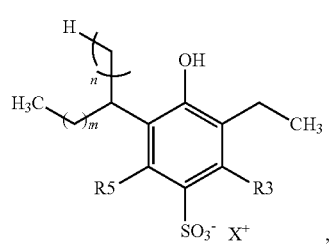
(Im-5)
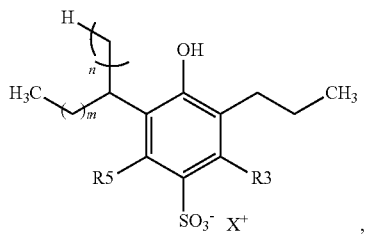
(Im-6)
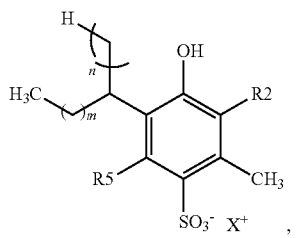
(Im-7)
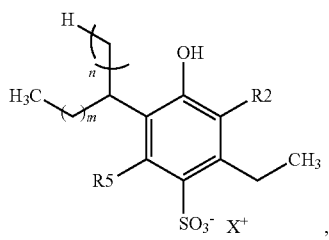
(Im-8)
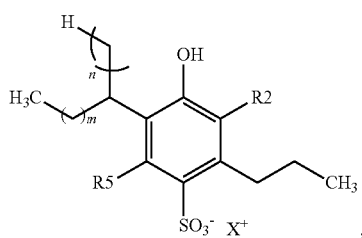
(Im-9)
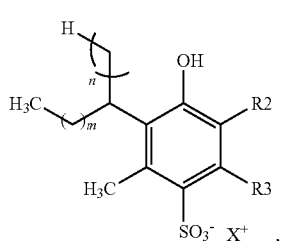
(Im-10)
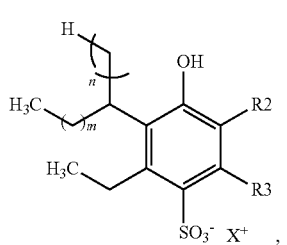
(Im-11)

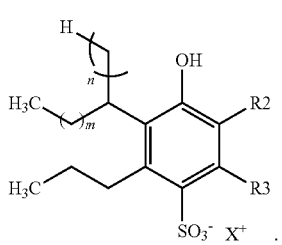

(Im-12)

In very particularly preferred representatives of formulas (Ii) or (Ij) or (Ik) or (Im), $R^1$ stands for —H, and at least one of the radicals $R^2$, $R^3$, $R^4$, $R^5$, $R^6$ stands for —O—$CH_3$, and at least one other of the radicals $R^2$, $R^3$, $R^4$, $R^5$, $R^6$ stands for —$CH_3$, —$CH_2CH_3$, —$CH_2CH_2CH_3$.

Particularly preferred surfactants may therefore be described by formulas (Ii-13) to (Ii-30) or (Ij-13) to (Ij-30) or (Ik-13) to (Ik-30) or (Im-13) to (Im-30):

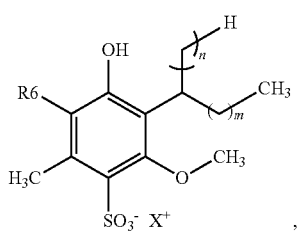

(Ii-13)

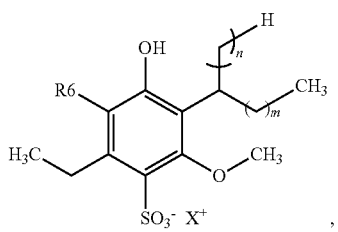

(Ii-14)

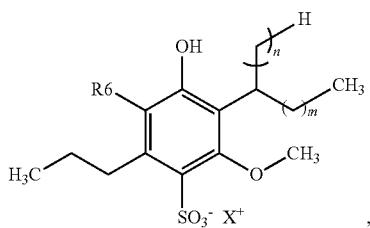

(Ii-15)

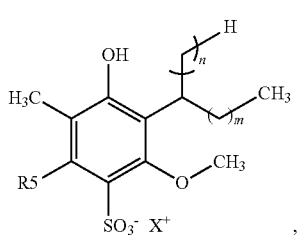

(Ii-16)

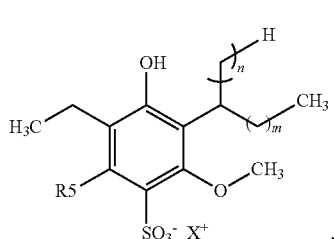

(Ii-17)

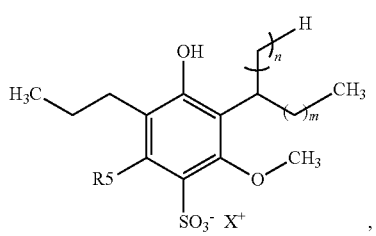

(Ii-18)

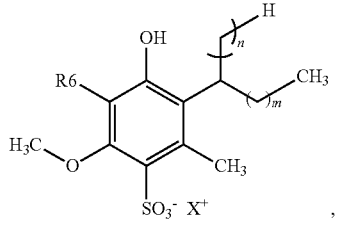

(Ii-19)

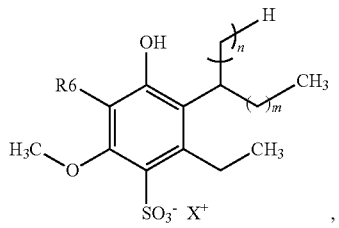

(Ii-20)

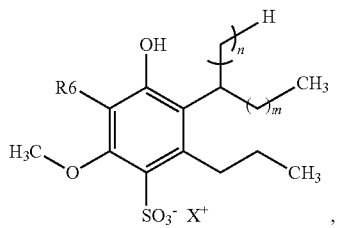

(Ii-21)

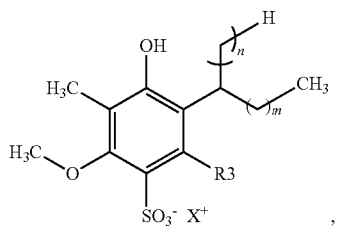

(Ii-22)

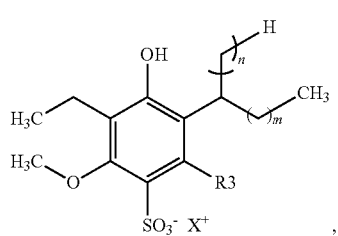 (Ii-23)
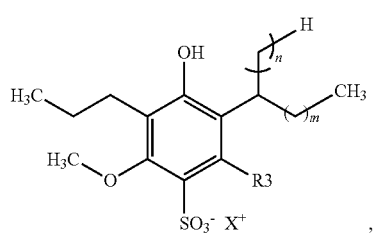 (Ii-24)
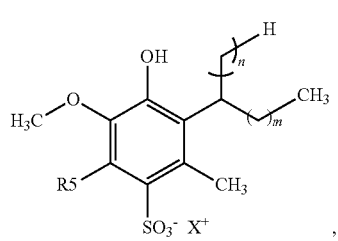 (Ii-25)
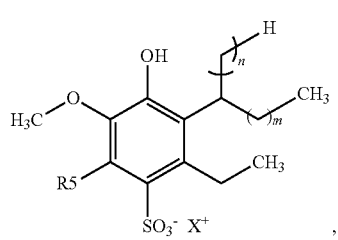 (Ii-26)
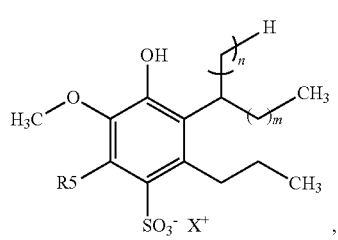 (Ii-27)
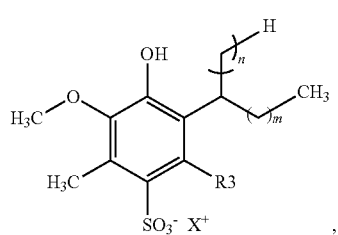 (Ii-28)
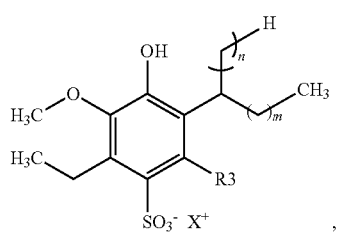 (Ii-29)
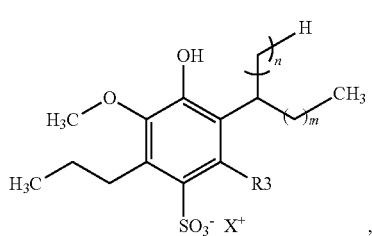 (Ii-30)
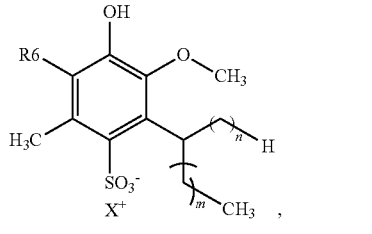 (Ij-13)
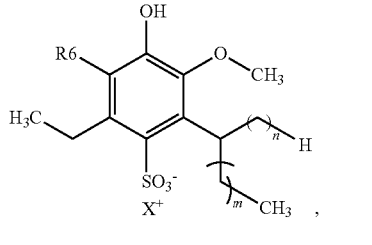 (Ij-14)
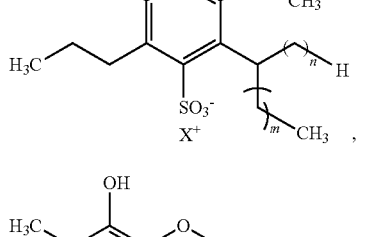 (Ij-15)
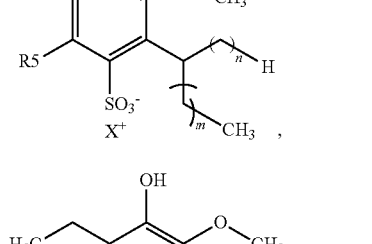 (Ij-16)
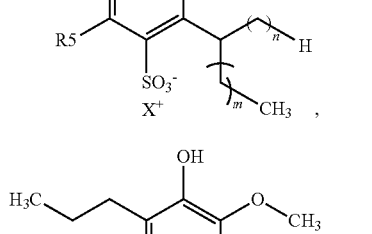 (Ij-17)
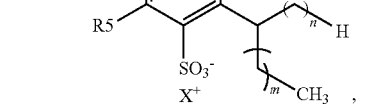 (Ij-18)

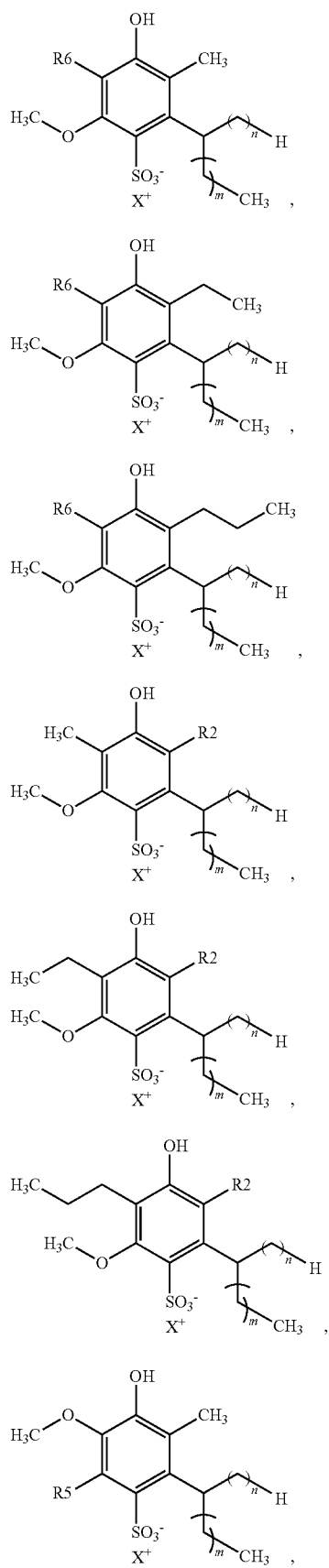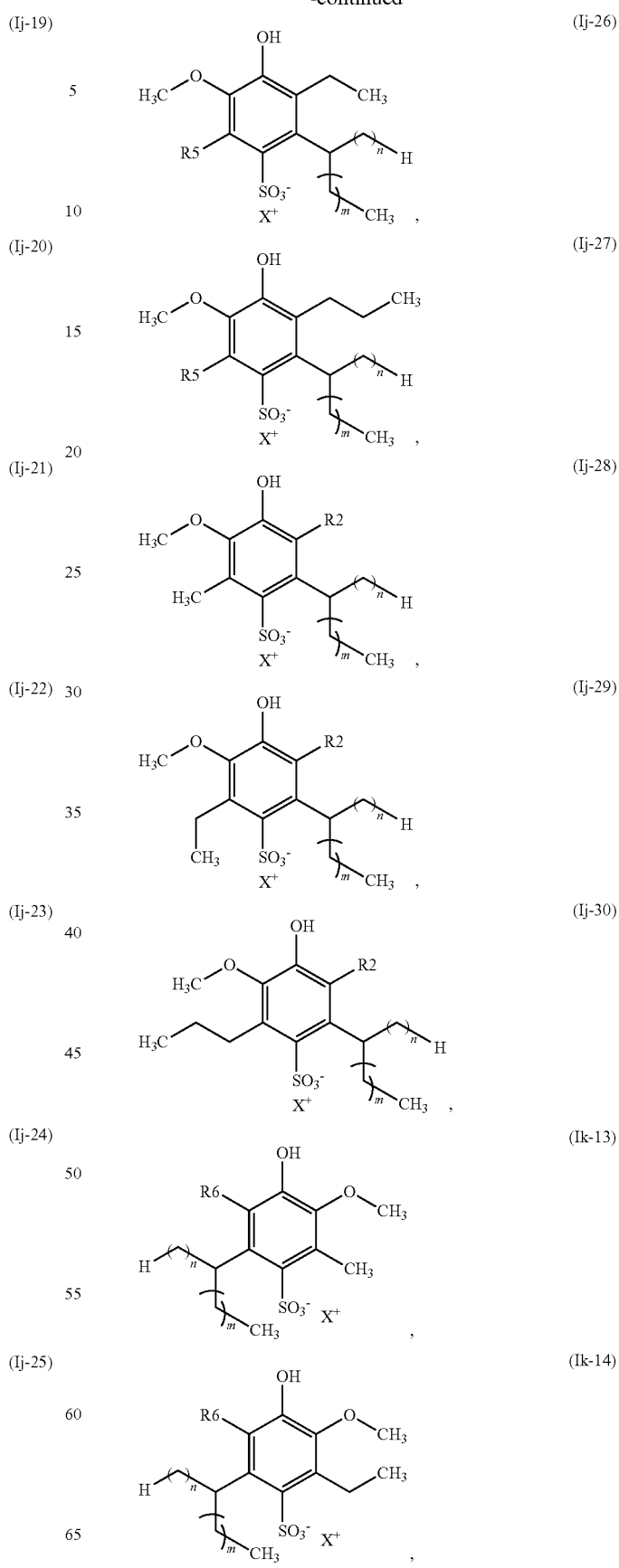

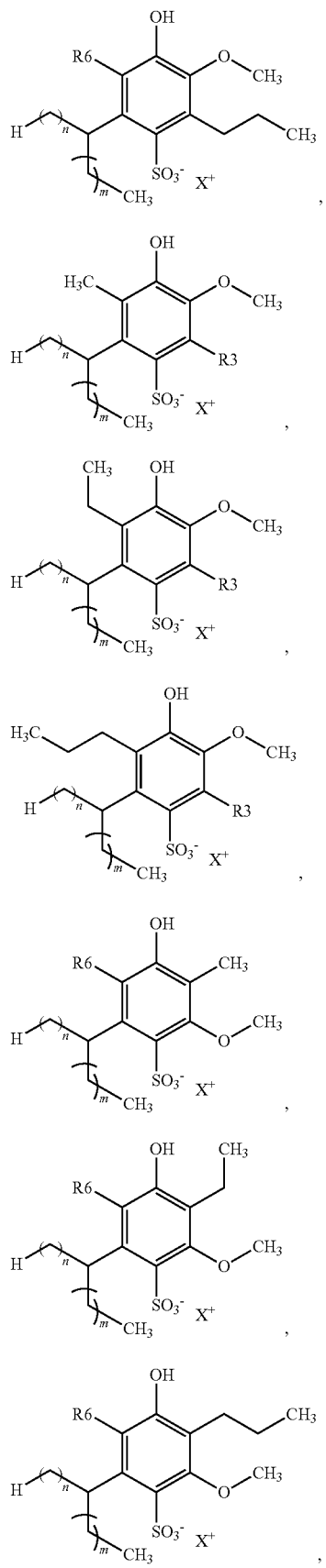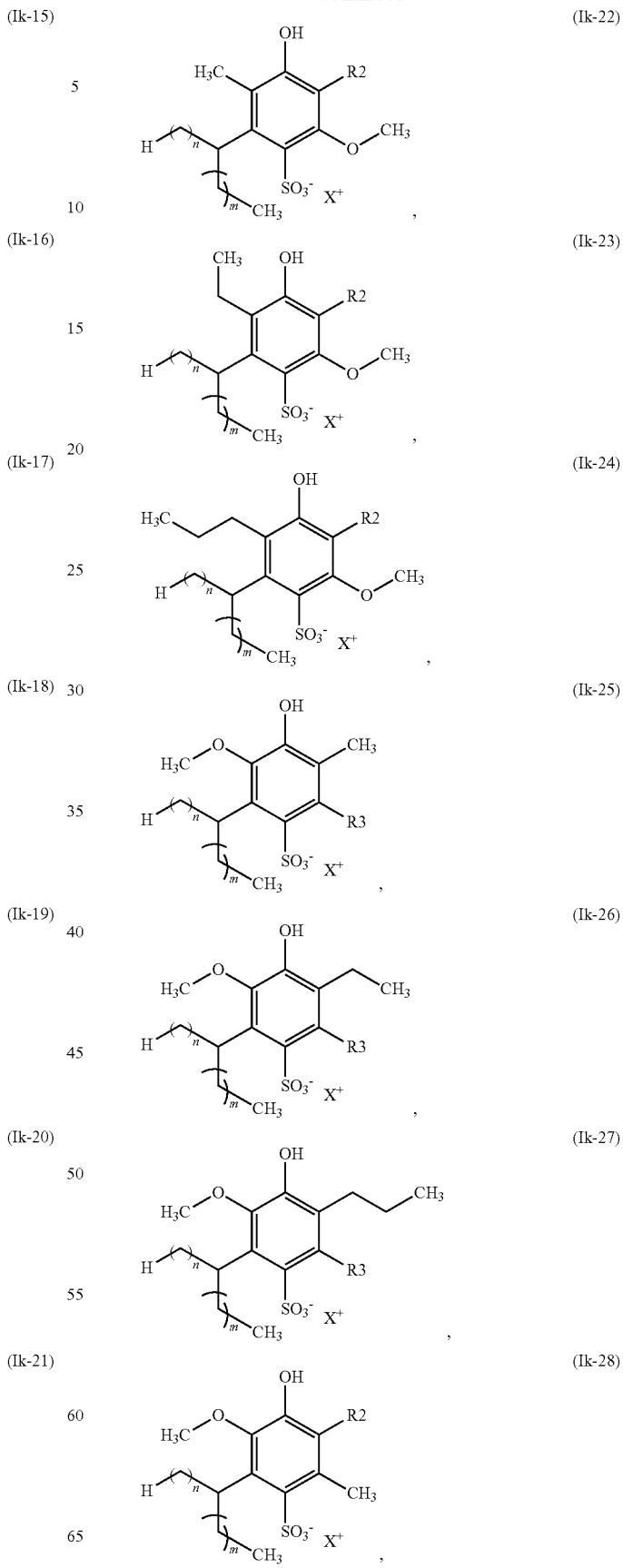

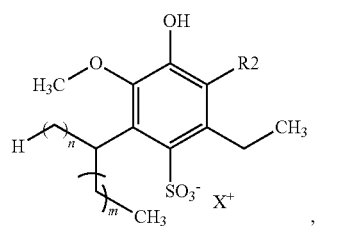
(Ik-29)
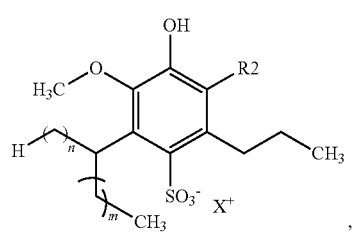
(Ik-30)
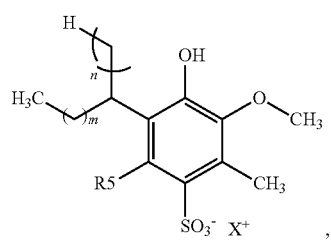
(Im-13)
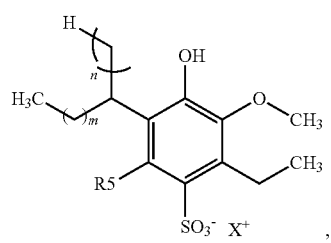
(Im-14)
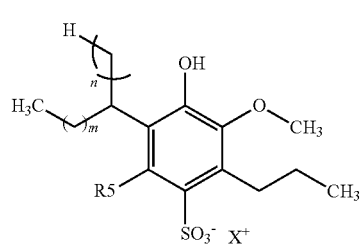
(Im-15)
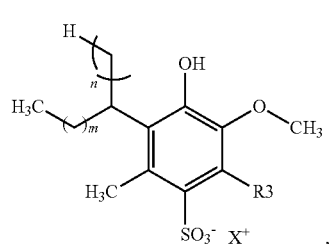
(Im-16)
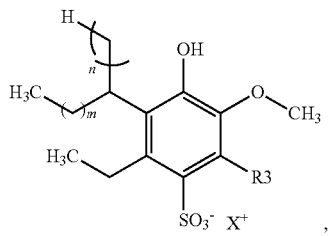
(Im-17)
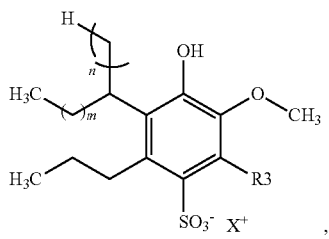
(Im-18)
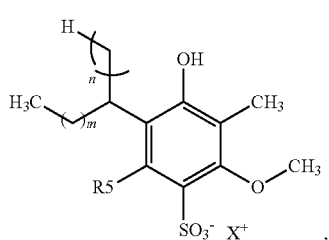
(Im-19)
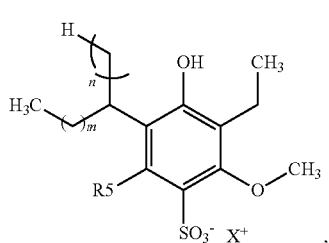
(Im-20)
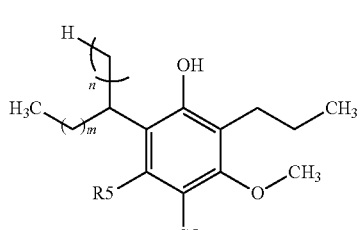
(Im-21)
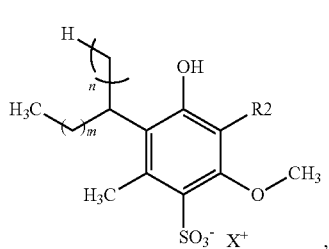
(Im-22)

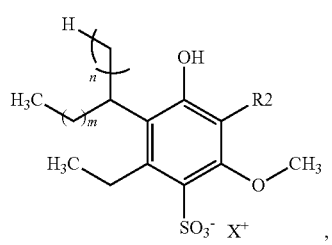
(Im-23)
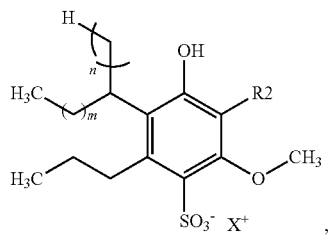
(Im-24)
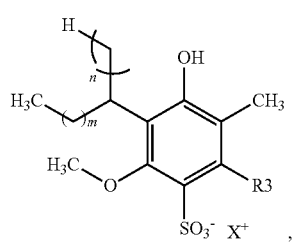
(Im-25)
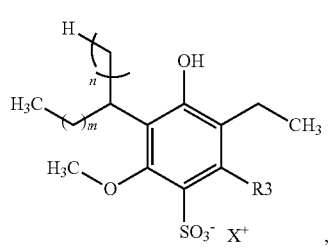
(Im-26)
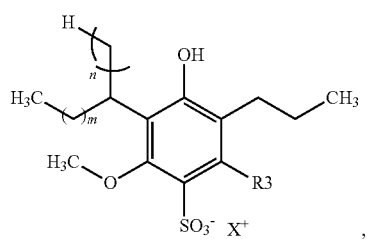
(Im-27)
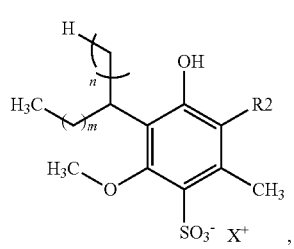
(Im-28)
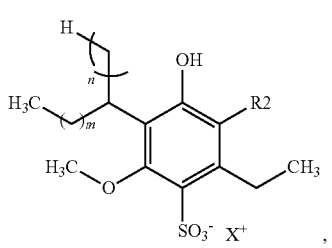
(Im-29)
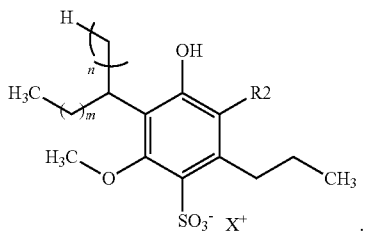
(Im-30)
In likewise very particularly preferred representatives of formulas (Ii) or (Ij) or (Ik) or (Im), $R^1$ stands for —H, and at least two of the radicals $R^2$, $R^3$, $R^4$, $R^5$, $R^6$ stand for —O—$CH_3$.
Particularly preferred surfactants may therefore be described by formulas (Ii-31) to (Ii-33) or (Ij-31) to (Ij-33) or (Ik-31) to (Ik-33) or (Im-31) to (Im-33):
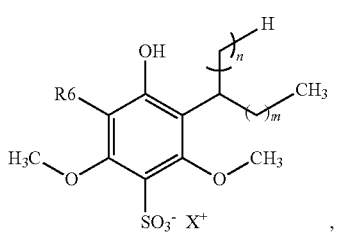
(Ii-31)
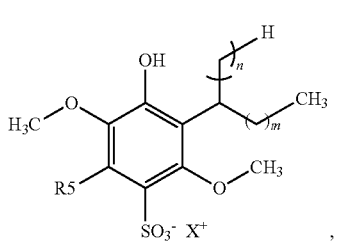
(Ii-32)
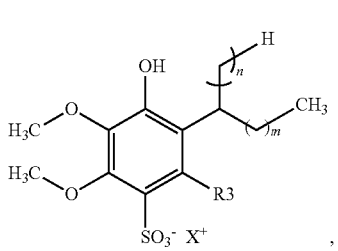
(Ii-33)

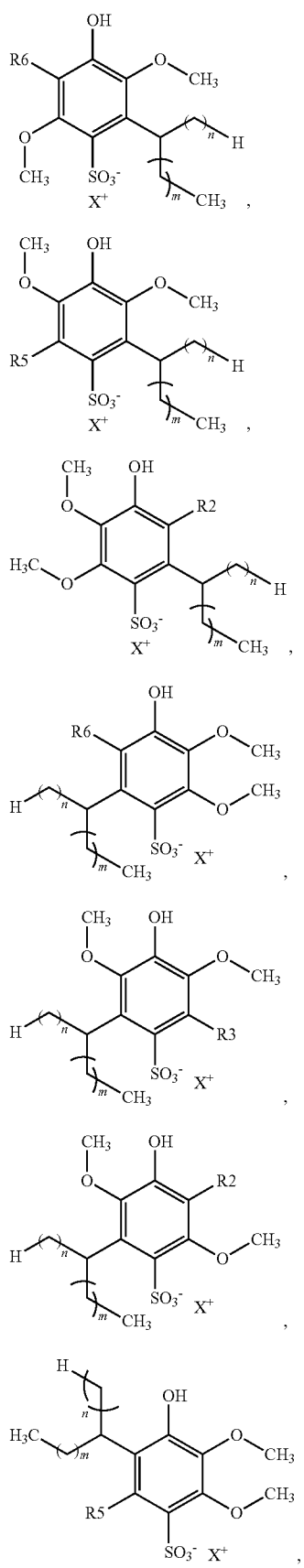
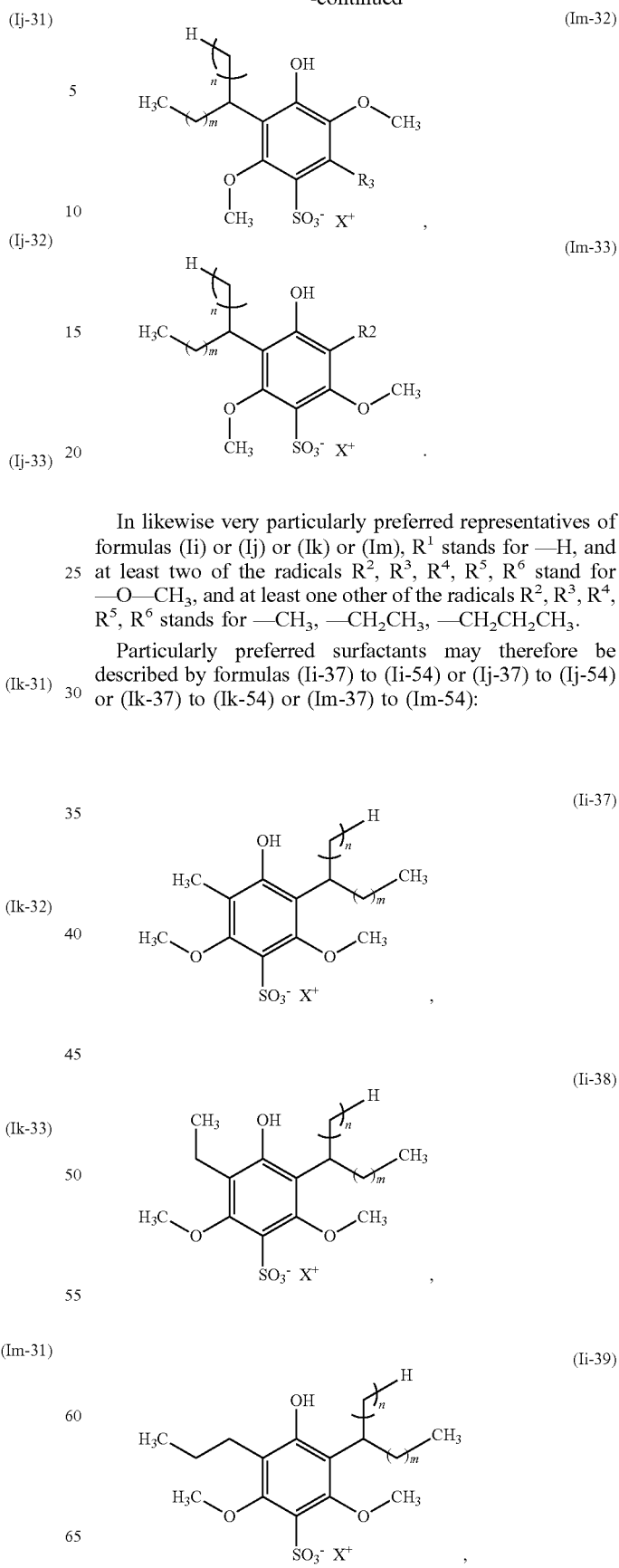

In likewise very particularly preferred representatives of formulas (Ii) or (Ij) or (Ik) or (Im), $R^1$ stands for —H, and at least two of the radicals $R^2$, $R^3$, $R^4$, $R^5$, $R^6$ stand for —O—CH$_3$, and at least one other of the radicals $R^2$, $R^3$, $R^4$, $R^5$, $R^6$ stands for —CH$_3$, —CH$_2$CH$_3$, —CH$_2$CH$_2$CH$_3$.

Particularly preferred surfactants may therefore be described by formulas (Ii-37) to (Ii-54) or (Ij-37) to (Ij-54) or (Ik-37) to (Ik-54) or (Im-37) to (Im-54):

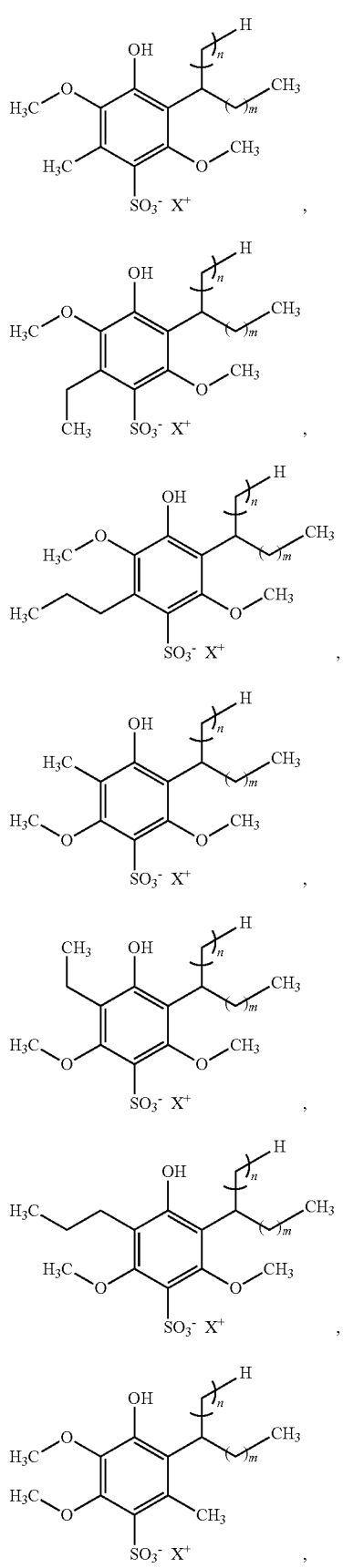

-continued
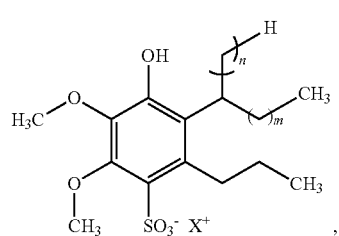
(Ii-54)
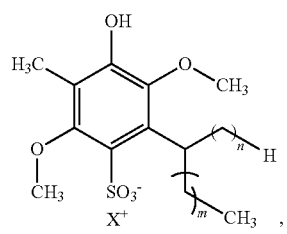
(Ij-37)
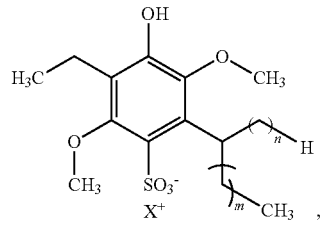
(Ij-38)
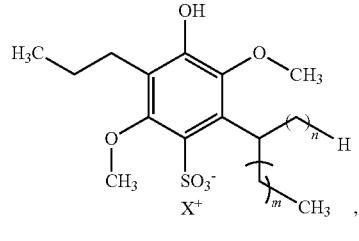
(Ij-39)
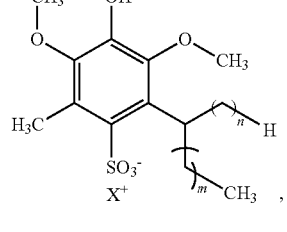
(Ij-40)
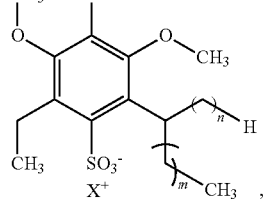
(Ij-41)
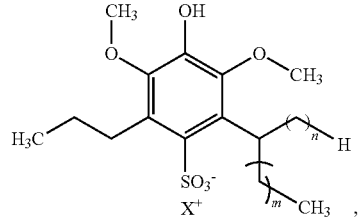
(Ij-42)
-continued
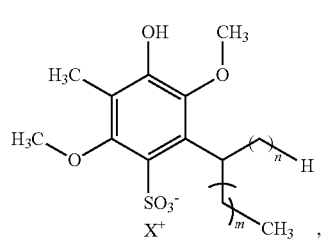
(Ij-43)
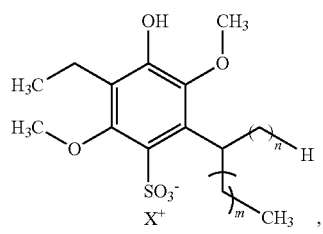
(Ij-44)
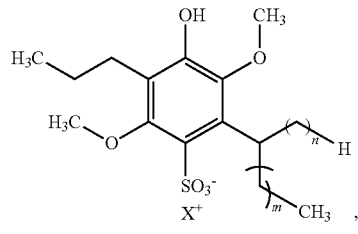
(Ij-45)
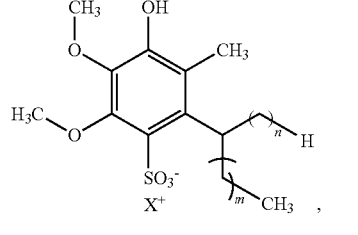
(Ij-46)
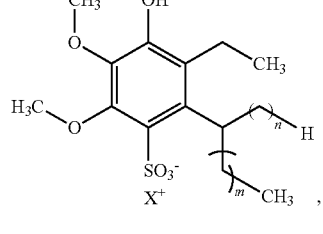
(Ij-47)
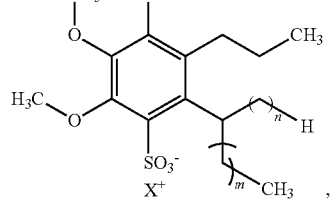
(Ij-48)
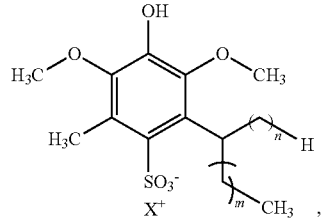
(Ij-49)

-continued
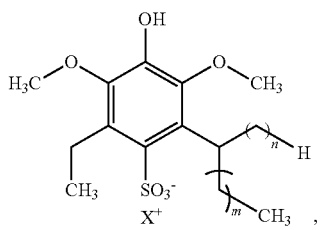
(Ij-50)
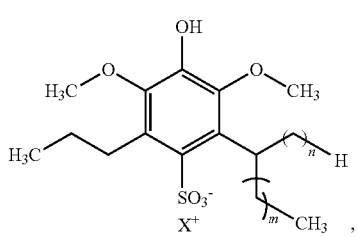
(Ij-51)
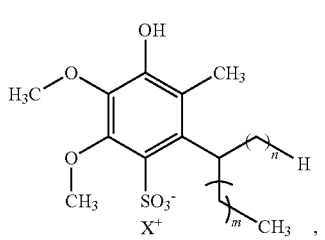
(Ij-52)
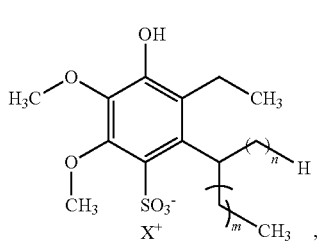
(Ij-53)
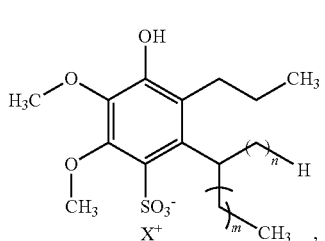
(Ij-54)
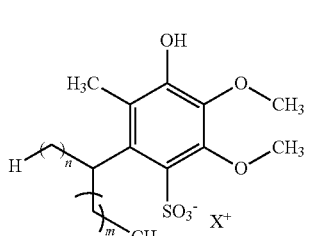
(Ik-37)
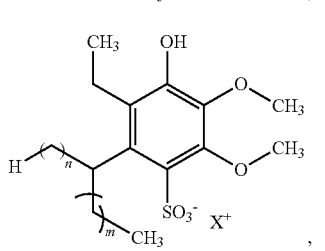
(Ik-38)
-continued
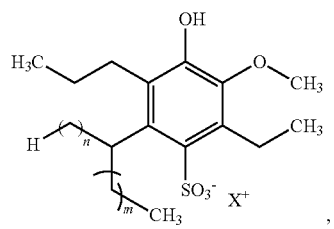
(Ik-39)
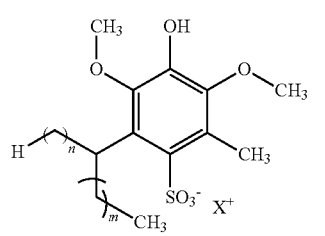
(Ik-40)
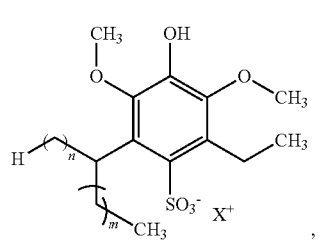
(Ik-41)
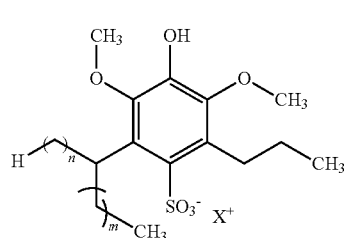
(Ik-42)
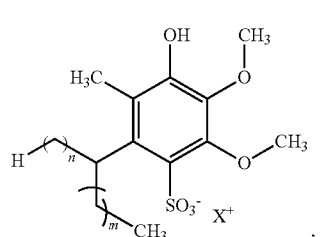
(Ik-43)
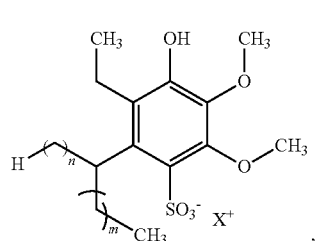
(Ik-44)
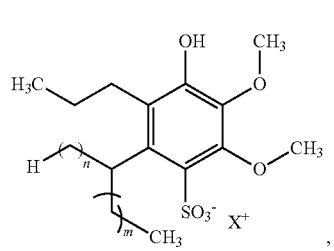
(Ik-45)

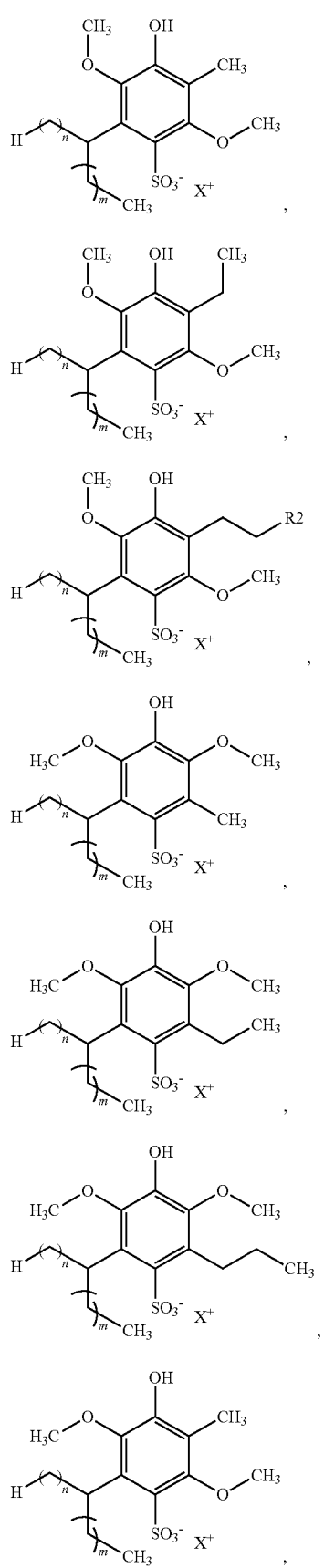
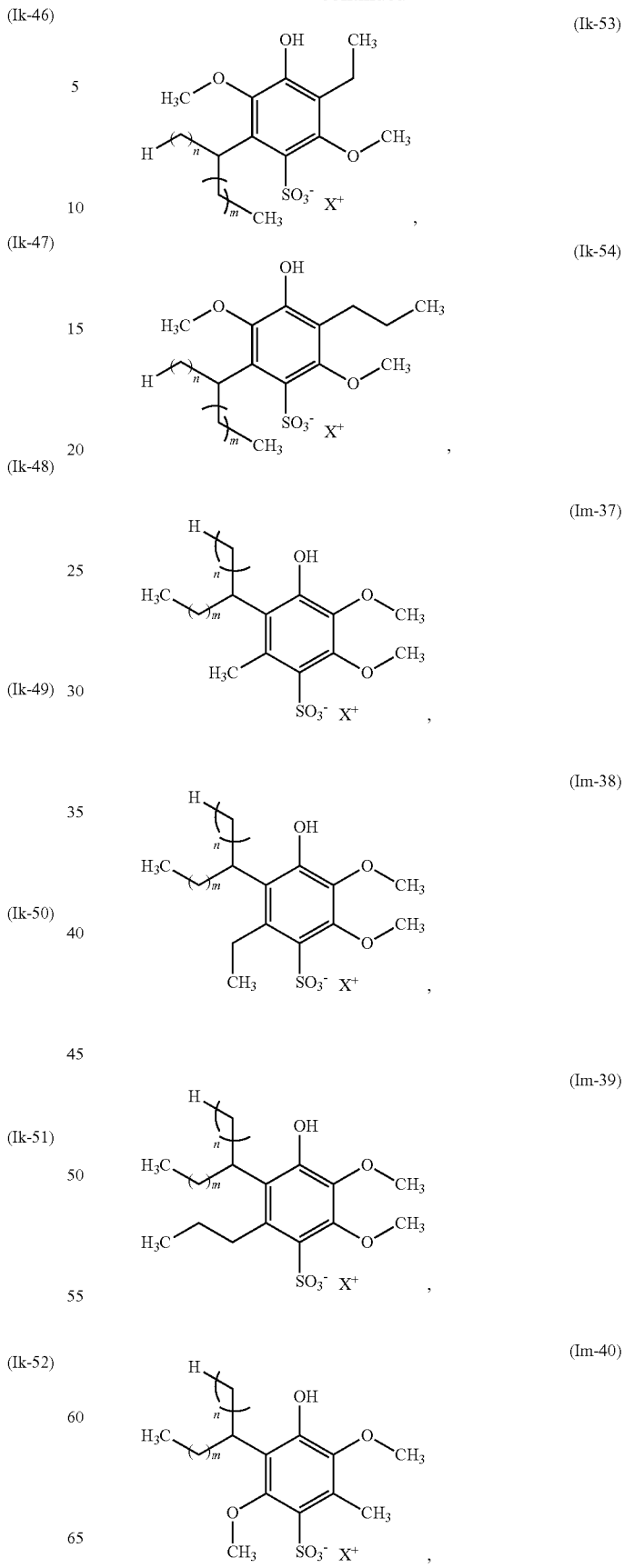

(Im-41)
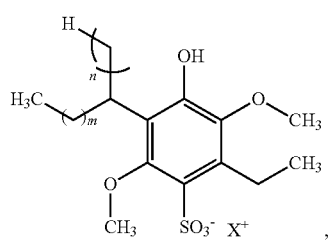
(Im-42)
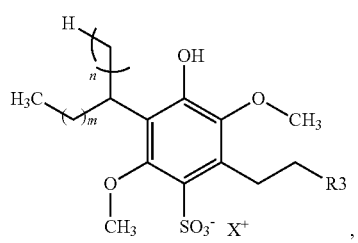
(Im-43)
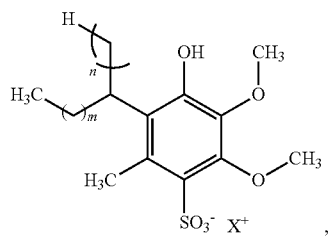
(Im-44)
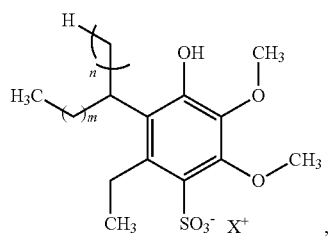
(Im-45)
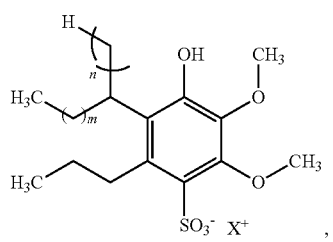
(Im-46)
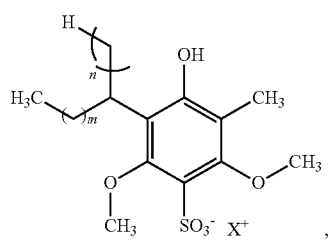
(Im-47)
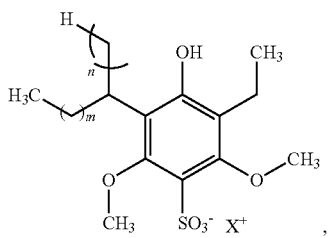
(Im-48)
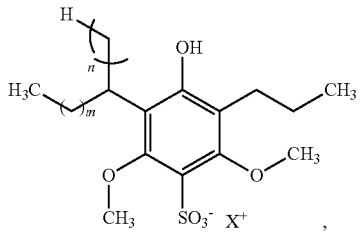
(Im-49)
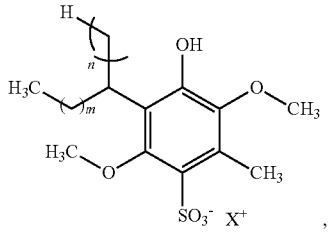
(Im-50)
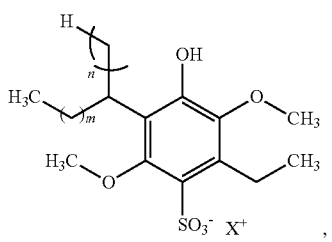
(Im-51)
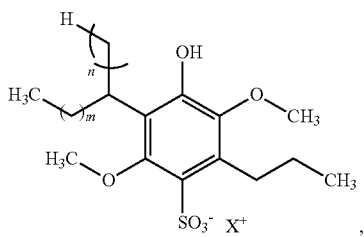
(Im-52)
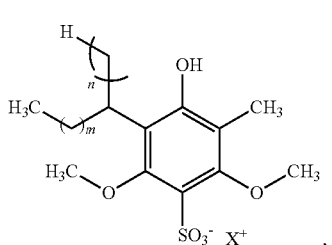

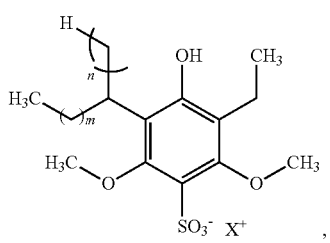

(Im-53)

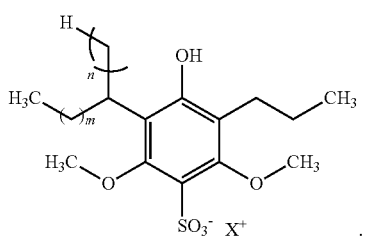

(Im-54)

Representatives of all of the above-mentioned formulas in which the remaining radicals $R^2$, $R^3$, $R^4$, $R^5$, $R^6$ stand for —H are particularly preferred.

$X^+$ stands for a monovalent cation or the nth part of an n-valent cation; alkali metal ions, and among same, $Na^+$ or K, are preferred, with $Na^+$ being extremely preferred. Further cations $X^+$ may be selected from $NH_4^+$, $\frac{1}{2}Zn^{2+}$, $\frac{1}{2}Mg^{2+}$, $\frac{1}{2}Ca^{2+}$, $\frac{1}{2}Mn^{2+}$, and the mixtures thereof.

Representatives of all of the above-mentioned formulas in which $X^+$ stands for $Na^+$ are particularly preferred.

Representatives of all of the above-mentioned formulas in which all remaining radicals $R^2$, $R^3$, $R^4$, $R^5$, $R^6$ stand for —H and $X^+$ stands for $Na^+$ are particularly preferred.

The group

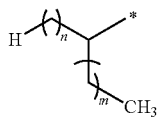

stands for a linear or branched alkyl radical containing 8 to 20 C atoms. n and m independently stand for integers from 0 to 18, with the condition that the sum (m+n) stands for one of the numbers 6, 7, 8, 9, 10, 11, 12, 13, 14, 15, 16, 17, or 18.

Linear alkyl radicals (n=0) are preferably selected from n-decyl (m=8), n-undecyl (m=9), n-dodecyl (m=10), n-tridecyl (m=11), n-tetradecyl (m=12), n-pentadecyl (m=13), n-hexadecyl (m=14), n-heptadecyl (m=15), and n-octadecyl (m=16) radicals.

Branched alkyl radicals (n>0) are preferably selected from 2-decyl (n=1, m=7), 2-undecyl (n=1, m=8), 2-dodecyl (n=1, m=9), 2-tridecyl (n=1, m=10), 2-tetradecyl (n=1, m=11), 2-pentadecyl (n=1, m=12), 2-hexadecyl (n=1, m=13), 2-heptadecyl (n=1, m=14), 2-octadecyl (n=1, m=15) radicals, 3-decyl (n=2, m=6), 3-undecyl (n=2, m=7), 3-dodecyl (n=2, m=8), 3-tridecyl (n=2, m=9), 3-tetradecyl (n=2, m=10), 3-pentadecyl (n=2, m=11), 3-hexadecyl (n=2, m=12), 3-heptadecyl (n=2, m=13), 3-octadecyl (n=2, m=14) radicals, 4-decyl (n=3, m=5), 4-undecyl (n=3, m=6), 4-dodecyl (n=3, m=7), 4-tridecyl (n=3, m=8), 4-tetradecyl (n=3, m=9), 4-pentadecyl (n=3, m=10), 4-hexadecyl (n=3, m=11), 4-heptadecyl (n=3, m=12), 4-octadecyl (n=3, m=13) radicals, 5-decyl (n=4, m=4), 5-undecyl (n=4, m=5), 5-dodecyl (n=4, m=6), 5-tridecyl (n=4, m=7), 5-tetradecyl (n=4, m=8), 5-pentadecyl (n=4, m=9), 5-hexadecyl (n=4, m=10), 5-heptadecyl (n=4, m=11), 5-octadecyl (n=4, m=12) radicals, 6-undecyl (n=5, m=4), 6-dodecyl (n=5, m=5), 6-tridecyl (n=5, m=6), 6-tetradecyl (n=5, m=7), 6-pentadecyl (n=5, m=8), 6-hexadecyl (n=5, m=9), 6-heptadecyl (n=5, m=10), 6-octadecyl (n=5, m=11) radicals, 7-tridecyl (n=6, m=5), 7-tetradecyl (n=6, m=6), 7-pentadecyl (n=6, m=7), 7-hexadecyl (n=6, m=8), 7-heptadecyl (n=6, m=9), 7-octadecyl (n=6, m=10) radicals, 8-pentadecyl (n=7, m=6), 8-hexadecyl (n=7, m=7), 8-heptadecyl (n=7, m=8), 8-octadecyl (n=7, m=9) radicals, 9-heptadecyl (n=8, m=7) and 9-octadecyl (n=8, m=8) radicals.

The surfactants according to the invention have excellent physical properties and also have excellent compatibility with other surfactants, so that surfactant mixtures may be produced which are extremely stable in storage and cold-resistant. The surfactants according to the invention develop excellent detergent and cleaning power in detergents or cleaning agents, and may be used therein in a broad concentration range. Surfactant mixtures or detergents or cleaning agents which are particularly preferred according to the invention contain, based on their weight, 1 to 99% by weight, preferably 5 to 85% by weight, particularly preferably 10 to 75% by weight, and in particular 15 to 65% by weight, of at least one surfactant of formula (Ia) and/or (Ib) and/or (Ic) and/or (Id) and/or (Ie) and/or (If) and/or (Ig) and/or (Ih) and/or (Ii) and/or (Ij) and/or (Ik) and/or (Im).

Surfactant mixtures or detergents or cleaning agents which are preferred according to the invention are characterized in that they contain, based on the total quantity of all surfactants, 5 to 75% by weight, preferably 7.5 to 40% by weight, more preferably 10 to 35% by weight, even more preferably 12.5 to 32.5% by weight, and in particular 15 to 30% by weight, of surfactant(s) of formula $R^7$—O-(AO)$_m$—H, in which
$R^7$ stands for a linear or branched, substituted or unsubstituted alkyl, aryl, or alkylaryl radical,
AO stands for an ethylene oxide (EO) or propylene oxide (PO) group,
m stands for integers from 1 to 50.

In this formula, $R^7$ stands for a linear or branched, substituted or unsubstituted alkyl, aryl, or alkylaryl radical, preferably for a linear, unsubstituted alkyl radical, particularly preferably for a fatty alcohol radical. Preferred radicals $R^7$ are selected from decyl, undecyl, dodecyl, tridecyl, tetradecyl, pentadecyl, hexadecyl, heptadecyl, octadecyl, nonadecyl, eicosyl radicals and the mixtures thereof, the representatives having an even number of C atoms being preferred. Particularly preferred radicals $R^2$ are derived from $C_{12}$-$C_{18}$ fatty alcohols, for example coco fatty alcohol, tallow fatty alcohol, lauryl, myristyl, cetyl, or stearyl alcohol, or $C_{10}$-$C_{20}$ oxo alcohols. AO stands for an ethylene oxide (EO) or propylene oxide (PO) group, preferably for an ethylene oxide group. The index m stands for an integer from 1 to 50, preferably from 1 to 20, and in particular from 2 to 10. n very particularly preferably stands for the numbers 2, 3, 4, 5, 6, 7, or 8.

In summary, particularly preferred nonionic surfactants are selected from fatty alcohol ethoxylates of formula B-1

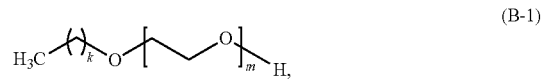

(B-1)

where k=11 to 19, m=2, 3, 4, 5, 6, 7, or 8. Particularly preferred representatives are $C_{12-18}$ fatty alcohols having 7 EO (k=11-17, m=7 in formula B-1).

Surfactant mixtures or detergents or cleaning agents which are preferred according to the invention are characterized in that they contain, based on the total quantity of all surfactants, 5 to 75% by weight, preferably 7.5 to 40% by weight, more preferably 10 to 35% by weight, even more preferably 12.5 to 32.5% by weight, and in particular 15 to 30% by weight, of surfactant(s) of formula $$R^8\text{—}O\text{-}(AO)_n\text{—}SO_3^-Y^+,$$

in which
R$^8$ stands for a linear or branched, substituted or unsubstituted alkyl, aryl, or alkylaryl radical,
AO stands for an ethylene oxide (EO) or propylene oxide (PO) group,
n stands for integers from 0 to 50,
Y$^+$ stands for a monovalent cation or the nth part of an n-valent cation.

In this formula, R$^8$ stands for a linear or branched, substituted or unsubstituted alkyl, aryl, or alkylaryl radical, preferably for a linear, unsubstituted alkyl radical, particularly preferably for a fatty alcohol radical. Preferred radicals R$^8$ are selected from decyl, undecyl, dodecyl, tridecyl, tetradecyl, pentadecyl, hexadecyl, heptadecyl, octadecyl, nonadecyl, eicosyl radicals and the mixtures thereof, the representatives having an even number of C atoms being preferred. Particularly preferred radicals R$^8$ are derived from $C_{12}$-$C_{18}$ fatty alcohols, for example coco fatty alcohol, tallow fatty alcohol, lauryl, myristyl, cetyl, or stearyl alcohol, or $C_{10}$-$C_{20}$ oxo alcohols.

Y$^+$ stands for a monovalent cation or the nth part of an n-valent cation; alkali metal ions, and among same, Na$^+$ or K$^+$, are preferred, with Na$^+$ being extremely preferred. Further cations Y$^+$ may be selected from $NH_4^+$, ½$Zn^{2+}$, ½$Mg^{2+}$, ½$Ca^{2+}$, ½$Mn^{2+}$, and the mixtures thereof.

In summary, particularly preferred surfactant mixtures contain surfactants selected from fatty alcohol sulfates of formula C-1

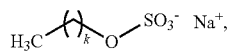

(C-1)

where k=11 to 19, n=2, 3, 4, 5, 6, 7, or 8. Very particularly preferred representatives are Na—$C_{12-14}$ fatty alcohol sulfates (k=11-13 in formula C-1).

When the index n in the formula $R^8$—O-$(AO)_n$—$SO_3^-X^+$ is not equal to zero, the formula describes the surfactants from the group of fatty alcohol ether sulfates. In this formula, R$^8$ stands for a linear or branched, substituted or unsubstituted alkyl, aryl, or alkylaryl radical, preferably for a linear, unsubstituted alkyl radical, particularly preferably for a fatty alcohol radical. Preferred radicals R$^8$ are selected from decyl, undecyl, dodecyl, tridecyl, tetradecyl, pentadecyl, hexadecyl, heptadecyl, octadecyl, nonadecyl, eicosyl radicals and the mixtures thereof, the representatives having an even number of C atoms being preferred. Particularly preferred radicals R$^8$ are derived from $C_{12}$-$C_{18}$ fatty alcohols, for example coco fatty alcohol, tallow fatty alcohol, lauryl, myristyl, cetyl, or stearyl alcohol, or $C_{10}$-$C_{20}$ oxo alcohols.

AO stands for an ethylene oxide (EO) or propylene oxide (PO) group, preferably for an ethylene oxide group. The index n stands for an integer from 1 to 50, preferably from 1 to 20, and in particular from 2 to 10. n very particularly preferably stands for the numbers 2, 3, 4, 5, 6, 7, or 8. X$^+$ stands for a monovalent cation or the nth part of an n-valent cation; alkali metal ions, and among same, Na$^+$ or K$^+$, are preferred, with Na$^+$ being extremely preferred. Further cations X$^+$ may be selected from $NH_4^+$, ½$Zn^{2+}$, ½$Mg^{2+}$, ½$Ca^{2+}$, ½$Mn^{2+}$, and the mixtures thereof.

In summary, particularly preferred surfactant mixtures contain surfactants selected from fatty alcohol ether sulfates of formula A-1

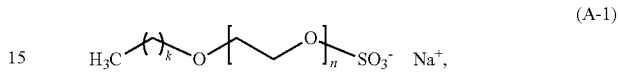

(A-1)

where k=11 to 19, n=2, 3, 4, 5, 6, 7, or 8. Very particularly preferred representatives are Na—$C_{12-14}$ fatty alcohol ether sulfates having 2 EO (k=11-13, n=3 in formula A-1).

The surfactants according to the invention are very well suited for complete or partial substitution of alkylbenzenesulfonates. Partial substitution is facilitated due to the fact that the surfactants according to the invention have excellent compatibility with alkylbenzenesulfonates, and increase their cleaning power even further.

According to the invention, at least one surfactant of formula $R^9$—$SO_3^-Y^+$ may be used as a further surfactant. In this formula, R$^9$ stands for a linear or branched, substituted or unsubstituted aryl or alkylaryl radical, preferably for a linear or branched, unsubstituted alkylaryl radical. Here as well, Y$^+$ stands for a monovalent cation or the nth part of an n-valent cation; alkali metal ions, and among same, Na$^+$ or K$^+$, are preferred, with Na$^+$ being extremely preferred. Further cations X$^+$ may be selected from $NH_4^+$, $Zn^{2+}$, ½$Mg^{2+}$, ½$Ca^{2+}$, ½$Mn^{2+}$, and the mixtures thereof.

Such extremely preferred surfactants are selected from linear or branched alkylbenzenesulfonates of formula C-2

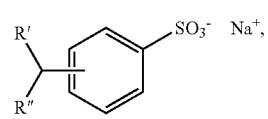

(C-2)

in which R' and R" together contain 9 to 19, preferably 11 to 15, and in particular 11 to 13, C atoms. A very particularly preferred representative may be described by formula C-2a:

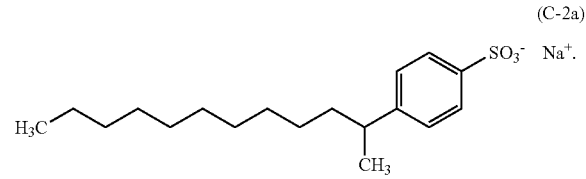

(C-2a)

The surfactant mixtures according to the invention may be provided as aqueous solutions, which facilitates dosing in the manufacturing process. Such liquid surfactant mixtures may also be used as liquid detergents or cleaning agents. Surfactant mixtures or liquid detergents or cleaning agents which are preferred according to the invention are characterized in that they contain, based on their weight, 1 to 90% by weight, preferably 10 to 85% by weight, particularly preferably 25 to 75% by weight, and in particular 35 to 65% by weight, of water.

Surfactant mixtures or detergents or cleaning agents. which are preferred according to the invention contain surfactant(s) according to the invention of formula (I), fatty alcohol ether sulfate(s), fatty alcohol ethoxylate(s), and alkylbenzenesulfonate(s).

These are very particularly preferably used within fairly narrow quantity ranges. Extremely preferred surfactant mixtures or detergents or cleaning agents contain, based on their weight,

- 1 to 70% by weight, preferably 2.5 to 40% by weight, and in particular 3 to 20% by weight, of surfactant(s) of formula (I),
- 0.1 to 70% by weight, preferably 0.25 to 40% by weight, and in particular 1 to 10% by weight, of fatty alcohol ether sulfate(s),
- 0.1 to 70% by weight, preferably 0.25 to 40% by weight, and in particular 1 to 10% by weight, of fatty alcohol ethoxylate(s),
- 0.1 to 70% by weight, preferably 0.25 to 40% by weight, and in particular 1 to 10% by weight, of alkylbenzenesulfonate(s).

Particularly preferred surfactant mixtures or liquid detergents or cleaning agents contain, based on the total quantity of the surfactants contained therein,

- 1 to 70% by weight, preferably 2.5 to 40% by weight, and in particular 3 to 20% by weight, of surfactant(s) of formula (I),
- 0.1 to 70% by weight, preferably 0.25 to 40% by weight, and in particular 1 to 10% by weight, of fatty alcohol ether sulfate(s) of formula A-1

$$H_3C\text{-}(\ )_k\text{-}O\text{-}(\ \ O)_n\text{-}SO_3^- \ Na^+, \quad (A\text{-}1)$$

where $k=11$ to 19, $n=2, 3, 4, 5, 6, 7$, or 8, particularly preferably Na—$C_{12\text{-}14}$ fatty alcohol ether sulfates having 3 EO ($k=11\text{-}13$, $n=3$), 0.1 to 70% by weight, preferably 0.25 to 40% by weight, and in particular 1 to 10% by weight, of fatty alcohol ethoxylate(s) of formula B-1

$$H_3C\text{-}(\ )_k\text{-}O\text{-}(\ \ O)_m\text{-}H, \quad (B\text{-}1)$$

where $k=11$ to 19, $m=2, 3, 4, 5, 6, 7$, or 8, particularly preferably $C_{12\text{-}18}$ fatty alcohols having 7 EO ($k=11\text{-}17$, $m=7$), 0.1 to 70% by weight, preferably 0.25 to 40% by weight, and in particular 1 to 10% by weight, of alkylbenzenesulfonate(s) of formula C-2

$$\text{(C-2)}$$

in which R' and R" together contain 9 to 19, preferably 11 to 15, and in particular 11 to 13, C atoms, particularly preferably alkylbenzenesulfonate(s) of formula C-2a $$\text{(C-2a)}$$

The surfactant system according to the invention is contained in the detergents or cleaning agents according to the invention, based on the total quantity of the detergent or cleaning agent, preferably in quantities of 1 to 80% by weight, more preferably 2.5 to 60% by weight, even more preferably 5 to 40% by weight, even more preferably 7.5 to 32.5% by weight, even more preferably 8.5 to 30% by weight, and in particular 10 to 25% by weight.

Preferred detergents or cleaning agents contain, based on the total quantity of the detergent or cleaning agent,

- 1 to 70% by weight, preferably 2.5 to 40% by weight, and in particular 3 to 20% by weight, of surfactant(s) of formula (I),
- 3 to 70% by weight, preferably 4 to 40% by weight, and in particular 8.5 to 9.5% by weight, of fatty alcohol ether sulfate(s),
- 2 to 70% by weight, preferably 3 to 40% by weight, and in particular 6.5 to 7.5% by weight, of fatty alcohol ethoxylate(s),
- 2 to 70% by weight, preferably 3 to 40% by weight, and in particular 6.5 to 7.5% by weight, of alkylbenzenesulfonate(s).

Particularly preferred detergents or cleaning agents contain, based on the total quantity of the detergent or cleaning agent,

- 1 to 70% by weight, preferably 2.5 to 40% by weight, and in particular 3 to 20% by weight, of surfactant(s) of formula (I),
- 3 to 70% by weight, preferably 4 to 40% by weight, and in particular 8.5 to 9.5% by weight, of fatty alcohol ether sulfate(s) of formula A-1

$$H_3C\text{-}(\ )_k\text{-}O\text{-}(\ \ O)_n\text{-}SO_3^- \ Na^+, \quad (A\text{-}1)$$

where $k=11$ to 19, $n=2, 3, 4, 5, 6, 7$, or 8, particularly preferably Na—$C_{12\text{-}14}$ fatty alcohol ether sulfates having 3 EO ($k=11\text{-}13$, $n=3$), 2 to 70% by weight, preferably 3 to 40% by weight, and in particular 6.5 to 7.5% by weight, of fatty alcohol ethoxylate(s) of formula B-1

$$H_3C\text{-}(\ )_k\text{-}O\text{-}(\ \ O)_m\text{-}H, \quad (B\text{-}1)$$

where k=11 to 19, m=2, 3, 4, 5, 6, 7, or 8, particularly preferably $C_{12-18}$ fatty alcohols having 7 EO (k=11-17, m=7), 2 to 70% by weight, preferably 3 to 40% by weight, and in particular 6.5 to 7.5%% by weight, of alkylbenzenesulfonate(s) of formula C-2

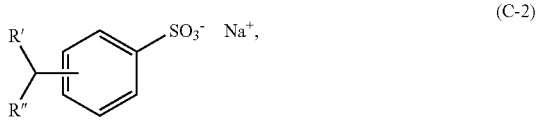

in which R' and R" together contain 9 to 19, preferably 11 to 15, and in particular 11 to 13, C atoms, particularly preferably alkylbenzenesulfonate(s) of formula C-2a

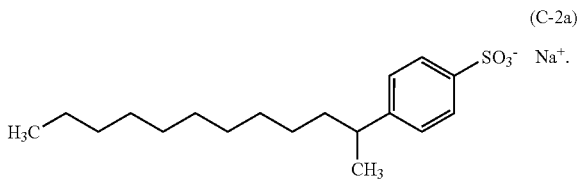

The agents according to the invention may also be formulated as cleaning agents for hard surfaces or hand dishwashing detergents. The term "cleaning agent" also includes cosmetics, as are used, for example, for cleaning the skin, hair, or body. Depending on the intended application of the cleaning agent, an agent according to the invention contains, in addition to the surfactants according to the invention and optionally further surfactants from the group of surfactants described above, further surfactants in a total quantity of typically 0.5 to 60% by weight, preferably 1 to 55% by weight, in particular 5 to 50% by weight, particularly preferably 10 to 45% by weight, and extremely preferably 15 to 40% by weight. Particularly preferred proportions are 18, 25, 32, and/or 36% by weight, for example.

In addition to surfactants according to the invention, alkyl ether sulfates, and optionally alkyl and/or aryl sulfonates, alkyl sulfates, and/or amphoteric surfactants, such agents according to the invention may also contain one or more further anionic surfactants, nonionic surfactants, and/or cationic surfactants, in particular for enhancing the cleaning action, flow behavior, and/or drying behavior.

In one preferred embodiment, the agent according to the invention contains one or more amphoteric surfactants, typically in a quantity of 0.1 to 20% by weight, preferably 1 to 15% by weight, in particular 2 to 12% by weight, particularly preferably 3 to 10% by weight, extremely preferably 4 to 8% by weight.

The agent according to the invention may additionally contain one or more further anionic surfactants, typically in a quantity of 0.001 to 5% by weight, preferably 0.01 to 4% by weight, in particular 0.1 to 3% by weight, particularly preferably 0.2 to 2% by weight, extremely preferably 0.5 to 1.5% by weight, for example 1% by weight. In this regard, sulfonate and sulfate surfactants such as alkylbenzenesulfonates, alkyl sulfonates, alkyl sulfates, and alkyl ether sulfates, but also sulfosuccinic acid derivatives, are mentioned in particular.

The agent according to the invention may additionally contain one or more nonionic surfactants, typically in a quantity of 0.001 to 5% by weight, preferably 0.01 to 4% by weight, in particular 0.1 to 3% by weight, particularly preferably 0.2 to 2% by weight, extremely preferably 0.5 to 1.5% by weight, for example 1% by weight.

Within the scope of the invention, nonionic surfactants are alkoxylates such as polyglycol ethers, fatty alcohol polyglycol ethers, alkylphenol polyglycol ethers, and polyglycol ethers, mixed ethers, and hydroxy mixed ethers closed by a terminal group, and fatty acid polyglycol esters. Block polymers of ethylene oxide and propylene oxide, as well as fatty acid alkanolamides and fatty acid polyglycol ethers, are likewise suitable. In addition, aminoxides and sugar surfactants, in particular alkyl polyglucosides, are important classes of nonionic surfactants according to the invention.

It is preferred that the detergents or cleaning agents according to the invention contain an enzyme or a mixture of enzymes. Those from the class of hydrolases, such as proteases, (poly)esterases, lipases, amylases, glycosyl hydrolases, hemicellulases, cutinases, β-glucanases, oxidases, peroxidases, mannanases, perhydrolases, oxireductases, and/or laccases are particularly suitable.

The quantity of enzyme or enzymes is preferably 0.01 to 10% by weight, preferably 0.12 to approximately 3% by weight, based on the overall detergent or cleaning agent. The enzymes are preferably used as liquid enzyme formulation(s).

In addition to the surfactant(s) according to the invention of formula (I) or the surfactant system according to the invention, the detergent or cleaning agent according to the invention may contain further ingredients which further improve the application-related and/or esthetic properties of the detergent or cleaning agent. Within the scope of the present invention, the detergent or cleaning agent preferably additionally contains one or more substances from the group of builders, bleaching agents, electrolytes, nonaqueous solvents, pH adjusters, fragrances, fragrance carriers, fluorescence agents, dyes, hydrotopes, foam inhibitors, silicone oils, anti-redeposition agents, graying inhibitors, shrinkage inhibitors, anti-crease agents, dye transfer inhibitors, antimicrobial active substances, germicides, fungicides, antioxidants, preservatives, corrosion inhibitors, anti-static agents, bittering agents, ironing aids, repellent and impregnation agents, swelling and anti-slip agents, softening components, and UV absorbers.

In particular silicates, aluminum silicates (in particular zeolites), carbonates, salts of organic di- and polycarboxylic acids, and mixtures of these substances are mentioned as builders which may be contained in the detergent or cleaning agent.

Organic builders which may be present in the detergent or cleaning agent are, for example, polycarboxylic acids which are usable in the form of their sodium salts, polycarboxylic acids being understood to mean carboxylic acids which bear more than one acid function. Examples of such are citric acid, adipic acid, succinic acid, glutaric acid, malic acid, tartaric acid, maleic acid, fumaric acid, saccharic acids, aminocarboxyic acids, nitrilotriacetic acid (NTA), methylglycinediacetic acid (MGDA), and the derivatives and mixtures thereof. Preferred salts are the salts of polycarboxylic acids such as citric acid, adipic acid, succinic acid, glutaric acid, tartaric acid, saccharic acids, and mixtures thereof.

In addition, polymeric polycarboxylates are suitable as builders. Examples of such are the alkali metal salts of polyacrylic acid or of polymethacrylic acid, for example those having a relative molecular mass of 600 to 750,000 g/mol.

Suitable polymers are in particular polyacrylates which preferably have a molecular mass of 1,000 to 15,000 g/mol. Due to their superior solubility, short-chain polyacrylates having molar masses of 1,000 to 10,000 g/mol, and particularly preferably 1,000 to 5,000 g/mol, may in turn be preferred from this group.

Also suitable are copolymeric polycarboxylates, in particular those of acrylic acid with methacrylic acid, and of acrylic acid or methacrylic acid with maleic acid. To improve the solubility in water, the polymers may also contain allylsulfonic acids, such as allyloxybenzenesulfonic acid and methallylsulfonic acid, as monomer.

However, soluble builders such as citric acid, or acrylic polymers having a molar mass of 1,000 to 5,000 g/mol, are preferably used in the detergents or cleaning agents.

EXAMPLES

Manufacturing Specification

The phenolic compound was reacted with the corresponding alkene at temperatures higher than 100° C. in the presence of a catalyst. The reaction mixture was washed with water and salt solution, and the product was extracted with dichloromethane and isolated by removal of the dichloromethane.

If tetradecene, for example, was used as the alkene, the reaction took place at 160° C. in the presence of the catalyst Amberlyst™ 70 (manufacturer: The Dow Chemical Company).

The sulfonation of the alkylated phenolic compound took place at room temperature, using sulfuric acid. The solvent was stripped, and the residue was dissolved in methyl tert-butyl ether. After filtration, the product was isolated by removal of the methyl tert-butyl ether.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. Surfactants of formula (I)

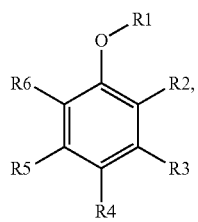

(I)

in which
R$^1$ stands for —CH$_3$,
R$^2$, R$^3$, R$^4$, R$^5$, R$^6$ independently stand for —H, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —OH, —OCH$_3$, —OCH$_2$CH$_3$, —OCH$_2$CH$_2$CH$_3$, —OCH(CH$_3$)$_2$, a linear or branched alkyl radical containing 8 to 20 C atoms, or —SO$_3^-$X$^+$,
X$^+$ stands for a monovalent cation or the nth part of an n-valent cation,
with the condition that
exactly one radical R$^2$, R$^3$, R$^4$, R$^5$, R$^6$ stands for —SO$_3^-$X$^+$ and
exactly one radical R$^2$, R$^3$, R$^4$, R$^5$, R$^6$ stands for a linear or branched alkyl radical containing 8 to 20 C atoms.

2. Surfactants according to claim 1, characterized in that they have a CMC of less than 0.1 g/L.

3. Surfactants according to claim 1, characterized in that they have an interfacial tension of less than 2 mN/m.

4. Surfactants according to claim 1, characterized in that they have a CMC of 0.01 to 0.06 g/L and at the same time produce an interfacial tension of 1.6 mN/m maximum.

5. Surfactants according to claim 1, characterized in that the surfactant(s) is/are selected from surfactants of formulas (Ia) and/or (Ib) and/or (Ic) and/or (Id)

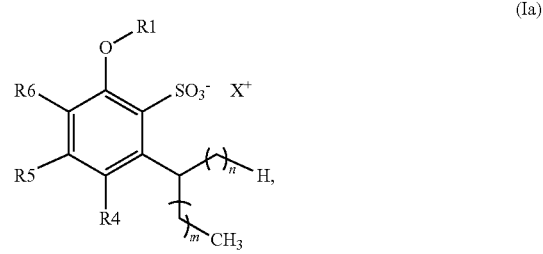

(Ia)

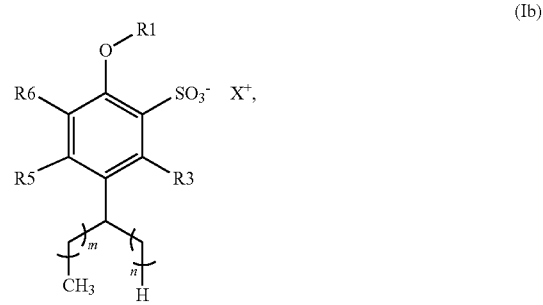

(Ib)

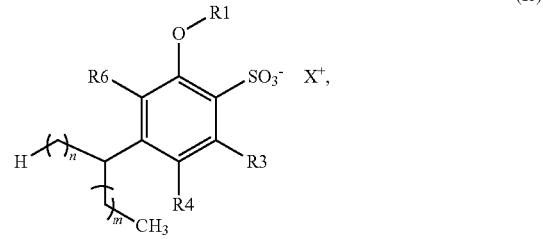

(Ic)

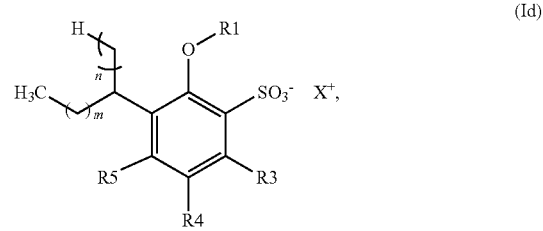

(Id)

in which

R$^1$ stands for —CH$_3$,

R$^3$, R$^4$, R$^5$, R$^6$ independently stand for —H, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —OH, —OCH$_3$, —OCH$_2$CH$_3$, —OCH$_2$CH$_2$CH$_3$, —OCH(CH$_3$)$_2$, n, m independently stand for integers from 0 to 18, with the condition that the sum (m+n) stands for one of the numbers 6, 7, 8, 9, 10, 11, 12, 13, 14, 15, 16, 17, or 18.

6. Surfactants according to claim 1, characterized in that the surfactant(s) is/are selected from surfactants of formulas (Ie) and/or (If) and/or (Ig) and/or (Ih)

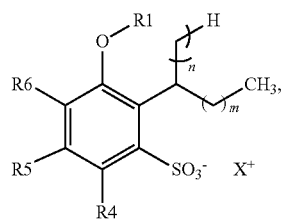
(Ie)

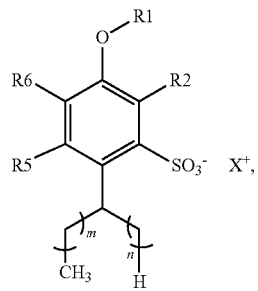
(If)

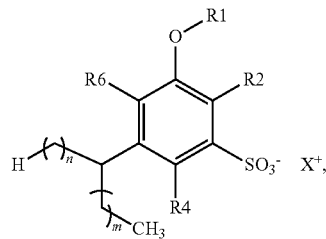
(Ig)

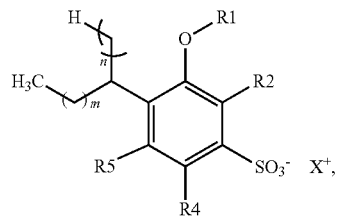
(Ih)

in which

R$^1$ stands for —CH$_3$,

R$^2$, R$^4$, R$^5$, R$^6$ independently stand for —H, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —OH, —OCH$_3$, —OCH$_2$CH$_3$, —OCH$_2$CH$_2$CH$_3$, —OCH(CH$_3$)$_2$, n, m independently stand for integers from 0 to 18, with the condition that the sum (m+n) stands for one of the numbers 6, 7, 8, 9, 10, 11, 12, 13, 14, 15, 16, 17, or 18.

7. Surfactants according to claim 1, characterized in that the surfactant(s) is/are selected from surfactants of formulas (Ii) and/or (Ij) and/or (Ik) and/or (Im)

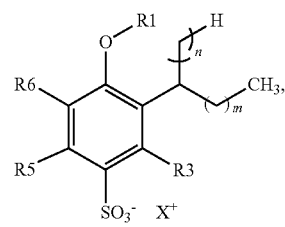
(Ii)

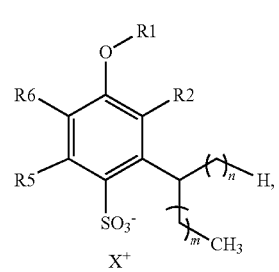
(Ij)

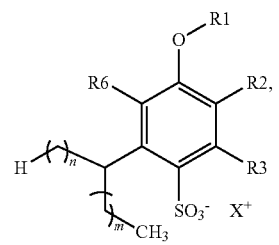
(Ik)

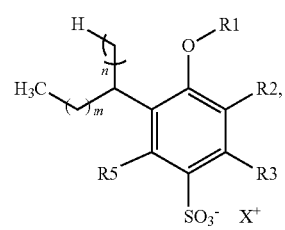
(Im)

in which

R$^1$ stands for —CH$_3$,

R$^2$, R$^3$, R$^5$, R$^6$ independently stand for —H, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —OH, —OCH$_3$, —OCH$_2$CH$_3$, —OCH$_2$CH$_2$CH$_3$, —OCH(CH$_3$)$_2$, n, m independently stand for integers from 0 to 18, with the condition that the sum (m+n) stands for one of the numbers 6, 7, 8, 9, 10, 11, 12, 13, 14, 15, 16, 17, or 18.

8. Surfactant mixture comprising
a) at least one surfactant according to claim 1 and
b) at least one further surfactant.

9. Surfactant mixture according to claim 8, comprising, based on the total quantity of all surfactants, 5 to 75% by weight, of surfactant(s) of formula

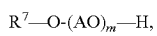

in which

R$^7$ stands for a linear or branched, substituted or unsubstituted alkyl, aryl, or alkylaryl radical, AO stands for an ethylene oxide (EO) or propylene oxide (PO) group, m stands for integers from 1 to 50.

10. Surfactant mixture according to claim 8, comprising, based on the total quantity of all surfactants, 5 to 75% by weight, of surfactant(s) of formula $$R^8\text{---}O\text{-}(AO)_n\text{---}SO_3^-Y^+,$$

in which $R^8$ stands for a linear or branched, substituted or unsubstituted alkyl, aryl, or alkylaryl radical, AO stands for an ethylene oxide (EO) or propylene oxide (PO) group, n stands for integers from 0 to 50, $Y^+$ stands for a monovalent cation or the nth part of an n-valent cation.

11. Surfactant mixture according to claim 8, comprising, 1 to 90% by weight, of water.

12. Detergent or cleaning agent containing at least one surfactant according to claim 1.

13. Detergent or cleaning agent according to claim 12, characterized in that it is liquid and comprises, 1 to 90% by weight, of water.

14. Surfactant mixture according to claim 5, comprising, 1 to 99% by weight, of at least one surfactant selected from the group consisting of formula (Ia), (Ib), (Ic), (Id).

15. Surfactant mixture according to claim 6, comprising, 1 to 99% by weight, of at least one surfactant selected from the group consisting of formula (Ie), (If), (Ig), (Ih).

16. Surfactant mixture according to claim 7, comprising, 1 to 99% by weight, of at least one surfactant selected from the group consisting of formula (Ii), (Ij), (Ik) and (Im).

* * * * *